(12) United States Patent
Bott et al.

(10) Patent No.: US 12,180,522 B2
(45) Date of Patent: *Dec. 31, 2024

(54) POLYPEPTIDES WITH ENDOGLUCANASE ACTIVITY AND USES THEREOF

(71) Applicant: DANISCO US INC, Palo Alto, CA (US)

(72) Inventors: Richard Bott, Kirkland, WA (US); David A. Estell, San Mateo, CA (US); Neeraj Pandey, Clapham (GB); Sina Pricelius, Leiden (NL); Jian Yao, Sunnyvale, CA (US)

(73) Assignee: Danisco US Inc., Palo Alto, CA (US)

( * ) Notice: Subject to any disclaimer, the term of this patent is extended or adjusted under 35 U.S.C. 154(b) by 343 days.

This patent is subject to a terminal disclaimer.

(21) Appl. No.: 17/328,003

(22) Filed: May 24, 2021

(65) Prior Publication Data

US 2021/0388334 A1    Dec. 16, 2021

Related U.S. Application Data

(62) Division of application No. 16/469,464, filed as application No. PCT/US2017/066267 on Dec. 14, 2017, now Pat. No. 11,053,488.

(60) Provisional application No. 62/435,340, filed on Dec. 16, 2016.

(30) Foreign Application Priority Data

Dec. 15, 2016   (BD) .................................... 306/2016

(51) Int. Cl.
| | | |
|---|---|---|
| *C12N 9/24* | (2006.01) | |
| *C11D 3/386* | (2006.01) | |
| *C12N 9/42* | (2006.01) | |
| *D21H 17/00* | (2006.01) | |

(52) U.S. Cl.
CPC ........ *C12N 9/2437* (2013.01); *C11D 3/38645* (2013.01); *C11D 3/38654* (2013.01); *C12Y 302/01004* (2013.01); *D21H 17/005* (2013.01)

(58) Field of Classification Search
CPC .......................... C12N 9/24; C12Y 302/01004
See application file for complete search history.

(56) References Cited

U.S. PATENT DOCUMENTS 11,053,488 B2 *   7/2021   Bott ..................... D21H 17/005

* cited by examiner

*Primary Examiner* — Tekchand Saidha

(57) ABSTRACT

Disclosed herein are cellulase variants, or active fragments thereof, and polynucleotides encoding same, where the cellulase variants, or active fragments thereof, have endoglucanase activity. Also disclosed herein are compositions comprising the cellulase variants, or active fragments thereof; vectors and/or host cells comprising the polynucleotides encoding the cellulase variants, or active fragments thereof; and methods for making and/or using the cellulase variants, or active fragments thereof and/or compositions containing same; where the cellulase variants, or active fragments thereof, have endoglucanase activity.

21 Claims, 13 Drawing Sheets

Specification includes a Sequence Listing.

```
             1              10              20              30              40              50
             |               |               |               |               |               |
STCE1-WT         ADG--KSTRYWDCCKPSCSWPGKASVNQPVFACSANFQRISDPNVKSGCD--GGSAYACAD
C. thermophilum  ADG--KSTRYWDCCKPSCSWPGKAAVSQPVFACDRNFNRIYDFGAKSGCE--GGPAYSCAD
H. insolens      ADG--RSTRYWDCCKPSCGWAKKAPVNQPVFSCNANFQRITDFDAKSGCEPGGVAYSCAD
H. grisea        ADG--KSTRYWDCCKPSCGWAKKAPVNQPVFSCNANFQRLTDFDAKSGCEPGGVAYSCAD
T. terrestris    ASGSGQSTRYWDCCKPSCAWPGKAAVSQPVYACDANFQRLSDFNVQSGCN--GGSAYSCAD
A. thermophilum  LDG--KSTRYWDCCKPSCGWAGKASVNQPVFSCSADWQRISDFNAKSGCD--GGSAYSCAD
N. crassa        ASGSGQSTRYWDCCKPSCSWSGKAPVNRPVLACDANNNPLSDASVKSGCD--GGSAYTCAN
STCE1-5217       ADG--KSTRYWDCCKPSCSWPGKASVNQPVFACSANFTRISDPNVVSGCD--GGSAYACAD
STCE1-5504       ADG--VSTRYWDCCKPSCSWPGKAAVSQPVFACSANFQRISDPNVVSGCD--GGSAYACAD
STCE1-5267       ADG--VSTRYWDCCKPSCSWPGKASVNQPVFACSANFQRISDPNVKSGCD--GGSAYACAD
STCE1-5349       ADG--KSTRYWDCCKPSCSWPGKASVNQPVFACYANFQRISDPNVKSGCD--GGSAYACAD
STCE1-5434       ADG--VSTRYWDCCKPSCSWPGKASVNQPVFACSANFQRISDPNVVSGCD--GGSAYACAD
STCE1-5443       ADG--KSTRYWDCCKPSCSWPGKAAVSQPVYACDANFQRISDPNVKSGCD--GGSAYACAD
STCE1-5286       ADG--KSTRYWDCCKPSCSWPGKASVNQPVFACSANFQRISDPNVKSGCD--GGSAYACAD
STCE1-5324       ADG--KSTRYWDCCKPSCSWPGKASVNQPVFACSANFQRISDPNVKSGCD--GGSAYACAD
STCE1-5207       ADG--KSTRYWDCCKPSCSWPGKASVNQPVFACSANFTRISDPNVKSGCD--GGSAYACAD
STCE1-5219       ADG--VSTRYWDCCKPSCSWPGKALVNQPVFACSANFQRISDPNVKSGCD--GGSAYACAD
STCE1-5225       ADG--VSTRYWDCCKPSCSWPGKASVNQPVWACSANFQRISDPNVVSGCD--GGSAYACAD
STCE1-5238       ADG--KSTRYWDCCKPSCSWPGKASVNQPVFACYANFQRISDPNVKSGCD--GGSAYACAD
STCE1-5248       ADG--VSTRYWDCCKPSCSWPGKASVNQPVWACSANFQRISDPNVKSGCD--GGSAYACAD
STCE1-5250       ADG--KSTRYWDCCKPSCSWPGKASVNQPVFACSANFTRISDPNVKSGCD--GGSAYACAD
STCE1-5258       ADG--VSTRYWDCCKPSCSWPGKASVNQPVFACSANFTRISDPNVKSGCD--GGSAYACAD
STCE1-5276       ADG--KSTRYWDCCKPSCSWPGKASVNQPVFACSANFQRISDPNVKSGCD--GGSAYACAD
STCE1-5279       ADG--VSTRYWDCCKPSCSWPGKASVNQPVWACSANFQRISDPNVKSGCD--GGSAYACAD
STCE1-5281       ADG--KSTRYWDCCKPSCSWPGKASVNQPVFACSANFQRISDPNVKSGCD--GGSAYACAD
STCE1-5308       ADG--VSTRYWDCCKPSCSWPGKASVNQPVFACSANFQRISDPNVKSGCD--GGTAYACAD
STCE1-5316       ADG--KSTRYWDCCKPSCSWPGKASVNQPVFACYANFQRISDPNVKSGCD--GGTAYACAD
STCE1-5322       ADG--VSTRYWDCCKPSCSWPGKALVNQPVFACSANFQRISDPNVKSGCD--GGSAYACAD
STCE1-5334       ADG--KSTRYWDCCKPSCSWPGKASVNQPVFACYANFQRISDPNVVSGCD--GGSAYACAD
STCE1-5340       ADG--VSTRYWDCCKPSCSWPGKASVNQPVFACSADFQRISDPNVKSGCD--GGTAYACAD
STCE1-5354       ADG--KSTRYWDCCKPSCSWPGKASVNQPVFACSANFTRISDPNVKSGCD--GGSAYACAD
STCE1-5379       ADG--VSTRYWDCCKPSCSWPGKASVNQPVFACSANFQRISDPNVKSGCD--GGTAYACAD
STCE1-5385       ADG--KSTRYWDCCKPSCSWPGKASVNQPVFACSANFQRISDPNVKSGCD--GGTAYACAD
STCE1-5398       ADG--VSTRYWDCCKPSCSWPGKASVNQPVFACSANFTRISDPNVKSGCD--GGSAYACAD
STCE1-5431       ADG--VSTRYWDCCKPSCSWPGKASVNQPVFACSANFQRISDPNVKSGCD--GGTAYACAD
```

| | | 120 | 130 | 140 | 150 | 160 | 170 |
|---|---|---|---|---|---|---|---|
| STCE1-5433 | | HFDLAMPGGGVGIFDGCSPQFGGLPGDRYGGVSSRSECDSFPAALKPGCYWRFDWFKNAD |
| STCE1-5448 | | HFDLAMPGGGVGIFDGCSPQFGGLPGDRYGGVSSRSQCDSFPAALKPGCYWRFDWFKNAD |
| STCE1-5450 | | HFDLAMPGGSVGIFDGCSPQFGGLPGDRYGGVSSRSQCDSFPAPLKPGCYWRFDWFKNAD |
| STCE1-5452 | | HFDLAMPGGGVGIFDGCSPQFGGLPGDRYGGVSSRSQCDSFPAALKPGCYWRFDWFKNAD |
| STCE1-5458 | | HFDLAMPGGGVGIFDGCSPQFGGLPGDRYGGVSSRSQCDSFPAPIKPGCYWRFDWFKNAD |
| STCE1-5491 | | HFDLAMPGGGVGIFDGCSPQFGGLAGDRYGGVSSRSQCDSFPAALKPGCYWRF-WFKNA- |
| STCE1-5500 | | HFDLAMPGGGVGIFDGCSEQFGGLPGDRYGGVSSRSQCDSFPAPLKPGCYWRFDWFKNAD |
| STCE1-5539 | | HFDLAMPGGGVGIFDGCSPQFGGLPGDRYGGVSSRSQCDSFPAELKPGCYWRFDWFKNAD |
| STCE1-5542 | | HFDLAMPGGGVGIFDGCSEQFGGLPGDRYGGVSSRSQCDSFPAALKPGCYWRFDWFKNAD |
| STCE1-5543 | | HFDLAMPGGGVGIFDGCSPQFGGLPGDRYGGVSSRSQCDSFPAALKPGCYWRFDWFKNAD |
| STCE1-5546 | | HFDLAMPGGGVGIFDGCSPQFGGLPGDRYGGVSSRSQCDSFPAALKPGCYWRFDWFKNAD |
| STCE1-5547 | | HFDLAMPGGGVGIFDGCSEQFGGLPGDRYGGVSSRSQCDSFPAPIKPGCYWRFDWFKNAD |
| STCE1-5550 | | HFDLAMPGGGVGIFDGCSPQFGGLPGDRYGGVSSRSQCDSFPAALKPGCYWRFDWFKNAD |
| STCE1-5552 | | HFDLAMPGGGVGIFDGCSPQFGGLEGDRYGGVSSRSQCDSFPAELVPGCYWRFDWFKNAD |
| STCE1-5557 | | HFDLAMPGGGVGIFDGCSKQFGGLPGDRYGGVSSRSQCDSFPAELKPGCYWRFDWFKNAD |
| STCE1-5560 | | HFDLAMPGGGVGIFDGCSPQFGGLPGDRYGGVSSRDQCDSFPAALKPGCYWRFDWFKNAD |
| STCE1-5561 | | HFDLAMPGGGVGIFDGCSPQFGGLPGDRYGGVSSRSQCDSFPAALKPGCYWRFDWFKNAD |
| STCE1-5562 | | HFDLAMPGGGVGIFDGCTPQFGGLPGDRYGGVSSRSQCDSFPAALKPGCYWRFDWFKNAD |
| STCE1-5563 | | HFDLAMPGGGVGIFDGCSPQFGGLPGDRYGGVSSRSQCDSFPAPLKPGCYWRFDWFKNAD |
| STCE1-5567 | | HFDLAMPGGGVGIFDGCSPQFGGLPGDRYGGVSSRSQCDSFPAALVPGCYWRFDWFKNAD |
| STCE1-5575 | | HFDLAMPGGGVGIFDGCSPQFGGLPGDRYGGVSSRSECGSFPAALKPGCYWRFDWFKNAD |
| STCE1-5576 | | HFDLAMPGGGVGIFDGCSPQFGGLPGDRYGGVSSRSQCDSFPAALKPGCYWRFDWFKNAD |
| STCE1-5609 | | HFDLAMPGGGVGIFDGCSPQFGGLPGDRYGGVSSRSQCDSFPAELKPGCYWRFDWFKNAD |
| STCE1-5611 | | HFDLAMPGGGVGIFDGCTPQFGGLPGDRYGGVSSRSQCDSFPAALKPGCYWRFDWFKNAD |
| STCE1-5612 | | HFDLAMPGGGVGIFDGCSPQFGGLPGDRYGGVSSRDQCDSFPAPLKPGCYWRFDWFKNAD |
| STCE1-5614 | | HFDLAMPGGGVGIFDGCSPQFGGLAGDRYGGVSSRSQCDSFPAALVPGCYWRFDWFKNAD |
| STCE1-5616 | | HFDLAMPGGGVGIFDGCSPQFGGLPGDRYGGVSSRSQCDSFPAPIKPGCYWRFDWFKNAD |
| STCE1-5684 | | HFDLAMPGGGVGIFDGCSPQFGGLAGDRYGGVSSRSECGSFPAALKPGCYWRFDWFKNAD |
| STCE1-5343 | | HLDLAMPGGGVGIFDGCSPQFGGLPGDRYGGVSSRSQCDSFPAALKPGCYWRFDWFKNAD |
| STCE1-5401 | | HFDLAMPGGGVGIFDGCTPQFGGLAGDRYGGVSSRSQCDSFPAPLKPGCYWRFDWFKNAD |
| STCE1-5355 | | HFDLAMPGGGVGIFDGCSPQFGGLPGDRYGGVSSRDQCDSFPAALKPGCYWRFDWFKNAD |
| STCE1-5287 | | HFDLAMPGGGVGIFDGCTPQFGGLAGDRYGGVSSRSQCDSFPAALVPGCYWRFDWFKNAD |
| STCE1-5357 | | HFDLAMPGGGVGIFDGCSPQFGGLAGDRYGGVSSRSECDSFPAPIKPGCYWRFDWFKNAD |
| STCE1-5460 | | HFDLAMPGGGVGIFDGCSPQFGGLPGDRYGGVSSRSQCDSFPAPLKPGCYWRFDWFKNAD |
| STCE1-5683 | | HFDLAMPGGGVGIFDGCSEQFGGLAGDRYGGVSSRSQCDDFPAALKPGCYWRF-WFKNAD |

FIG 2F

```
                          180         190         200       211
                            |           |           |         |
STCE1-5433     NPFFTFRQVQCPSELVARTGCRMDDGSNFPVFTP
STCE1-5448     NPFFTFRQVQCPSELVARTGCRMDDGDFPVFTP
STCE1-5450     NPFETFRQVQCPSEVVARTGCRMDDSNFPVFTP
STCE1-5452     NPFFTFRQVQCPSELVARTGCRMDDGSNFPVFTP
STCE1-5458     NPFFTFRQVQCPSELVARTGCRMDDGNFPVFTP
STCE1-5491     NPFFTFRQVQCPSELVARTGCRMNDGNFPHFTP
STCE1-5500     NPFFTFRQVQCPSELVARTGCRMDDGNFPVFTP
STCE1-5539     NPFFTFRQVQCPSELVARTGCRMDDGNFPVFTP
STCE1-5542     NPFFTFRQVQCPSELVARTGCRMDDGSNFPVFTP
STCE1-5543     NPFFTFRQVQCPSELVARTGCRMDDGSNFPVFTP
STCE1-5546     NPFFTFRQVQCPSELVARTGCRMDDGSNFPVFTP
STCE1-5547     NPFFTFRQVQCPSELVARTGCRMDDGNFPVFTP
STCE1-5550     NPFFTFRQVQCPSELVARTGCRMDDGNFPVFTP
STCE1-5552     NPFFTFRQVQCPSELVARTGCRMDDGNFPVFTP
STCE1-5557     NPFFTFRQVQCPSELVARTGCRMDDGSNFPVFTP
STCE1-5560     NPFFTFRQVQCPSELVARTGCRMDDGSNFPVFTP
STCE1-5561     NPFFTFRQVQCPSELVARTGCRMDDGSNFPVFTP
STCE1-5562     NPFFTFRQVQCPSELVARTGCRMDDGNFPVFTP
STCE1-5563     NPFFTFRQVQCPSELVARTGCRMDDGNFPVFTP
STCE1-5567     NPFFTFRQVQCPSELVARTGCRMDDGNFPVFTP
STCE1-5575     NPFFTFRQVQCPSELVARTGCRMDDGNFPVFTP
STCE1-5576     NPFFTFRQVQCPSELVSRTGCRMDDGNFPVFTP
STCE1-5609     NPFFTFRQVQCPSELVARTGCRMDDGNFPVFTP
STCE1-5611     NPFFTFRQVQCPSELVARTGCRMDDGNFPVFTP
STCE1-5612     NPFETFRQVQCPSELVARTGCRMDDGNFPVFTP
STCE1-5614     NPFFTFRQVQCPSELVARTGCRMDDGNFPVFTP
STCE1-5616     NPFFTFRQVQCPSELVARTGCRMDDGNFPKFTP
STCE1-5664     NPFFTFRQVQCPSELVARTGCRMDDGNFPVFTP
STCE1-5343     NPFFTFRQVQCPSELVARTGCRMDDGNFPVFTP
STCE1-5401     NPFFTFRQVQCPSELVARTGCRMDDGNFPVFTP
STCE1-5355     NPFFTFRQVQCPSELVARTGCRMDDSNFPVFTP
STCE1-5297     NPFFTFRQVQCPSELVARTGCRMDDGNFPVFTP
STCE1-5357     NPFFTFRQVQCPSELVARTGCRMDDGNFPVFTP
STCE1-5460     NPFFTFRQVQCPSELVARTGCRMDDGNFPVFTP
STCE1-5663     NPFFTFRQVQCPSELVARTGCRMDDGNFPVFTP
```

```
                  212        220          230          240          250      258
                   |          |            |            |            |        |
STCE1-5433   PS-------GGQSSSSSSSSSARPTSTST------------STTSTKATSTTSTASSQTSSSTG--GG
STCE1-5448   PS-------GGQSSSSSSSSSSAKPTSTST------------STTSTSDKATSTTSTASSQTSSSTG--GG
STCE1-5450   PS-------GGQSSSSSSSSSSAKPTSTST------------STTSTKAASTTSTASSQTSSSTG--GG
STCE1-5452   PS-------GGQSSSSSSSSSSAKPTSTSTSA----------STTSTSDKATSTTSTASSQTSSSTG--GG
STCE1-5458   PS-------GGQSSSSSSSSSSARPTSTST------------STTSTKATSTTSTASSQTSSSTG--GG
STCE1-5491   PS-------GGQSSSSSSSSSSAKPTSTST------------STTSTKATSTTSTASSQTSSSTG--GG
STCE1-5500   PS-------GGQSSSSSLSSSSAKPTSTST------------STTSTKATSTTSTASSQTSSSTG--GG
STCE1-5539   PS-------GGQSSSSSSSSKKAKPTSTST------------STTSTKATSTTSTASSQTSSSTG--GG
STCE1-5542   PS-------GGQSSSSSSSSSSAKPTSTST------------STTSTKATSTTSTASPQTSSSTG--GG
STCE1-5543   PS-------GGQSSSSSLSSSSAKPTSTST------------STTSTKATSTTSTASSQTSSSTG--GG
STCE1-5546   PS-------GGQSSSSSSSSSSKAKPTSTST-----------STTSTKATSTTSTASSQTSSSTG--GG
STCE1-5547   PS-------GGQSSSSSSSSSSAKPTSTST------------STTSTKATSTTSTASSQTSSSTG--GG
STCE1-5550   PS-------GGQSSSSSSSSSSAKPTSTST------------STTSTKATSTTSTASSQTSSSTG--GG
STCE1-5552   PS-------GGQSSSSSSSSSSAKPTSTST------------STTSTKATSTTSTASSQTSSSTG--GG
STCE1-5557   PS-------GGQSSSSSSSSSSAKPTSTST------------STTSTKATSTTSTASSQTSSSTG--GG
STCE1-5560   PS-------GGQSSSSSSSSSSAKPTSTST------------STTSTKATSTTSTASSQTSSSTG--GG
STCE1-5561   PS-------GGQSSSSSSSSSSAKPTSTST------------STTSTKATSTTSTASSQTSSSTG--GG
STCE1-5562   PS-------GGQMSSSMSSSSSSAKPTSTST-----------STTSTKALSTTSTASGQTSSSTG--KG
STCE1-5563   PS-------GGQSSSSSSSSSSAKPTSTST------------STTSTKATSTTSTASGQTSSSTG--KG
STCE1-5567   PS-------GGQSSSSSAASSSSAKPTSTST-----------STTSTKATSTTSTASSQTSSSTG--GG
STCE1-5575   PS-------GGQSSSSSSSSSSAKPTSTST------------STTSTKARSTTSTASSQTSSSTG--GG
STCE1-5576   SS-------GGQSSSSSSSSSSAKPTSTST------------STTSTKARSTTSTASSQTSSSTG--GG
STCE1-5609   PS-------GGQSSSSSSSSSSAKPTSTST------------STTSTKATSTTSTASSQTSSSTG--GG
STCE1-5611   PS-------GGQSSSSSSSSSSAKPTSTST------------STTSTKATSTTSTASSQTSSSTG--GG
STCE1-5612   PS-------GGQSSSSSSSSSSAKPTSTST------------STASTKATSTTSTASSQTSSSTG--GG
STCE1-5614   PS-------GGQSSSSSSSSSSKAKPTSTTST----------STASTKTTDTTSTASSQTSSSTG--GG
STCE1-5616   PS-------GGQSSSSSSSSSSAKPTSTTS--TAASTKATSTTSTTSDKATSTTSTASSQTSSSTG--GG
STCE1-5684   PS-------GGQSSSSSSSSSSAKPTSTST------------STTSTKATSTTSTASSQTSSSTG--GG
STCE1-5343   PS-------GGQSSSSSSSSSSARPTSTSTSTSTSTSTSTTDTTSTTSTTDKATSTTSTASSQTSSSTG--GG
STCE1-5401   PS-------GGQSSSSSSSSSSAKPTSTSTSTT---TASTKATSTTSTKATSTTSTASSQTSSSTG--GG
STCE1-5355   PS-------GGQSSSSSSSSSSAKPTSTST------------STTSTKATSTTSTASSQTSSSTG--GG
STCE1-5287   PS-------GGQSSSSSSSSSSAKPTSTST------------STTSTKATSTTSTASSQTSSSTG--GG
STCE1-5357   PS-------GGQSSSSSLSSSSAKPTSTST------------STTSTKATSTTSTASSQTSSSTG--GG
STCE1-5460   PS-------GGQSSSSSSSSSSAKPTSTST------------STTSTKATSTTSTASSQTSSSTG--GG
STCE1-5683   PS-------GGQSSSSSLSSSSAKPTSTST------------STTSTKATSDKATSTTSTASSQTSSSTG--GG
```

FIG 3B

| | 289 | 270 | 280 | 290 | 295 |
|---|---|---|---|---|---|
| STCE1-5433 | CAAQRWAQCGGIGFSGCTTCVSGTTCNKQNDWYSQC------L |
| STCE1-5448 | CAAQRWAQCGGIGFSGCTTCVSGTTCNKQNDWYSQC------L |
| STCE1-5450 | CAAQRWAQCGGIGFSGCTTCVSGTTCNKQNDWYSQC------L |
| STCE1-5452 | CAAQRWAQCGGIGFSGCTTCVSGTTCNKQNDWYSQC------L |
| STCE1-5458 | CAAQRWAQCGGIGFSGCTTCVSGTTCNKQNDWYSQC------L |
| STCE1-5491 | CAAQRWAQCGGIGFSGCTTCVSGTTCNKQNDWYSQC------L |
| STCE1-5500 | CAAQRWAQCGGIGFSGCTTCVSGTTCNKQNDWYSQC------L |
| STCE1-5539 | CAAQRWAQCGGIGFSGCTTCVSGTTCNKQNDWYSQC------L |
| STCE1-5542 | CAAQRWAQCGGIGFSGCTTCVSGTTCNKQNDWYSQC------L |
| STCE1-5543 | CAAQRWAQCGGIGFSGCTTCVSGTTCNKQNDWYSQC------L |
| STCE1-5546 | CAAQRWAQCGGIGFSGCTTCVSGTTCNKQNDWYSQC------L |
| STCE1-5547 | CAAQRWAQCGGIGFSGCTTCVSGTTCNKQNDWYSQC------L |
| STCE1-5550 | CAAQRWAQCGGIGFSGCTTCVSGTTCNKQNDWYSQC------L |
| STCE1-5552 | CAAQRWAQCGGIGFSGCTTCVSGTTCNKQNDWYSQC------L |
| STCE1-5557 | CAAQRWAQCGGIGFSGCTTCVSGTTCNKQNDWYSQC------L |
| STCE1-5560 | CAAQRWAQCGGIGFSGCTTCVSGTTCNKQNDWYSQC------L |
| STCE1-5561 | CAAQRWAQCGGIGFSGCTTCVSGTTCNKQNDWYSQC------L |
| STCE1-5562 | CAAQRWAQCGGIGFSGCTTCVSGTTCNKQNDWYSQC------L |
| STCE1-5563 | CAAQRWAQCGGIGFSGCTTCVSGTTCNKQNDWYSQC------L |
| STCE1-5567 | CAAQRWAQCGGIGFSGCTTCVSGTTCNKQNDWYSQC------L |
| STCE1-5575 | CAAQRWAQCGGIGFSGCTTCVSGTTCNKQNDWYSQC------L |
| STCE1-5576 | CAAQRWAQCGGIGFSGCTTCVSGTTCNKQNDWYSQC------L |
| STCE1-5609 | CAAQRWAQCGGIGFSGCTTCVSGTTCNKQNDWYSQC------L |
| STCE1-5611 | CAAQRWAQCGGIGFSGCTTCVSGTTCNKQMDWYSQC------L |
| STCE1-5612 | CAAQRWAQCGGIGFSGCTTCVSGTTCNKQNDWYSQC------L |
| STCE1-5614 | CAAQRWAQCGGIGFSGCTTCVSGTTCNKQNDWYSQC------L |
| STCE1-5616 | CAAQRWAQCGGIGFSGCTTCVSGTTCNKQNDWYSQC------L |
| STCE1-5694 | CAAQRWAQCGGIGFSGCTTCVSGTTCNKQNDWYSQC------L |
| STCE1-5343 | CAAQRWAQCGGIGFSGCTTCVSGTTCNKQNDWYSQC------L |
| STCE1-5401 | CAAQRWAQCGGIGFSGCTTCVSGTTCNKQNDWYSQC------L |
| STCE1-5355 | CAAQRWAQCGGIGFSGCTTCVSGTTCNKQNDWYSQC------L |
| STCE1-5287 | CAAQRWAQCGGIGFSGCTTCVSGTTCNKQNDWYSQC------L |
| STCE1-5357 | CAAQRWAQCGGIGFSGCTTCVSGTTCNEQNDWYSQC------L |
| STCE1-5460 | CAAQRWAQCGGIGFSGCTTCVSGTTCNKQNDWYSQC------L |
| STCE1-5603 | CAAQRWAQCGGIGFSGCTTCVSGTTCNEQNDWYSQC------L |

FIG 4B

POLYPEPTIDES WITH ENDOGLUCANASE ACTIVITY AND USES THEREOF

This application is a Divisional of U.S. application Ser. No. 16/469,464, filed Jun. 13, 2019, which is a 371 of International Application No. PCT/US17/66267, filed Dec. 14, 2017, which claims the benefit of U.S. Application No. 62/435,340, filed Dec. 16, 2016, and Bangladesh Application No. 306/2106, filed Dec. 15, 2016, the entire content which is herein incorporated by reference in its entirety.

Disclosed herein are cellulase variants, or active fragments thereof, and polynucleotides encoding same, wherein the cellulase variants, or active fragments thereof, have endoglucanase activity. Also disclosed herein are compositions comprising said cellulase variants, or active fragments thereof, vectors and/or host cells comprising the polynucleotides encoding said cellulase variants, or active fragments thereof; and methods for making and/or using said cellulase variants, or active fragments thereof and/or compositions containing same; wherein said cellulase variants, or active fragments thereof, have endoglucanase activity.

REFERENCE TO SEQUENCE LISTING SUBMITTED ELECTRONICALLY

The content of the sequence listing electronically submitted with the application as an ASCII text file named 20210524_NB41187USPCD_SeqLst, created May 24, 2021 and having a size of 181 kilobytes and is filed concurrently with the specification. The sequence listing contained in this ASCII formatted document is part of the specification and is herein incorporated by reference in its entirety.

Cellulase enzymes are glycoside hydrolase enzymes that catalyze the hydrolysis of beta-1,4glycosidic linkages in cellulose to break it down into monosaccharides or shorter polysaccharides and oligosaccharides. Generally, cellulase enzymes contain a cellulose binding module (CBM) and a catalytic domain that are separated by a flexible spacer known as a "linker" or "linker peptide". The catalytic domains of cellulases are classified by both the Enzyme Commission (EC) and the Glycoside Hydrolase (GH) family systems.

The Enzyme Commission has identified two classes of cellulases, the endocellulases, which are classified as EC 3.2.1.4 enzymes and also referred to as endoglucanases, and the exocellulases, which are classified as EC 3.2.1.91 enzymes and also referred to as cellobiohydrolases or exoglucanase. The endoglucanases randomly cleave internal bonds at amorphous sites that create new chain ends, whereas the exoglucanases cleave two to four units from the ends of the exposed chains created by the endoglucanases. The GH family system, on the other hand, groups cellulases based on enzyme structure and function resulting in a number of GH Families including, for example, GH Family 5, 6, 7, 8, 9, 10, 12, 16, 18, 19, 26, 44, 45, 48, 51, 61, and 74.

Cellulases are known to be useful, for example, in detergent compositions; for treating textiles; as animal feed additives; in processing of paper and pulp for smoothing fiber, enhancing drainage and de-inking; in the food industry for extracting and clarifying juice from fruits and vegetables and for mashing; and in reducing biomass to glucose that is then fermented and distilled to make low C02 cellulosic ethanol.

Cellulases are used in the textile industry to improve the feel and/or appearance of cotton-containing fabric by, for example, removing fuzz (untangled fiber ends that protrude from the surface of yarn or fabric) and pills (bunches or balls of tangled fibers that are held to the surface of fabric by one or more fibers), and also helping to prevent pills, which make garments appear worn, from forming through subsequent consumer wash and wear cycles. This process is known as "depilling" or "biopolishing". Cellulases are also used to impart, for example, a distressed or "stonewashed" appearance to cotton-containing denim. This process is known as "bio-stoning" and has largely replaced stones for generating the soft, faded denim desired by consumers.

Cellulases are used in detergent compositions, for example, to enhance soil removal, remove pills, brighten fabric colors, and soften fabric. The detergent compositions to which cellulases are added also often contain other enzymes, such as, for example, proteases, making it important for the cellulase to be stable in the presence of these other enzymes, as well as, other detergent additives, such as, for example, surfactants. If the cellulase is not stable, the protease, for example, will degrade the cellulase over time negating the laundering benefits associated with the cellulase. As a result, there remains a need in the art for cellulases that are stable in the presence of one or more other enzyme, such as, for example, protease and/or one or more other detergent components, such as, for example, a surfactant.

DESCRIPTION OF THE DRAWINGS

FIGS. 2A-2H provide an alignment of the catalytic core region that was generated via a MUSCLE multiple sequence alignment of STCE-WT cellulase and variants thereof with other GH45 cellulases described in Example 4. The alignment provided includes the amino acid sequences of the following cellulases: STCE1-WT (SEQ ID NO:1), C_thermophilum (NCBI Accession NO: AGY80101.1, residues 1-293) (SEO ID NO: 70), H_insolens (NCBI Accession No: CAA01574.1, residues 22-305) (SEQ ID NO:71), H_grisea (NCBI Accession No: BAA74956.1, residues 22-305) (SEQ ID NO:72). T_terrestris (NCBI Accession No: XP 003651003.1, residues 22-299) (SEQ ID NO:73), A_thermophilum (accession No: ACE10216; SEQ ID NO:6 in U.S. Pat. No. 7,361,487, residues 22-315) (SEQ ID NO:74), N_crassa (NCBI Accession No: XP 957107, residues 22-293) (SEQ ID NO:75), and the cellulase variants listed on Table 1 (SEQ ID NOs: 7-68).

FIGS. 3A-3B provide an alignment of the linker region that was generated via a MUSCLE multiple sequence alignment of STCE-WT cellulase and variants thereof with other GH45 cellulases described in Example 4. The alignment provided includes the amino acid sequences of the following cellulases: STCE1-WT (SEQ ID NO:1), C_thermophilum (NCBI Accession NO: AGY80101.1, residues 1-293) (SEQ ID NO:70), H_insolens (NCBI Accession No: CAA01574.1, residues 22-305) (SEQ ID NO:71), H_grisea (NCBI Accession No: BAA74956.1, residues 22-305) (SEQ ID NO:72), T_terrestris (NCBI Accession No: XP 003651003.1, residues 22-299) (SEQ ID NO:73). A_thermophilum (accession No: ACE10216; SEQ ID NO:6 in U.S. Pat. No. 7,361,487, residues 22-315) (SEQ ID NO:74), N_crassa (NCBI Accession No: XP 957107, residues 22-293) (SEQ ID NO:75), and the cellulase variants listed on Table 1 (SEQ ID NOs: 7-68).

FIGS. 4A-4B provide an alignment of the C-terminal region that was generated via a MUSCLE multiple sequence alignment of STCE-WT cellulase and variants thereof with other GH45 cellulases described in Example 4. The alignment provided includes the amino acid sequences of the following cellulases: STCE1-WT (SEO ID NO: 1), C_thermophilum (NCBI Accession NO: AGY80101.1, residues 1-293) (SEQ ID NO:70), *H_insolens* (NCBI Accession No: CAA01574.1, residues 22-305) (SEQ ID NO:71), *H_grisea* (NCBI Accession No: BAA74956.1, residues 22-305) (SEQ ID NO:72), *T_terrestris* (NCBI Accession No: XP 003651003.1, residues 22-299) (SEQ ID NO:73). *A_thermophilum* (accession No: ACE10216: SEQ ID NO:6 in U.S. Pat. No. 7,361,487, residues 22-315) (SEQ ID NO:74), *N_crassa* (NCBI Accession No: XP 957107, residues 22-293) (SEQ ID NO:75), and the cellulase variants listed on Table 1 (SEQ ID NOs: 7-68).

Figure 2B:
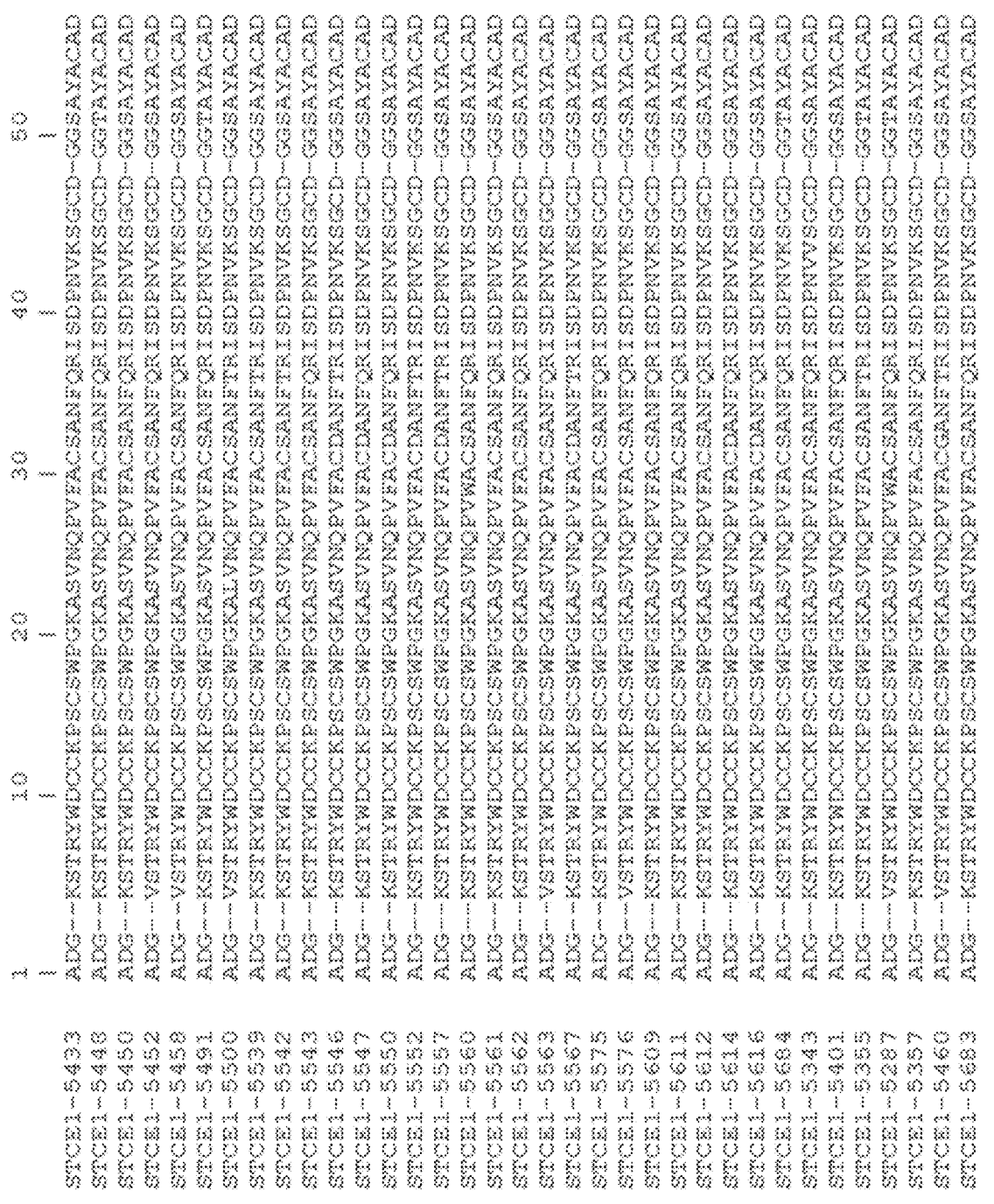
Figure 2C:
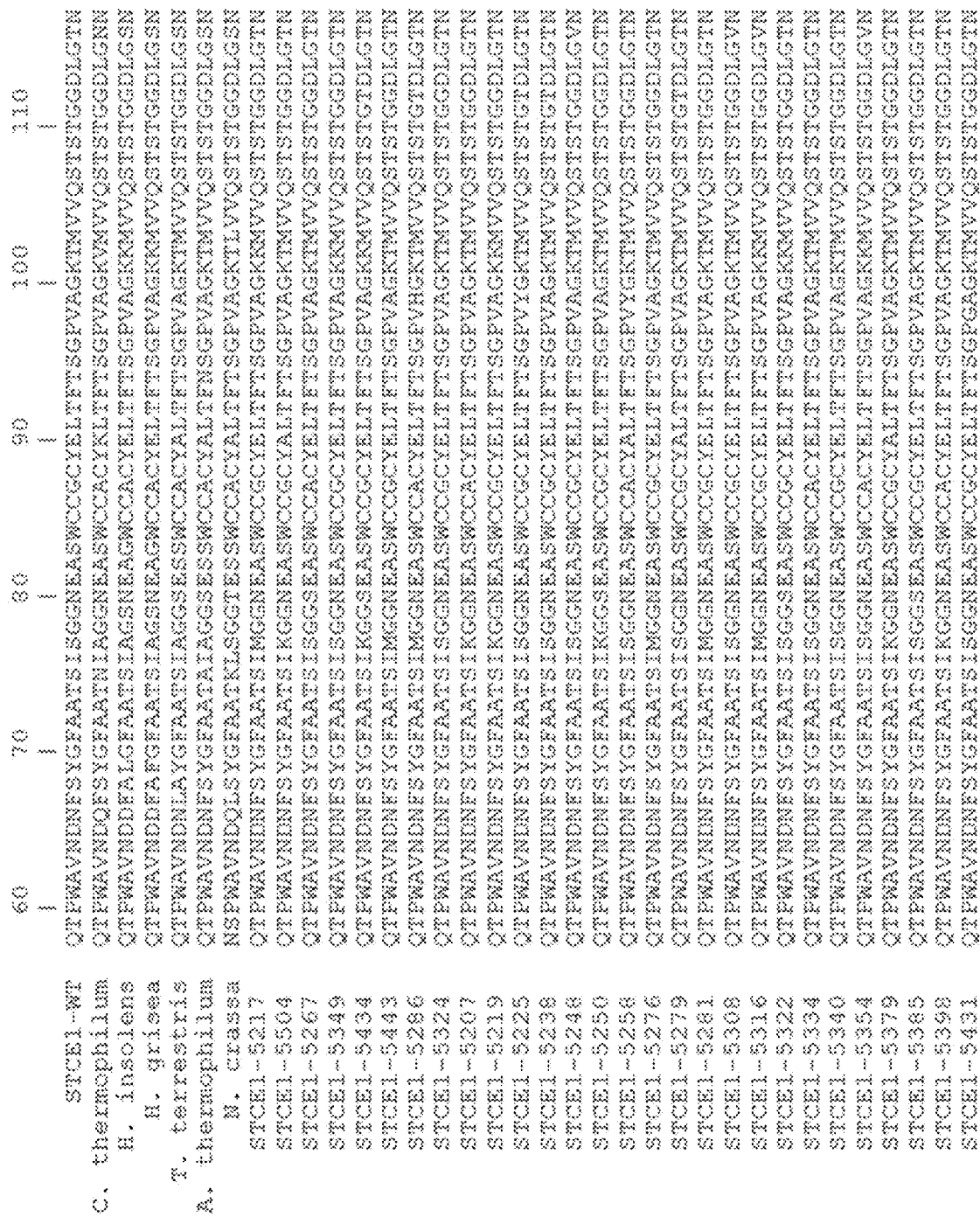
Figure 2D:
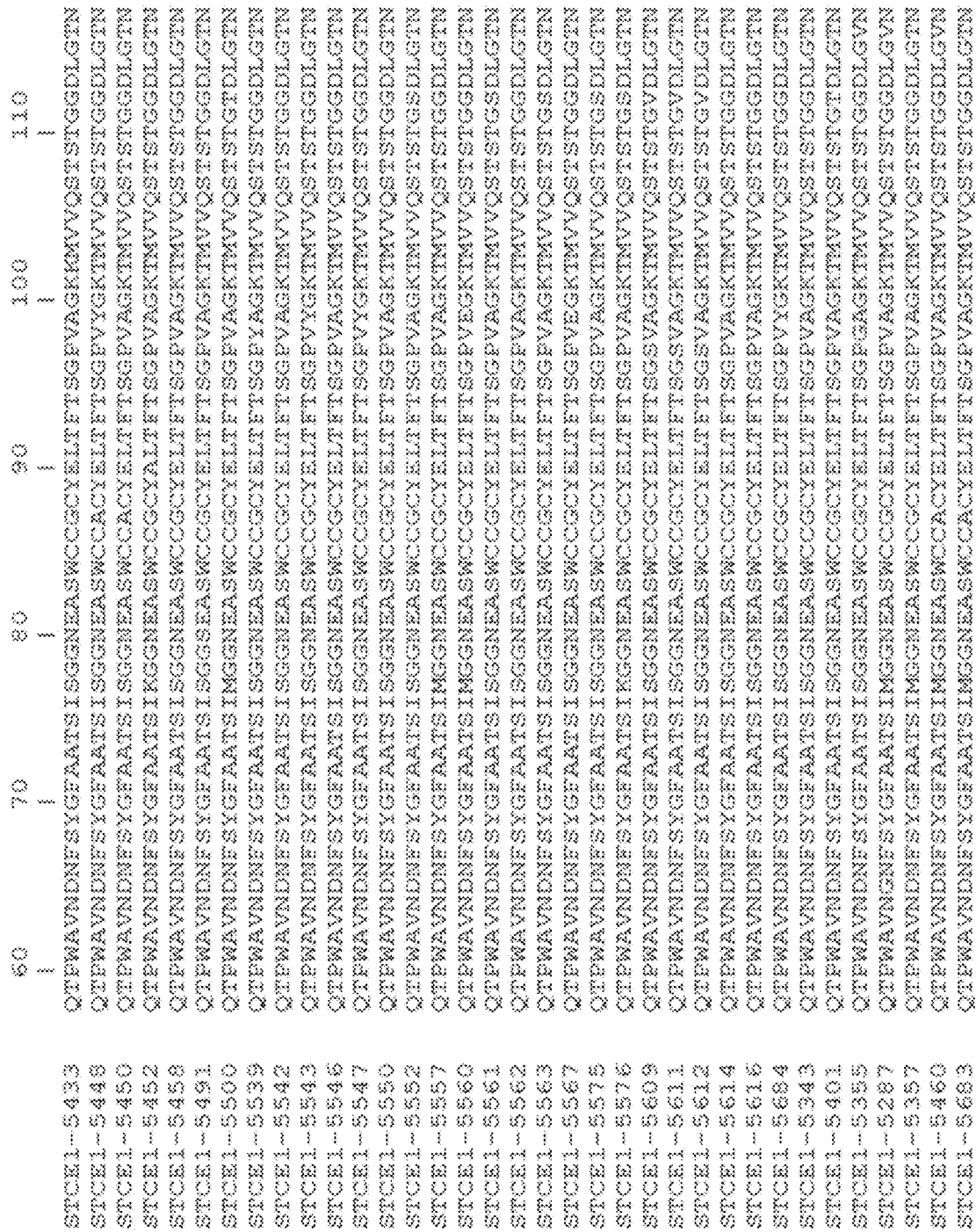
Figure 2E:
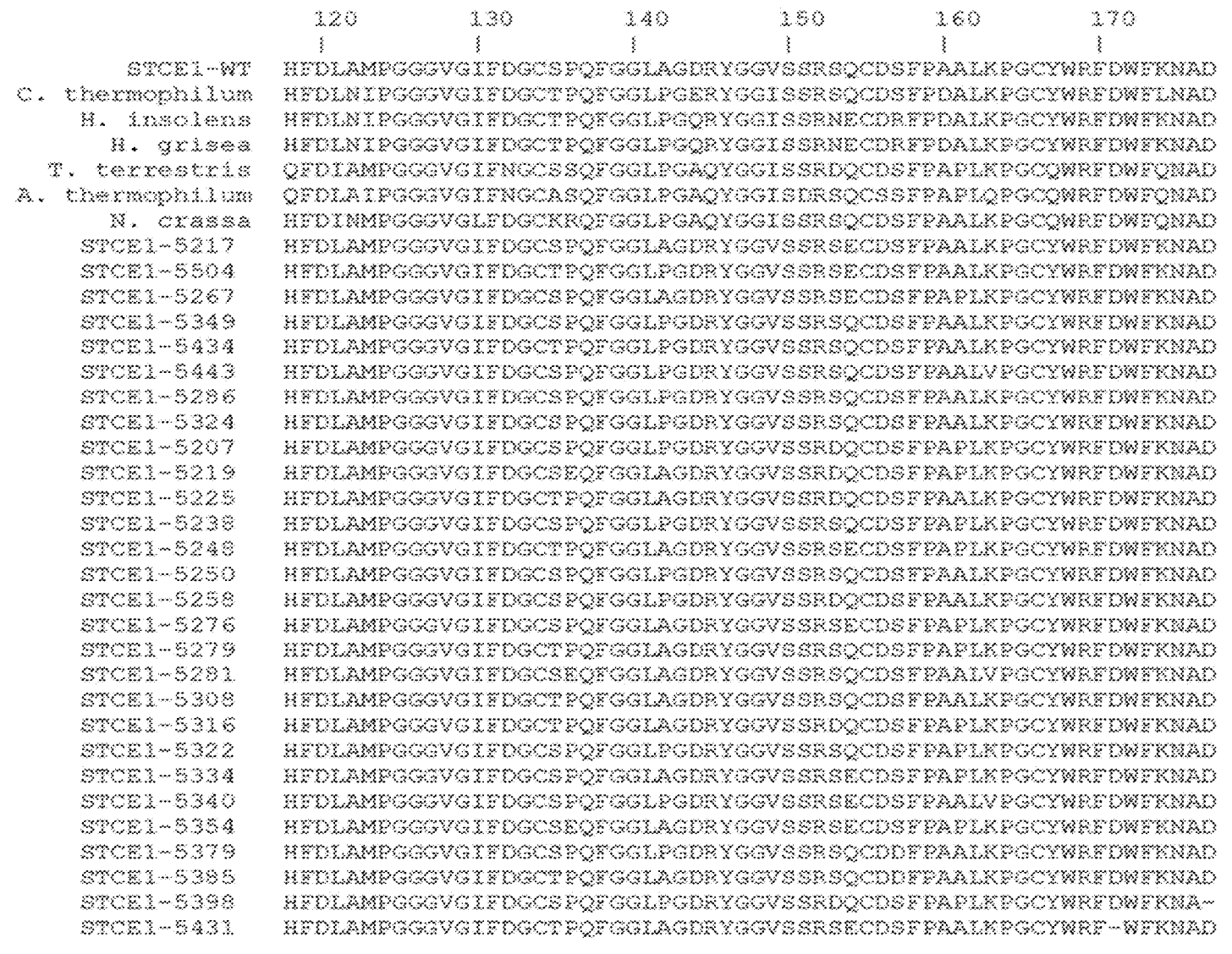
Figure 2G:
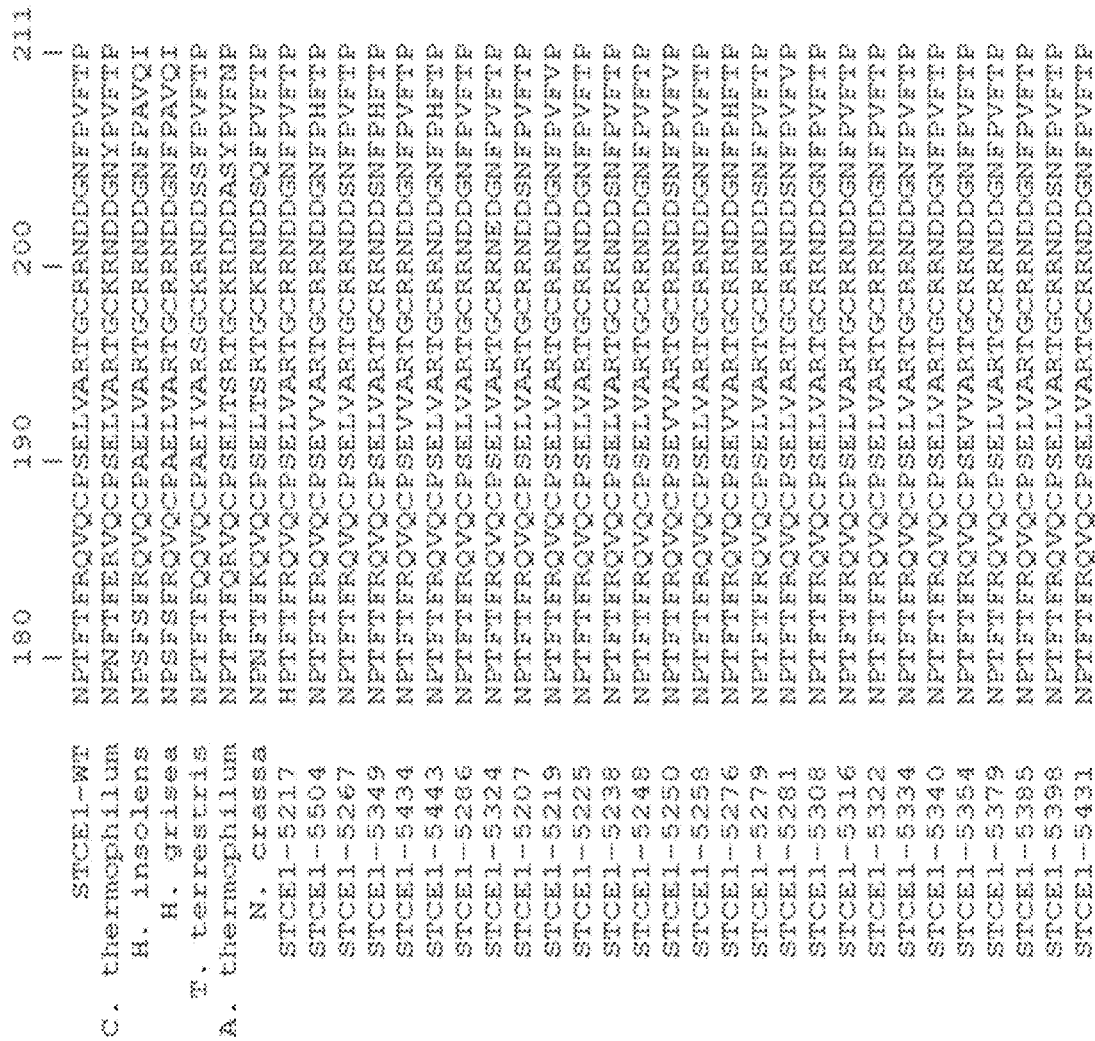

One embodiment is directed to a cellulase variant, or an active fragment thereof, comprising an amino acid sequence comprising two or more mutations at two or more positions corresponding to SEQ ID NO:1 positions selected from: (i) 4, 23, 29, 32, 34, 36, 44, 51, 65, 77, 80, 87, 90, 97, 98, 99, 102, 112, 116, 119, 135, 136, 142, 153, 154, 156, 157, 161, 163, 178, 192, 194, 202, 204, 205, 206, 208, 210, 212, 217, 221, 222, 225, 227, 232, 233, 236, 237, 238, 241, 247, 249, and 258; (ii) 4, 29, 32, 36, 51, 77, 80, 87, 90, 102, 112, 116, 135, 136, 142, 153, 154, 161, 163, 192, 204, 210, 217, 221, 225, and 227; (iii) 4V, 23L, 29W, 32D/G/Y, 34D, 36T, 44V, 51T, 65G, 77K/M, 80S, 87A, 90A, 97S, 98G/Y, 99E/H/Y, 102K, 112S/T/V, 116V, 119L, 135T, 136E/K/S, 142E/P, 153D, 154E, 156G, 157D, 161E/P, 163V, 178H, 192V, 194S, 202E, 204S, 205D, 206S, 208H/K, 210V, 212S, 217G/M, 221L/M, 222A, 225K, 227R, 232T, 233A/S, 236A, 237D, 238D, 241A/L/R, 247T, 249G/P, and 258K; (iv) 4V, 29W, 32D, 36T, 51T, 77K/M, 80S, 87A, 90A, 102K, 112S/T, 116V, 135T, 136E, 142P, 153D, 154E, 161P, 163V, 192V, 204S, 210V, 217G, 221L, 225K, and 227R; (v) K4, 523, F29, 532, N34, Q36, K44, S51, D65, S77, N80, G87, E90, P97, V98, A99, T102, G112, T116, F119, S135, P136, A142, S153, Q154, D156, S157, A161, K163, N178, L192, A194, D202, G204, N205, F206, V208, T210, P212, S217, S221, S222, 5225, K227, 5232, T233, T236, 5237, T238, T241, A247, S249, and G258; (vi) K4, F29, S32, Q36, S51, S77, N80, G87, E90, T102, G112, T116, S135, P136, A142, S153, Q154, A161, K163, L192, G204, T210, S217, S221, S225, and K227; (vii) K4V, S23L, F29W, S32D/G/Y, N34D, Q36T, K44V, S51T, D65G, S77K/M, N80S, G87A, E90A, P97S, V98G/Y, A99E/H/Y, T102K, G112S/T/V, T116V, F119L, S135T, P36E/K/S, A142E/P, S153D, Q154E, D156G, S157D, A161E/P, K163V, N178H, L192V, A194S, D202E, G204S, N205D, F206S, V208H/K, T210V, P212S, S217G/M, S221L/M, S222A, S225K, K227R, S232T, T233A/S, T236A, S237D, T238D, T241A/L/R, A247T, S249G/P, and G258K; or (viii) K4V, F29W, S32D, Q36T, S51T, S77K/M, N80S, G87A, E90A, T102K, G112S/T, T116V, S135T, P136E, A142P, S153D, Q154E, A161P, K163V, L192V, G204S, T210V, S217G, S221L, S225K, and K227R; wherein said variant has endoglucanase activity, and wherein the amino acid positions of the variant, or active fragment thereof, are numbered by correspondence with the amino acid sequence of SEQ ID NO:1. In other embodiments, one or more cellulase variant, or active fragment thereof, described herein comprises: (i) an amino acid sequence corresponding to position 1-295 of SEQ ID NO:1 and having at least 60%, 65%, 70%, 75%, 80%, 85%, 90%, 91%, 92%, 93%, 94%, 95%, 96%, 97%, 98%, 99%, or less than 100% amino acid sequence identity to the amino acid sequence of SEQ ID NO:1, 70, 71, 72, 73, 74, or 75; (ii) an amino acid sequence corresponding to position 1-211 of SEQ ID NO:1 and having at least 70%, 75%, 76%, 77%, 78%7, 79%, 80%, 81%, 82%, 83%, 84%, 85%, 86%, 87%, 88%, 89%0, 90%, 91%, 92%, 93%, 94%, 95%, 96%, 97%, 98%, 99%, or less than 100% amino acid sequence identity to an amino acid sequence as shown in positions 1-211 of SEQ ID NO:1, 70, 71, 72, 73, 74, or 75 set forth in FIG. 2; (iii) an amino acid sequence corresponding to position 212-258 of SEQ ID NO:1 and having at least 70%, 75%, 80%, 90%, 91%, 92%, 93%, 94%, 95%, 96%, 97%, 98%, 99%, or 100% amino acid sequence identity to an amino acid sequence as shown in positions 212-258 of SEQ ID NO:1, 70, 71, 72, 73, 74, or 75 set forth in FIG. 3; and/or (iv) an amino acid sequence corresponding to position 259-295 of SEQ ID NO:1 and having at least 60%, 67%, 68%, 70%, 73%, 75%, 76%, 80%, 81%, 83%, 84%, 90%, 91%, 92%, 93%, 94%, 95%, 96%, 97%, 98%, 99%, or 100% amino acid sequence identity to an amino acid sequence as shown in positions 259-295 of SEQ ID NO:1, 70, 71, 72, 73, 74, or 75 set forth in FIG. 4. In another embodiment, the cellulase variant, or active fragment thereof is derived from a parent or reference polypeptide selected from SEQ ID NOs: 1, 70, 71, 72, 73, 74, and 75. In still yet another embodiment, the cellulase variant, or active fragment thereof is a family GH45 cellulase.

In one embodiment, the cellulase variant, or active fragment thereof, has one or more improved property selected from improved thermostability, improved stability in the presence of one or more other enzyme, and improved stability in the presence of one or more other enzyme and one or more other detergent component. In another embodiment, the other enzyme is protease and/or the other detergent component is a surfactant. In some embodiments, the improved property is improved when compared to the parent or reference polypeptide.

A further embodiment is directed to a composition comprising said cellulase variant, or active fragment thereof; a vector and/or host cell comprising said cellulase variant, or active fragment thereof, and a method for making and/or using said variant, or active fragment thereof and/or said compositions containing such variants, or active fragments thereof; wherein said cellulase variant, or active fragment thereof, has endoglucanase activity.

The features of the cellulase variants described herein make them well-suited for use in detergent compositions, textile processing, paper and pulp processing, and other industrial applications, such as, for example, to impart soil release or fabric care benefits and/or improve the feel and/or appearance of a cotton-containing fabric.

The following terms are defined for clarity. Terms not defined should be accorded their ordinary meaning as used in the art. For example, technical and scientific terms not defined herein have the same meaning as commonly understood by one of ordinary skill in the art (See, e.g., Singleton and Sainsbury, *Dictionary of Microbiology and Molecular Biology*, 2d Ed., John Wiley and Sons, NY 1994; and Hale and Marham, *The Harper Collins Dictionary of Biology*, Harper Perennial, NY 1991).

The singular terms "a," "an," and "the" include the plural reference unless the context clearly indicates otherwise.

The term "about" when used in connection with a numerical value refers to a range of −10% to +10% of the numerical value. For instance, the phrase a "pH value of about 6" refers to pH values of from 5.4 to 6.6.

The term "adjunct ingredient" when used in conjunction with a detergent or fabric care composition means any liquid, solid or gaseous material selected for the particular type of detergent or fabric care composition desired and the form of the product (e.g., liquid, granule, powder, bar, paste, spray, tablet, gel, unit dose, sheet, or foam composition), which materials are also preferably compatible with the cellulase variant or active fragment thereof used in the composition. In some embodiments, granular compositions are in "compact" form, while in other embodiments, the liquid compositions are in a "concentrated" form.

The term "cellulase variant" refers to a recombinant polypeptide that is derived from a parent or reference polypeptide by the substitution, addition, or deletion, of one or more amino acids. A cellulase variant may differ from a parent polypeptide by a small number of amino acid residues and may be defined by their level of primary amino acid sequence homology/identity with a parent polypeptide. For example, a cellulase variant has at least 60%, 65%, 70%, 75%, 80%, 85%, 90%, 91%, 92%, 93%, 94%, 95%, 96%, 97%, 98%, 99%, or less than 100% amino acid sequence identity with a parent (or reference) polypeptide.

The term "mutation" refers to any change or alteration in an amino acid sequence, including the substitution of an amino acid at the identified position of an amino acid sequence with an amino acid that is different from the starting amino acid, deletion of an amino acid at the identified position of an amino acid sequence, insertion of an amino acid at the identified position of an amino acid sequence, replacement of an amino acid side chain in an amino acid sequence, and or chemical modification of an amino acid sequence.

The terms "detergent composition" and "detergent formulation" refer to mixtures of chemical ingredients intended for use in a wash medium to clean soiled objects. Detergent compositions/formulations may include, for example, one or more surfactant, hydrolytic enzyme, oxido-reductase, builder, bleaching agent, bleach activator, bluing agent, fluorescent dye, caking inhibitor, masking agent, enzyme activator, antioxidant, chelant, polymer, foam regulator, fragrance, and solubilizer.

The term "derived from" encompasses the terms "originated from," "obtained from," "obtainable from," "isolated from," and "created from" and generally indicates that one specified material find its origin in another specified material or has features that can be described with reference to the another specified material.

The term "effective amount" when used in conjunction with a cellulase variant or active fragment thereof refers to the quantity of cellulase variant or active fragment thereof needed to achieve the desired level of endoglucanase activity in the specified application or detergent or fabric care composition. Such effective amounts are readily ascertained by one of ordinary skill in the art and are based on many factors, such as the particular cellulase variant or active fragment thereof that is used, the application, the specific composition of the cleaning composition (including the particular protease contained therein), and whether a liquid or dry (e.g., granular, bar, powder, solid, liquid, tablet, gel, paste, foam, sheet, or unit dose) composition is required.

The term "endoglucanase" refers to an endo-1,4-(1,3;1, 4)-beta-D-glucan 4-glucanohydrolase (E.C. 3.2.1.4), which catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined according to the procedure described in the examples.

The term "expression vector" refers to a DNA construct containing a DNA sequence that encodes the specified polypeptide and is operably linked to a suitable control sequence capable of effecting the expression of the polypeptides in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself.

The term "fabric" refers to, for example, woven, knit, and non-woven material, as well as staple fibers and filaments that can be converted to, for example, yarns and woven, knit, and non-woven fabrics. The term encompasses material made from natural, as well as synthetic (e.g., manufactured) fibers.

The terms "fabric care composition" or "fabric care formulation" refer to a composition/formulation containing a cellulase variant, or active fragment thereof, described herein that will, when added to a wash medium, remove pills and/or fuzz from fabric; brighten fabric colors; and/or soften fabric.

The term "family GH45" refers to a polypeptide that is classified as glycoside hydrolase Family 45 according to Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696 and classified based on structure and function relationships CMin the Carbohydrate-Active enZYmes Database, CAZy (URL: http://afmb.cnrs-mrs.fr/~cazy/CAZY/index.html).

The term "host cells" generally refers to prokaryotic or eukaryotic hosts which are transformed or transfected with vectors constructed using recombinant DNA techniques known in the art. Transformed host cells are capable of either replicating vectors encoding the protein variants or expressing the desired protein variant. In the case of vectors which encode the pre- or pro-form of the protein variant, such variants, when expressed, are typically secreted from the host cell into the host cell medium.

The term "hybridization" refers to the process by which a strand of nucleic acid joins with a complementary strand through base pairing, as known in the art.

The term "hybridization conditions" refers to the conditions under which hybridization reactions are conducted. These conditions are typically classified by degree of "stringency" of the conditions under which hybridization is measured. The degree of stringency can be based, for example, on the melting temperature ($T_m$) of the nucleic acid binding complex or probe. For example, "maximum stringency" typically occurs at about $T_m$–5° C. (5° below the $T_m$ of the probe); "high stringency" at about 5-10° C. below the $T_m$; "intermediate stringency" at about 10-20° C. below the $T_m$ of the probe; and "low stringency" at about 20-25° C. below the $T_m$. Alternatively, or in addition, hybridization conditions can be based upon the salt or ionic strength conditions of hybridization and/or one or more stringency washes, e.g., 6×SSC=very low stringency; 3×SSC=low to medium stringency; 1×SSC=medium stringency; and 0.5×SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe. For applications requiring high selectivity, it is typically desirable to use relatively stringent conditions to form the hybrids (e.g., relatively low salt and/or high temperature conditions are used).

The term "introduced" in the context of inserting a nucleic acid sequence into a cell, means transformation, transduction, or transfection. Means of transformation include protoplast transformation, calcium chloride precipitation, electroporation, naked DNA, and the like as known in the art. (See, Chang and Cohen [1979] *Mol. Gen. Genet.* 168:111-115; Smith et al. [1986] *Appl. Env. Microbiol.* 51:634; and the review article by Ferrari et al., in Harwood, *Bacillus*, Plenum Publishing Corporation, pp. 57-72, 1989).

A nucleic acid or polynucleotide is "isolated" when it is at least partially or completely separated from other components, including but not limited to, for example, other proteins, nucleic acids, and cells. Similarly, a polypeptide, protein or peptide is "isolated" when it is at least partially or completely separated from other components, including but not limited to, for example, other proteins, nucleic acids, and cells. On a molar basis, an isolated species is more abundant than are other species in a composition. For example, an isolated species may comprise at least about 60%, 65%, 70%, 75%, 80%, 85%, 90%, 91%, 92%, 93%, 94%, 95%, 96%, 97%, 98%, 99%, or 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a nucleic acid or a protein sample, respectively, followed by visualization upon staining. If desired, a high-resolution technique, such as high performance liquid chromatography (HPLC) or a similar means can be utilized for purification of the material. The term "other detergent component" refers to a non-enzyme component that is added to a detergent composition or formulation, such as, for example, a surfactant, oxido-reductase, builder, bleaching agent, bleach activator, bluing agent, fluorescent dye, caking inhibitor, masking agent, enzyme activator, antioxidant, chelant, polymer, foam regulator, fragrance, and solubilizer.

The term "other enzyme" refers to a second, third, fourth, etc enzyme that is added to a detergent composition, wherein the first enzyme is a cellulase variant, or active fragment thereof described herein. Examples of other enzymes include, for example, acyl transferases, amylases, alpha-amylases, beta-amylases, alpha-galactosidases, arabinases, arabinosidases, aryl esterases, beta-galactosidases, beta-glucanases, carrageenases, catalases, chondroitinases, cutinases, endo-beta-mannanases, exo-beta-mannanases, esterases, exo-mannanases, galactanases, glucoamylases, hemicellulases, hyaluronidases, keratinases, laccases, lactases, ligninases, lipases, lipolytic enzymes, lipoxygenases, mannanases, metalloproteases, oxidases, oxidoreductases, pectate lyases, pectin acetyl esterases, pectinases, pentosanases, perhydrolases, peroxidases, phenoloxidases, phosphatases, phospholipases, phytases, polyesterases, polygalacturonases, proteases, pullulanases, reductases, rhamnogalacturonases, second cellulase, beta-glucanases, tannases, transglutaminases, xylan acetyl-esterases, xylanases, xylosidases, and combinations thereof.

The terms "polynucleotide" encompasses DNA, RNA, heteroduplexes, and synthetic molecules capable of encoding a polypeptide. Nucleic acids may be single-stranded or double-stranded, and may have chemical modifications. The terms "nucleic acid" and "polynucleotide" are used interchangeably. Because the genetic code is degenerate, more than one codon may be used to encode a particular amino acid, and the present compositions and methods encompass nucleotide sequences which encode a particular amino acid sequence. Unless otherwise indicated, nucleic acid sequences are presented in a 5'-to-3' orientation.

The term "polypeptide" refers to a molecule comprising a plurality of amino acids linked through peptide bonds. The terms "polypeptide," "peptide," and "protein" are used interchangeably. Proteins may optionally be modified (e.g., glycosylated, phosphorylated, acylated, farnesylated, prenylated, and sulfonated) to add functionality. Where such amino acid sequences exhibit activity, they may be referred to as an "enzyme". The conventional one-letter or three-letter codes for amino acid residues are used, with amino acid sequences being presented in the standard amino-to-carboxy terminal orientation (i.e., N→C).

The term "recombinant," refers to genetic material (i.e., nucleic acids, the polypeptides they encode, and vectors and cells comprising such polynucleotides) that has been modified to alter its sequence or expression characteristics, such as, for example, by mutating the coding sequence to produce an altered polypeptide, fusing the coding sequence to that of another gene, placing a gene under the control of a different promoter, expressing a gene in a heterologous organism, expressing a gene at a decreased or elevated level, and expressing a gene conditionally or constitutively in manner different from its natural expression profile. Generally recombinant nucleic acids, polypeptides, and cells based thereon, have been manipulated by man such that they are not identical to related nucleic acids, polypeptides, and/or cells found in nature.

The term "second cellulase" refers to a second cellulase enzyme that is added to a detergent composition, wherein the first cellulase enzyme is a cellulase variant, or active fragment thereof described herein. This second cellulase enzyme, includes, for example, cellobiohydrolases, endoglucanases, xyloglucanases, and combinations thereof.

The term "signal sequence" refers to a sequence of amino acids bound to the N-terminal portion of a polypeptide, and which facilitates the secretion of the mature form of the protein from the cell. The mature form of the extracellular protein lacks the signal sequence which is cleaved off during the secretion process.

The term "surfactant" refers to any compound generally recognized in the art as having surface active qualities. Surfactants can include, for example, anionic, cationic, nonionic, and zwitterionic compounds, which are further described, herein.

The terms "thermostability" and "thermostable" refer to cellulase variants that retain a specified amount of endoglucanase activity after exposure to elevated temperatures over a given period of time under conditions prevailing during cleaning, textile treatment, or other process, for example, while exposed to elevated temperatures. In some embodiments, the one or more cellulase variant retains at least about 50%, about 60%, about 70%, about 75%, about 80%, about 85%, about 90%, about 92%, about 95%, about 96%, about 97%, about 98%, or about 99% endoglucanase activity after exposure to elevated temperatures, for example, at least about 50° C., about 55° C., about 60° C., about 65° C., or about 70° C., over a given time period, for example, at least about 10 minutes, about 30 minutes, about 60 minutes, about 120 minutes, about 180 minutes, about 240 minutes, about 300 minutes, etc.

The term "variant polynucleotide" refers to a polynucleotide that encodes a cellulase variant, has a specified degree of homology/identity with a parent polynucleotide, or hybridizes under stringent conditions to a parent polynucleotide or the complement, thereof. For example, a variant polynucleotide has at least 70%, 75%, 80%, 81%, 82%, 83%, 84%, 85%, 86%, 87%, 88%, 89%, 89%, 90%, 91%, 92%, 93%, 94%, 95%, 96%, 97%, 98%, or 99% nucleotide sequence identity with a parent polynucleotide.

The terms, "wild-type" or "parental" with respect to a polypeptide, refer to a naturally-occurring polypeptide that does not include a man-made substitution, insertion, or deletion at one or more amino acid positions. Similarly, the terms "wild-type" or "parental,", with respect to a polynucleotide, refer to a naturally-occurring polynucleotide that does not include a man-made substitution, insertion, or deletion at one or more nucleosides. A polynucleotide encoding a wild-type or parental polypeptide is, however, not limited to a naturally-occurring polynucleotide, and encompasses any polynucleotide encoding the wild-type or parental polypeptide.

The term "naturally-occurring" refers to, for example, a sequence and residues contained therein (e.g., polypeptide sequence and amino acids contained therein or nucleic acid sequence and nucleic acids contained therein) that are found in nature. Conversely, the term "non-naturally occurring" refers to, for example, a sequence and residues contained therein (e.g., polypeptide sequences and amino acids contained therein or nucleic acid sequence and nucleic acids contained therein) that are not found in nature.

The term "reference", with respect to a polypeptide, refers to a naturally-occurring polypeptide that does not include a man-made substitution, insertion, or deletion at one or more amino acid positions, as well as a naturally-occurring or synthetic polypeptide that includes one or more man-made substitutions, insertions, or deletions at one or more amino acid positions. Similarly, the term "reference", with respect to a polynucleotide, refers to a naturally-occurring polynucleotide that does not include a man-made substitution, insertion, or deletion of one or more nucleosides, as well as a naturally-occurring or synthetic polynucleotide that includes one or more man-made substitutions, insertions, or deletions at one or more nucleosides. For example, a polynucleotide encoding a wild-type or parental polypeptide is not limited to a naturally-occurring polynucleotide, and encompasses any polynucleotide encoding the wild-type or parental polypeptide.

The amino acid substitutions described herein use one or more following nomenclatures: position or starting amino acid:position:substituted amino acid(s). Reference to only a position encompasses any starting amino acid that may be present in a reference polypeptide, parent or wild-type molecule at that position and any amino acid with which such starting amino acid may be substituted (i.e., amino acid substitutions exclude the starting amino acid of such reference polypeptide, parent or wild-type molecule). Reference to a substituted amino acid or a starting amino acid may be further expressed as several substituted amino acids or several starting amino acids separated by a foreslash ("/"). For example, X130AJN-209-213 represents a three amino acid substitution combination, wherein X is any starting amino acid at position 130 that can be substituted with an alanine (A) or an asparagine (N); 209 represents a position where any starting amino acid can be substituted with an amino acid that is not the starting amino acid; and 213 represents a position where any starting amino acid can be substituted with an amino acid that is not the starting amino acid. By way of further example, E/Q/S101F/G/H/T/V represents five possible substitutions at position 101, wherein the starting amino acid glutamate (E), glutamine (Q), or serine (S) can be substituted with a phenylalanine (F), glycine (G), histidine (H), threonine (T), or valine (V).

The one letter code "Z" identifies an insertion or deletion in a parent or reference amino acid sequence. For an insertion relative to the parent or reference sequence, the one letter code "Z" is on the left side of the position number and further includes a number (e.g., 0.01) before each amino acid being inserted therein to indicate the order of the insertions. For example, the insertion of a one amino acid, glutamine (Q), at position 298 would be depicted as "Z298.01Q"; the insertion of one amino acid, X (where X can be any amino acid) at position 298 would be depicted as "Z298.01X"; and the insertion of three amino acids alanine (A), serine (S) and tyrosine (Y) between position 87 and 88 would be depicted as "Z87.01A/Z87.02S/Z87.03Y". For a deletion, the one letter code "Z" is on the right side of the position number. For example, the deletion of an alanine (A) from position 100 would be depicted as A100Z. A combination of some the above insertions and deletions would be depicted as: "G87S/Z87.01A/Z87.02S/Z87.03Y/A100Z".

Sequence identity may be determined using known programs such as BLAST, ALIGN, and CLUSTAL using standard parameters. (See, e.g., Altschul et al. [1990] *J. Mol. Biol.* 215:403-410; Henikoff et al. [1989] *Proc. Natl. Acad. Sci. USA* 89:10915; Karin et al. [1993] *Proc. Natl. Acad. Sci USA* 90:5873; and Higgins et al. [1988] *Gene* 73:237-244). Software for performing BLAST analyses is publicly available through the National Center for Biotechnology Information (NCBI). Databases may also be searched using FASTA (Pearson et al. [1988] *Proc. Natl. Acad. Sci. USA* 85:2444-2448). One indication that two polypeptides are substantially identical is that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, where the two peptides differ only by a conservative substitution. Another useful algorithm for comparison of multiple protein sequences is the MUSCLE program (Robert C. Edgar. MUSCLE: multiple sequence alignment with high accuracy and high throughput Nucl. Acids Res. (2004) 32 (5): 1792-1797) accessed from Geneious software (Biomatters Ltd.).

One embodiment is directed to a cellulase variant, or an active fragment thereof, comprising an amino acid sequence comprising two or more mutations at two or more positions corresponding to SEQ ID NO:1 positions selected from: (i) 4, 23, 29, 32, 34, 36, 44, 51, 65, 77, 80, 87, 90, 97, 98, 99, 102, 112, 116, 119, 135, 136, 142, 153, 154, 156, 157, 161, 163, 178, 192, 194, 202, 204, 205, 206, 208, 210, 212, 217, 221, 222, 225, 227, 232, 233, 236, 237, 238, 241, 247, 249, and 258; (ii) 4, 29, 32, 36, 51, 77, 80, 87, 90, 102, 112, 116, 135, 136, 142, 153, 154, 161, 163, 192, 204, 210, 217, 221, 225, and 227; (iii) 4V, 23L, 29W, 32D/G/Y, 34D, 36T, 44V, 51T, 65G, 77K/M, 80S, 87A, 90A, 97S, 98G/Y, 99E/H/Y, 102K, 112S/T/V, 116V, 119L, 135T, 136E/K/S, 142E/P, 153D, 154E, 156G, 157D, 161E/P, 163V, 178H, 192V, 194S, 202E, 204S, 205D, 206S, 208H/K, 210V, 212S, 217G/M, 221L/M, 222A, 225K, 227R, 232T, 233A/S, 236A, 237D, 238D, 241A/L/R, 247T, 249G/P, and 258K; (iv) 4V, 29W, 32D, 36T, 51T, 77K/M, 80S, 87A, 90A, 102K, 112S/T, 116V, 135T, 136E, 142P, 153D, 154E, 161P, 163V, 192V, 204S, 210V, 217G, 221L, 225K, and 227R; (v) K4, S23, F29, S32, N34, Q36, K44, S51, D65, S77, N80, G87, E90, P97, V98, A99, T102, G112, T116, F119, S135, P136, A142, S153, Q154, D156, S157, A161, K163, N178, L192, A194, D202, G204, N205, F206, V208, T210, P212, 5217, 5221, S222, S225, K227, S232, T233, T236, S237, T238, T241, A247, S249, and G258; (vi) K4, F29, S32, Q36, 551, S77, N80, G87, E90, T102, G112, T116, S135, P136, A142, S153, Q154, A161, K163, L192, G204, T210, S217, S221, S225, and K227; (vii) K4V, S23L, F29W, S32D/G/Y, N34D, Q36T, K44V, S51T, D65G, S77K/M, N80S, G87A, E90A, P97S, V98G/Y, A99E/H/Y, T102K, G112S/T/V, T116V, F119L, S135T, P36E/K/S, A142E/P, S153D, Q154E, D156G, S157D, A161E/P, K163V, N178H, L192V, A194S, D202E, G204S, N205D, F206S, V208H/K, T210V, P212S, S217G/M, S221L/M, S222A, S225K, K227R, S232T, T233A/S, T236A, S237D, T238D, T241A/L/R, A247T, S249G/P, and G258K; or (viii) K4V, F29W, S32D, Q36T, S51T, S77K/M, N80S, G87A, E90A, T102K, G112S/T, T116V, S135T, P136E, A142P, S153D, Q154E, A161P, K163V, L192V, G204S, T210V, S217G, S221L, S225K, and K227R; wherein said variant has endoglucanase activity, and wherein the amino acid positions of the variant, or active fragment thereof, are numbered by correspondence with the amino acid sequence of SEQ ID NO:1. Another embodiment is directed to a cellulase variant, or active fragment thereof, comprising an amino acid sequence comprising two or more mutations at two or more positions corresponding to SEQ ID NO:1 positions selected from: (i) 142+161, 4+142, 36+142, 4+77, 77+142, 87+142, 87+161, 142+204, 4+161, 161+204, 102+161, 142+192, 142+227, 153+161, 4+102, 4+210, 29+153, 32+142, 36+161, 36+221, 36+225, 87+204, 90+142, 116+161, 135+142, 135+154, 135+161, 136+161, 204+221, 4V+80S, 4+153, 4+221, 32+36, 32+142, 77+142, 77+153, 77+161, 77+221, 80+142, 87+153, 87+192, 87+221, 102+136, 102+142, 102+154, 112+135, 112+142, 142+153, 142+217, 142+221, 153+210, 154+161, 161+192, and 161+221; (ii) 142P+161P, 4V+142P, 36T+142P, 4V+77K, 77K+142P, 87A+142P, 87A+161P, 142P+204S, 4V+161P, 161P+204S, 102K+161P, 142P+192V, 142P+227R, 153D+161P, 4V+102K, 4V+210V, 29W+153D, 32D+142P, 36T+161P, 36T+221L, 36T+225K, 87A+204S, 90A+142P, 116V+161P, 135T+142P, 135T+154E, 135T+161P, 136E+161P, 204S+221L, 4V+80S, 4V+153D, 4V+221L, 32D+36T, 32Y+142P, 77M+142P, 77K+153D, 77K+161P, 77K+221L, 80S+142P, 87A+153D, 87A+192V, 87A+221L, 102K+136E, 102K+142P, 102K+154E, 112T+135T, 112S+142P, 142P+153D, 142P+217G, 142P+221L, 153D+210V, 154E+161P, 161P+192V, and 161P+221L; or (iii) A142P+A161P, K4V+A142P, Q36T+A142P, K4V+S77K, S77K+A142P, G87A+A142P, G87A+A161P, A142P+G204S, K4V+A161P, A161P+G204S, T102K+A161P, A142P+L192V, A142P+K227R, S153D+A161P, K4V+T102K, K4V+T210V, F29W+S153D, S32D+A142P, Q36T+A161P, Q36T+S221L, Q36T+S225K, G87A+G204S, E90A+A142P, T116V+A161P, S135T+A142P, S135T+Q154E, S135T+A161P, P136E+A161P, G204S+S221L, K4V+N80S, K4V+S153D, K4V+S221L, S32D+Q36T, S32Y+A142P, S77M+A142P, S77K+S153D, S77K+A161P, S77K+S221L, N80S+A142P, G87A+S153D, G87A+L192V, G87A+S221L, T102K+P136E, T102K+A142P, T102K+Q154E, G112T+S135T, G112S+A142P, A142P+S153D, A142P+S217G, A142P+S221L, S153D+T210V, Q154E+A161P, A161P+L192V, and A161P+S221L; wherein said variant has endoglucanase activity, and wherein the amino acid positions of the variant, or active fragment thereof, are numbered by correspondence with the amino acid sequence of SEQ ID NO:1. A still further embodiment is directed to a cellulase variant, or active fragment thereof, comprising an amino acid sequence comprising two or more mutations at two or more positions corresponding to SEQ ID NO:1 positions selected from: K4V-Q36T-S77M-T102K-Q154E-N178H-S225K-S232Z-T233Z-S234Z-T235Z-T236Z-S237Z-T238Z-K239Z-A240Z-T241Z-S242Z-T243Z, K4V-K44V-S77K-E90A-S135T-A142P-Q154E-L192V-V208H-S221L-S232Z-T233Z-S234Z-T235Z-T236Z-S237Z-T238Z-K239Z-A240Z-T241Z-S242Z-T243Z-A247T, K4V-N80S-G87A-Q154E-A161P-G204S-S221L-T233Z-S234Z-T235Z-T236Z-S237Z-T238Z-K239Z-A240Z-T241Z-S242Z-T243Z, S32Y-T102K-A142P-G204S-V208H-T233Z-S234Z-T235Z-T236Z-S237Z-T238Z-K239Z-A240Z-T241Z-S242Z-T243Z-A247T, K4V-K44V-S77K-N80S-T102K-G112T-S135T-A142P-L192V-T233Z-S234Z-T235Z-T236Z-S237Z-T238Z-K239Z-A240Z-T241Z-S242Z-T243Z, S77M-A142P-K163V-V208H-T233Z-S234Z-T235Z-T236Z-S237Z-T238Z-K239Z-A240Z-T241Z-S242Z-T243Z-A247T, S77M-G87A-A99H-G112T-A142P-S232T-T233Z-T236A, S23L-A142P-D202E-S232T-T233Z, Q36T-S77K-G87A-A142P-S153D-A161P-G204S-S221L-S237D, K4V-F29W-S77K-T102K-P136E-S153D-A161P-T210V, A99Y-G112T-S135T-S153D-K227R, S23L-S32Y-G112T-A142P-A161P-G204S-S217G-K227R-S237D, F29W-Q36T-K44V-T116V-S135T-Q154E-A161P-S217G-S221L-S225K-T238D, K4V-Q36T-S77K-N80S-A142P-L192V-G204S-T210V-S221L, F29W-G87A-E90A-A99Y-A142P-S153D-K227R-S237D, K4V-S77M-Q154E-A161P-L192V-V208H-S217G-T233A-S237D, E90A-G112T-S135T-A161P-G204S, S51T-S77M-P136E-K163V-G204S-T210V-K227R, K4V-F29W-S51T-T116V-S135T-S221L-S225K, S77M-T102K-T116V-S135T-S153D-A161P-T238D, K4V-S23L-S32Y-N80S-T102K-A142P-A161P-S237D, K44V-G87A-Q154E-A161P, S32Y-A142P-Q154E-K163V-S217G-K227R-T233A, N34D-S51T-G87A-T102K-T116V-P136E-Q154E-A161P-L192V-T233A-T238D, K4V-S77K-E90A-A142P-S157D-G214Z-S217G-T233A-T238D, K4V-Q36T-S51T-N80S-S135T-S157D-T233A, K4V-S51T-V98G-S135T-Q154E-T233A, T102K-A142P-Q154E-G204S-K227R, S51T-G87A-A99Y-S135T-N205D-T238D, G87A-A142P-A161P-L192V-G204S-T241A, K4V-S77K-E90A-A142P-S157D-S217G-T233A-T238D, K4V-P136E-S153D-A161P-T210V-K227R, S51T-N80S-A142P-L192V-V208H, K4V-S23L-Q36T-S77M-G112T-S157D-A161P-L192V-S221L, Q36T-V98Y-A142P-A161E-S225K, Q36T-P136E-A142P-S225K-S249P, A99Y-P136E-A142P-A161E-S221L, S32D-Q36T-S221L-S225K, S32D-A99Y-A142P-A161E-S249P, K44V-A142P-A161P-K163V, S32D-Q36T-G112S-A142P, S32D-Q36T-S77M-S135T-A142P-A161P, F29W-S77M-A99E-A142P, G112S-P136K-A142E, S135T-A142P-K163V, K4V-G112S-S135T-A142P-A161P, S32D-Q36T-A99E-P136K-A142P, G112S-P136K-A142P-S217M-S221M-T241L-G258K, K4V-S77K-G112S-A142P-A194S-S249G-G258K, P97S-G112V-P136S-A142P-A161E-K163V-P212S-S222A, P97S-G112V-P136S-S153D-A161E-S225K-T241R, P97S-G112V-P136S-S153D-S225K-T241R, S32D-A142E-V208K-S225K-T241R, S32D-A142E, S51T-A99Y-F119L-P136E-Q154E-D156G-S217G, K44V-A142P-A161P-K163V-K227R-T236A, G112T-S135T-Q154E-T233S-Z233.01T-Z233.02T-Z233.03S-Z233.04T-Z233.05S-Z233.06T-S237D, Q36T-S51T-V98G-T116V-A142P-A161P-T233 S-Z233.01T-Z233.02A-Z233.03S-Z233.04T-Z233.05K-Z233.06A-Z233.07T-Z233.08S-Z233.09T-Z233.10T, Q36T-S77K-G87A-A142P-S153D-A161P-D177Z-G204S-S221L-S237D, K4V-F29W-S51T-D65G-S77M-T116V-S153D-K163V-G204S-F206S-T210V-S221L-Z233.01S-Z233.02T-Z233.03T-Z233.04S-Z233.05T-Z233.06K-Z233.07A-Z233.08T-Z233.09S-Z233.10T-Z233.11T, S77M-S135T-Q154E-K163V-K227R-Z233.01S-Z233.02T-Z233.03T-Z233.04T-Z233.05D-Z233.06K-Z233.07A-Z233.08T-Z233.09S-Z233.10

T-Z233.11T-S237D, K4V-S32G-Q36T-S77M-G87A-T116V variant comprises (i) an amino acid sequence corresponding to position 1-295 of SEQ ID NO:1 and having at least 60%, 65%, 70%, 75%, 80%, 85%, 90%, 91%, 92%, 93%, 94%, 95%, 96%, 97%, 98%, 99%, or less than 100% amino acid sequence identity to the amino acid sequence of SEQ ID NO:71; (ii) an amino acid sequence corresponding to position 1-211 of SEQ ID NO:1 and having at least 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or less than 100% amino acid sequence identity to an amino acid sequence as shown in positions 1-211 of SEQ ID NO:71 set forth in FIG. 2; (iii) an amino acid sequence corresponding to position 212-258 of SEQ ID NO:1 and having at least 70%, 75%, 80%, 90%, 91%, 92%, 93%, 94%, 95%, 96%, 97%, 98%, 99%, or 100% amino acid sequence identity to an amino acid sequence as shown in positions 212-258 of SEQ ID NO:71 set forth in FIG. 3; (iv) an amino acid sequence corresponding to position 259-295 of SEQ ID NO:1 and having at least 60%, 67%, 68%, 70%, 73%, 75%, 76%, 80%, 81%, 83%, 84%, 90%, 91%, 92%, 93%, 94%, 95%, 96%, 97%, 98%, 99%, or 100% amino acid sequence identity to an amino acid sequence as shown in positions 259-295 of SEQ ID NO:71 set forth in FIG. 4; or (v) a combination of (i) to (iv). Still another embodiment is directed to one or more cellulase variant, or active fragment thereof, described herein, wherein said variant comprises (i) an amino acid sequence corresponding to position 1-295 of SEQ ID NO:1 and having at least 60%, 65%, 70%, 75%, 80%, 85%, 90%, 91%, 92%, 93%, 94%, 95%, 96%, 97%, 98%, 99%, or less than 100% amino acid sequence identity to the amino acid sequence of SEQ ID NO:72; (ii) an amino acid sequence corresponding to position 1-211 of SEQ ID NO:1 and having at least 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or less than 100% amino acid sequence identity to an amino acid sequence as shown in positions 1-211 of SEQ ID NO:72 set forth in FIG. 2; (iii) an amino acid sequence corresponding to position 212-258 of SEQ ID NO:1 and having at least 70%, 75%, 80%, 90%, 91%, 92%, 93%, 94%, 95%, 96%, 97%, 98%, 99%, or 100% amino acid sequence identity to an amino acid sequence as shown in positions 212-258 of SEQ ID NO:72 set forth in FIG. 3; (iv) an amino acid sequence corresponding to position 259-295 of SEQ ID NO:1 and having at least 60%, 67%, 68%, 70%, 73%, 75%, 76%, 80%, 81%, 83%, 84%, 90%, 91%, 92%, 93%, 94%, 95%, 96%, 97%, 98%, 99%, or 100% amino acid sequence identity to an amino acid sequence as shown in positions 259-295 of SEQ ID NO:72 set forth in FIG. 4; or (v) a combination of (i) to (iv). Yet another embodiment is directed to one or more cellulase variant, or active fragment thereof, described herein, wherein said variant comprises (i) an amino acid sequence corresponding to position 1-295 of SEQ ID NO:1 and having at least 60%, 65%, 70%, 75%, 80%, 85%, 90%, 91%, 92%, 93%, 94%, 95%, 96%, 97%, 98%, 99%, or less than 100% amino acid sequence identity to the amino acid sequence of SEQ ID NO:73; (ii) an amino acid sequence corresponding to position 1-211 of SEQ ID NO:1 and having at least 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or less than 100% amino acid sequence identity to an amino acid sequence as shown in positions 1-211 of SEQ ID NO:73 set forth in FIG. 2; (iii) an amino acid sequence corresponding to position 212-258 of SEQ ID NO:1 and having at least 70%, 75%, 80%, 90%, 91%, 92%, 93%, 94%, 95%, 96%, 97%, 98%, 99%, or 100% amino acid sequence identity to an amino acid sequence as shown in positions 212-258 of SEQ ID NO:73 set forth in FIG. 3; (iv) an amino acid sequence corresponding to position 259-295 of SEQ ID NO:1 and having at least 60%, 67%, 68%, 70%, 73%, 75%, 76%, 80%, 81%, 83%, 84%, 90%, 91%, 92%, 93%, 94%, 95%, 96%, 97%, 98%, 99%, or 100% amino acid sequence identity to an amino acid sequence as shown in positions 259-295 of SEQ ID NO:73 set forth in FIG. 4; or (v) a combination of (i) to (iv). Yet an even still yet further embodiment is directed to one or more cellulase variant, or active fragment thereof, described herein, wherein said variant comprises (i) an amino acid sequence corresponding to position 1-295 of SEQ ID NO:1 and having at least 60%, 65%, 70%, 75%, 80%, 85%, 90%, 91%, 92%, 93%, 94%, 95%, 96%, 97%, 98%, 99%, or less than 100% amino acid sequence identity to the amino acid sequence of SEQ ID NO:74; (ii) an amino acid sequence corresponding to position 1-211 of SEQ ID NO:1 and having at least 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or less than 100% amino acid sequence identity to an amino acid sequence as shown in positions 1-211 of SEQ ID NO:74 set forth in FIG. 2; (iii) an amino acid sequence corresponding to position 212-258 of SEQ ID NO:1 and having at least 70%, 75%, 80%, 90%, 91%, 92%, 93%, 94%, 95%, 96%, 97%, 98%, 99%, or 100% amino acid sequence identity to an amino acid sequence as shown in positions 212-258 of SEQ ID NO:74 set forth in FIG. 3; (iv) an amino acid sequence corresponding to position 259-295 of SEQ ID NO:1 and having at least 60%, 67%, 68%, 70%, 73%, 75%, 76%, 80%, 81%, 83%, 84%, 90%, 91%, 92%, 93%, 94%, 95%, 96%, 97%, 98%, 99%, or 100% amino acid sequence identity to an amino acid sequence as shown in positions 259-295 of SEQ ID NO:74 set forth in FIG. 4; or (v) a combination of (i) to (iv). An even still further embodiment is directed to one or more cellulase variant, or active fragment thereof, described herein, wherein said variant comprises (i) an amino acid sequence corresponding to position 1-295 of SEQ ID NO:1 and having at least 60%, 65%, 70%, 75%, 80%, 85%, 90%, 91%, 92%, 93%, 94%, 95%, 96%, 97%, 98%, 99%, or less than 100% amino acid sequence identity to the amino acid sequence of SEQ ID NO:75; (ii) an amino acid sequence corresponding to position 1-211 of SEQ ID NO:1 and having at least 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or less than 100% amino acid sequence identity to an amino acid sequence as shown in positions 1-211 of SEQ ID NO:75 set forth in FIG. 2; (iii) an amino acid sequence corresponding to position 212-258 of SEQ ID NO:1 and having at least 70%, 75%, 80%, 90%, 91%, 92%, 93%, 94%, 95%, 96%, 97%, 98%, 99%, or 100% amino acid sequence identity to an amino acid sequence as shown in positions 212-258 of SEQ ID NO:75 set forth in FIG. 3; (iv) an amino acid sequence corresponding to position 259-295 of SEQ ID NO:1 and having at least 60%, 67%, 68%, 70%, 73%, 75%, 76%, 80%, 81%, 83%, 84%, 90%, 91%, 92%, 93%, 94%, 95%, 96%, 97%, 98%, 99%, or 100% amino acid sequence identity to an amino acid sequence as shown in positions 259-295 of SEQ ID NO:75 set forth in FIG. 4; or (v) a combination of (i) to (iv).

Another further embodiment is directed to one or more cellulase variant, or active fragment thereof, described herein, wherein said variant is derived from a parent or reference polypeptide selected from SEQ ID NOs:1, 70, 71, 72, 73, 74, and 75. Still another further embodiment is directed to one or more cellulase variant, or active fragment thereof, described herein, wherein said variant is derived from the parent or reference polypeptide of SEQ ID NO:1. Still another embodiment is directed to one or more cellulase variant, or active fragment thereof, described herein, wherein said variant is derived from the parent or reference polypeptide of SEQ ID NO:70. A further embodiment is directed to one or more cellulase variant, or active fragment thereof, described herein, wherein said variant is derived from the parent or reference polypeptide of SEQ ID NO:71. A still further embodiment is directed to one or more cellulase variant, or active fragment thereof, described herein, wherein said variant is derived from the parent or reference polypeptide of SEQ ID NO:72. Another embodiment is directed to one or more cellulase variant, or active fragment thereof, described herein, wherein said variant is derived from the parent or reference polypeptide of SEQ ID NO:73. Yet another embodiment is directed to one or more cellulase variant, or active fragment thereof, described herein, wherein said variant is derived from the parent or reference polypeptide of SEQ ID NO:74. Yet still another embodiment is directed to one or more cellulase variant, or active fragment thereof, described herein, wherein said variant is derived from the parent or reference polypeptide of SEQ ID NO:75.

In a further embodiment, the cellulase variant, or active fragment thereof, described herein has one or more improved property selected from improved thermostability, improved stability in the presence of one or more other enzyme, and improved stability in the presence of one or more other enzyme and one or more other detergent component. In another embodiment, the other enzyme is protease and/or the other detergent component is a surfactant. In some embodiments, the improved property is improved when compared to the parent or reference polypeptide.

In other embodiments, the improved property is improved thermostability, and the variant, or active fragment thereof, has a thermal Performance Index (PI) that is greater than 1 or ≥1.1. In still other embodiments, the improved property is improved stability in the presence of one or more protease, and the variant, or active fragment thereof, has a PI that is greater than 1 or ≥1.1, 1.2, 1.3, 1.4, 1.5, or 2.0 when the stability of said variant, or active fragment thereof is tested in the presence of said protease. In an even further embodiment, the improved property is improved stability in the presence of one or more protease and one or more other detergent component, and wherein said variant, or active fragment thereof, has a PI that is greater than 1 or ≥1.1, 1.5, 2.0, or 2.5 when the stability of said variant, or active fragment thereof is tested in the presence of said protease and said other detergent component. In yet a further embodiment, the PI is measured in accordance with the Cellulase Activity Assay of Example 1.

In one embodiment, the cellulase variants, or active fragments thereof, described herein are family GH45 cellulases. In some embodiments, the cellulase variants, or active fragments thereof, described herein are isolated.

Further embodiments are directed to a polynucleotide that encodes the cellulase variants, or active fragments thereof, described herein. In one embodiment, the polynucleotide is contained in an expression vector contained in a heterologous organism. The polynucleotide may be operably-linked to regulatory elements (e.g., a promoter, terminator, and enhancer) to assist in expressing the encoded cellulase variants, or active fragments thereof, described herein. In some embodiments, the cellulase variant, or active fragment thereof, described herein is expressed in a heterologous organism as a secreted polypeptide, in which case, the compositions and method encompass a method for expressing the variant or active fragment thereof as a secreted polypeptide in a heterologous organism.

DNA that encodes a cellulase variant, or active fragment thereof, described herein can be chemically synthesized from published sequences or obtained directly from host cells harboring the gene (e.g., by cDNA library screening or PCR amplification).

Further embodiments are directed to methods of producing a cellulase variant, or active fragment thereof, described herein comprising: stably transforming a host cell with an expression vector comprising a polynucleotide encoding the cellulase variant, or active fragment thereof; culturing the transformed host cell under suitable conditions to produce the cellulase variant, or active fragment thereof, and recovering the cellulase variant, or active fragment thereof.

In other embodiments, a cellulase variant, or active fragment thereof, described herein is fused to a signal peptide for directing the extracellular secretion of the variant, or active fragment thereof. For example, in certain embodiments, the signal peptide is the native signal peptide of the cellulase variant, or active fragment thereof described herein. In other embodiments, the signal peptide is a non-native signal peptide such as the *B. subtilis* AprE signal peptide.

In some embodiments, the host cell in which the cellulase variant, or active fragment thereof, described herein is expressed in a heterologous organism, i.e., an organism other than *Staphylotrichum* spp. Exemplary heterologous organisms, include, for example, *B. subtilis, B. licheniformis, B. lentus, B. brevis, Geobacillus* (formerly *Bacillus*) *stearothermophilus, B. alkalophilus, B. amyloliquefaciens, B. coagulans, B. circulans, B. lautus, B. megaterium, B. thuringiensis, S. lividans, S. murinus, P. fluorescens, P. stutzerei, P. mirabilis, R. eutropha, S. carnosus, L. lactis, E. coli,* yeast (such as, for example, *Saccharomyces* spp. or *Schizosaccharomyces* spp., e.g. *S. cerevisiae*), *C. lucknowense,* and filamentous fungi such as *Aspergillus* spp., e.g., *A. oryzae* or *A. niger, H. grisea, H. insolens,* and *T. reesei*. Methods for transforming nucleic acids into these organisms are well known in the art. A suitable procedure for transformation of *Aspergillus* host cells is described, for example, in EP238023. A suitable procedure for transformation of *Trichoderma* host cells is described, for example, in Steiger et al 2011, *Appl. Environ. Microbiol.* 77:114-121.

In some embodiments, the polynucleotide is codon-optimized for expression in a different host, mutated to introduce cloning sites, or otherwise altered to add functionality.

In some embodiments, expression vectors are provided in a heterologous host cell suitable for expressing the cellulase variant, or active fragment thereof, described herein, or suitable for propagating the expression vector prior to introducing it into a suitable host cell. In some embodiments, the polynucleotide is included in an expression cassette and/or cloned into a suitable expression vector by standard molecular cloning techniques. Such expression cassettes or vectors contain sequences that assist initiation and termination of transcription (e.g., promoters and terminators), and generally contain a selectable marker In some embodiments, a polynucleotide that encodes a cellulase variant, or active fragment thereof, hybridizes to a polynucleotide encoding one or more of the variants described herein or the complement thereof under specified hybridization conditions. The term "hybridization" refers to the process by which a strand of nucleic acid joins with a complementary strand through base pairing, as known in the art. The term "hybridization conditions" refers to the conditions under which hybridization reactions are conducted. These conditions are typically classified by degree of "stringency" of the conditions under which hybridization is measured. The degree of stringency can be based, for example, on the melting temperature ($T_m$) of the nucleic acid binding complex or probe. For example, "maximum stringency" typically occurs at about $T_m$–5° C. (5° below the $T_m$ of the probe); "high stringency" at about 5-10° C. below the $T_m$; "intermediate stringency" at about 10-20° C. below the $T_m$ of the probe; and "low stringency" at about 20-25° C. below the $T_m$. Alternatively, or in addition, hybridization conditions can be based upon the salt or ionic strength conditions of hybridization and/or one or more stringency washes, e.g., 6×SSC=very low stringency; 3×SSC=low to medium stringency; 1×SSC=medium stringency; and 0.5×SSC=high stringency. Functionally, maximum stringency conditions may be used to identify nucleic acid sequences having strict identity or near-strict identity with the hybridization probe; while high stringency conditions are used to identify nucleic acid sequences having about 80% or more sequence identity with the probe. For applications requiring high selectivity, it is typically desirable to use relatively stringent conditions to form the hybrids (e.g., relatively low salt and/or high temperature conditions are used).

A further embodiment is directed to a composition comprising one or more cellulase variant, or active fragment thereof, describe herein. In another embodiment, the composition is selected from an enzyme composition, detergent composition, and fabric care composition. In some embodiments, the composition is an enzyme composition. In other embodiments, the composition is a detergent composition. In still other embodiments, the composition is a fabric care composition. In yet other embodiments, the detergent composition is a laundry detergent. In still other embodiments, the laundry detergent is selected from heavy-duty liquid (HDL) laundry detergent and heavy-duty dry (HDD) granular laundry detergent.

In some further embodiments, the composition is in a form selected from a powder, liquid, granular, bar, solid, semi-solid, gel, paste, emulsion, tablet, capsule, unit dose, sheet, and foam. In even further embodiments, the composition is in a form selected from a liquid, powder, granulated solid, tablet, sheet, and unit dose. In some embodiments, the compositions described herein are provided in unit dose form, including tablets, capsules, sachets, pouches, sheets, and multi-compartment pouches. In some embodiments, the unit dose format is designed to provide controlled release of the ingredients within a multi-compartment pouch (or other unit dose format). Suitable unit dose and controlled release formats are known in the art (See e.g., EP2100949, EP2100947, WO02/102955, WO04/111178, WO2013/165725, and U.S. Pat. Nos. 4,765,916 and 4,972,017). In some embodiments, the unit dose form is provided by tablets wrapped with a water-soluble film or water-soluble pouches.

In yet even further embodiments, the composition contains phosphate or is phosphate-free and/or contains boron or is boron-free. In still other embodiments, the composition contains phosphate. In yet still other embodiments, the composition is phosphate-free. In even still further embodiments, the composition contains boron. In yet even still further embodiments, the composition is boron-free.

In yet other embodiments, the composition further comprises (i) one or more other enzymes selected from acyl transferases, amylases, alpha-amylases, beta-amylases, alpha-galactosidases, arabinases, arabinosidases, aryl esterases, beta-galactosidases, beta-glucanases, carrageenases, catalases, chondroitinases, cutinases, endo-beta-mannanases, exo-beta-mannanases, esterases, exo-mannanases, galactanases, glucoamylases, hemicellulases, hyaluronidases, keratinases, laccases, lactases, ligninases, lipases, lipolytic enzymes, lipoxygenases, mannanases, metalloproteases, oxidases, oxidoreductase, pectate lyases, pectin acetyl esterases, pectinases, pentosanases, perhydrolases, peroxidases, phenoloxidases, phosphatases, phospholipases, phytases, polyesterase, polygalacturonases, proteases, pullulanases, reductases, rhamnogalacturonases, second cellulase, beta-glucanases, tannases, transglutaminases, xylan acetyl-esterases, xylanases, and xylosidases; (ii) one or more surfactants; (iii) one or more ions selected from calcium and zinc; (iv) one or more adjunct ingredients; (v) one or more stabilizers; (vi) from about 0.001% to about 5.0 weight % of the cellulase variant, or active fragment thereof, described herein; (vii) one or more bleaching agents; or (viii) combinations thereof.

In still further embodiments, the composition comprises one or more other enzyme. In yet still further embodiments, the one or more other enzyme is selected from acyl transferases, amylases, alpha-amylases, beta-amylases, alpha-galactosidases, arabinases, arabinosidases, aryl esterases, beta-galactosidases, beta-glucanases, carrageenases, catalases, chondroitinases, cutinases, endo-beta-mannanases, exo-beta-mannanases, esterases, exo-mannanases, galactanases, glucoamylases, hemicellulases, hyaluronidases, keratinases, laccases, lactases, ligninases, lipases, lipolytic enzymes, lipoxygenases, mannanases, metalloproteases, oxidases, oxidoreductases, pectate lyases, pectin acetyl esterases, pectinases, pentosanases, perhydrolases, peroxidases, phenoloxidases, phosphatases, phospholipases, phytases, polygalacturonases, polyesterases, proteases, pullulanases, reductases, rhamnogalacturonases, second cellulase, beta-glucanases, tannases, transglutaminases, xylan acetyl-esterases, xylanases, and xylosidases. In further embodiments, the compositions described herein further comprise a protease, mannanase, and/or amylase.

In some embodiments, the composition further comprises one or more surfactant. In some other embodiments, the surfactant is selected from non-ionic, ampholytic, semi-polar, anionic, cationic, zwitterionic, and combinations and mixtures thereof. In yet still other embodiments, the surfactant is selected from anionic, cationic, nonionic, and zwitterionic compounds. In some embodiments, the composition comprises from about 0.1% to about 60%, about 1% to about 50%, or about 5% to about 40% surfactant by weight of the composition. Exemplary surfactants include, but are not limited to sodium dodecylbenzene sulfonate, C12-14 pareth-7, C12-15 pareth-7, sodium C12-15 pareth sulfate, C14-15 pareth-4, sodium laureth sulfate (e.g., Steol CS-370), sodium hydrogenated cocoate, C12 ethoxylates (Alfonic 1012-6, Hetoxol LA7, Hetoxol LA4), sodium alkyl benzene sulfonates (e.g., Nacconol 90G), and combinations and mixtures thereof. Anionic surfactants include but are not limited to linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. Nonionic surfactants include but are not limited to alcohol ethoxylate (AEO or AE), carboxylated alcohol ethoxylates, nonylphenol ethoxylate, alkylpolyglycoside, alkyldimethylamine oxide, ethoxylated fatty acid monoethanolamide, fatty acid monoethanolamide, polyhydroxy alkyl fatty acid amide (e.g., as described in WO92/06154), polyoxyethylene esters of fatty acids, polyoxyethylene sorbitan esters (e.g., TWEENs), polyoxyethylene alcohols, polyoxyethylene isoalcohols, polyoxyethylene ethers (e.g., TRITONs and BRIJ), polyoxyethylene esters, polyoxyethylene-p-tert-octylphenols or octylphenyl-ethylene oxide condensates (e.g., NONIDET P40), ethylene oxide condensates with fatty alcohols (e.g., LUBROL), polyoxyethylene nonylphenols, polyalkylene glycols (SYNPERONIC F108), sugar-based surfactants (e.g., glycopyranosides, thioglycopyranosides), and combinations and mixtures thereof.

In a further embodiment, the detergent compositions disclosed herein further comprise a surfactant mixture that includes, but is not limited to 5-15% anionic surfactants, <5% nonionic surfactants, cationic surfactants, phosphonates, soap, enzymes, perfume, butylphenyl methylptopionate, geraniol, zeolite, polycarboxylates, hexyl cinnamal, limonene, cationic surfactants, citronellol, and benzisothiazolinone.

In other embodiments, the composition further comprises one or more calcium and/or zinc ions.

In still other embodiments, the composition further comprises one or more adjunct ingredients. In yet other embodiments, the adjunct ingredient is selected from a bleach activator, bleach catalyst, enzyme stabilizing system, chelant, optical brightener, soil release polymer, dye transfer agent, dye transfer inhibiting agent, catalytic material, hydrogen peroxide, sources of hydrogen peroxide, preformed peracids, polymeric dispersing agent, clay soil removal agent, structure elasticizing agent, dispersant, suds suppressor, dye, perfume, colorant, filler salt, hydrotrope, photoactivator, fluorescer, fabric conditioner, hydrolyzable surfactant, solvent, preservative, anti-oxidant, anti-shrinkage agent, anti-wrinkle agent, germicide, fungicide, color speckle, anti-corrosion agent, alkalinity source, solubilizing agent, carrier, processing aid, perfume, pigment, and pH control agents (See, e.g., U.S. Pat. Nos. 6,610,642; 6,605, 458; 5,705,464; 5,710,115; 5,698,504; 5,695,679; 5,686, 014; and 5,646,101).

In another embodiment, the composition further comprises one or more stabilizers. In another embodiment, the stabilizer is selected from water-soluble sources of calcium and/or magnesium ions; polysaccharides; and inorganic divalent metal salts, including alkaline earth metals, such as calcium salts. In some embodiments, the enzymes employed herein are stabilized by the presence of water-soluble sources of zinc (II), calcium (II), and/or magnesium (II) ions in the finished compositions, as well as other metal ions (e.g., barium (II), scandium (II), iron (II), manganese (II), aluminum (III), tin (II), cobalt (II), copper (II), nickel (II), and oxovanadium (IV). Chlorides and sulfates also find use in some embodiments. Examples of suitable oligosaccharides and polysaccharides (e.g., dextrins) are known in the art (See, e.g., WO07/145964). In some embodiments, reversible protease inhibitors also find use, such as boron-containing compounds (e.g., borate, 4-formyl phenyl boronic acid) and/or a tripeptide aldehyde find use to further improve stability, as desired.

In yet another embodiment, the composition further comprises an effective amount of a cellulase variant, or active fragment thereof, described herein. In some embodiments, the effective amount of a cellulase variant, or active fragment thereof, is from about 0.00001% to about 10%, about 0.0001% to about 10%, about 0.001% to about 5%, about 0.001% to about 2%, or about 0.005% to about 0.5% of cellulase by weight of the composition. In other embodiments, the effective amount of cellulase variant, or active fragment thereof, is from about 0.001% to about 5.0 weight percent composition. In still other embodiments, the effective amount of cellulase variant, or active fragment thereof, is from about 0.001% to about 4.5 weight percent composition. In still yet other embodiments, the effective amount of cellulase variant, or active fragment thereof, is from about 0.001% to about 4.0 weight percent composition. In yet even other embodiments, the effective amount of cellulase variant, or active fragment thereof, is from about 0.001% to about 3.5, 3.6, 3.7, 3.8, or 3.9 weight percent composition.

In even still further embodiments, the composition further comprises one or more bleaching agents. In yet another embodiment, the bleaching agent is selected from inorganic and/or organic bleaching compound(s). Inorganic bleaches may include, but are not limited to perhydrate salts (e.g., perborate, percarbonate, perphosphate, persulfate, and persilicate salts). In some embodiments, inorganic perhydrate salts are alkali metal salts. In some embodiments, inorganic perhydrate salts are included as the crystalline solid, without additional protection, although in some other embodiments, the salt is coated. Suitable salts include, for example, those described in EP2100949.

In some embodiments, the compositions described herein further comprises one or more detergent builders or builder systems, complexing agents, polymers, foam boosters, suds suppressors, anti-corrosion agents, soil-suspending agents, anti-soil redeposition agents, dyes, bactericides, hydrotopes, optical brighteners, fabric conditioners, and perfumes.

In some embodiments, the composition described herein further comprises from about 1%, from about 3% to about 60%, or from about 5% to about 40% builder by weight of the composition. Builders may include, but are not limited to, the alkali metals, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metals, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof.

In some embodiments, the builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). Any suitable builder can find use in the compositions described herein, including those known in the art (See, e.g., EP 2100949).

In an even further embodiment, the pH of the composition is neutral to basic. The laundry compositions described herein are typically formulated such that, during use in aqueous conditions, the wash water will have a pH of from about 3.0 to about 11. Liquid products are typically formulated to have a neat pH from about 5.0 to about 9.0. Granular products are typically formulated to have a pH from about 8.0 to about 11.0. Techniques for controlling pH at recommended usage levels include the use of buffers, alkalis, acids, etc., and are well known to those skilled in the art.

The term "granular composition" refers to a conglomeration of discrete solid, macroscopic particles. Powders are a special class of granular material due to their small particle size, which makes them more cohesive and more easily suspended.

Concentrations of detergent compositions in typical wash solutions throughout the world varies from less than about 800 ppm of detergent composition ("low detergent concentration geographies"), for example about 667 ppm in Japan, to between about 800 ppm to about 2000 ppm ("medium detergent concentration geographies"), for example about 975 ppm in U.S. and about 1500 ppm in Brazil, to greater than about 2000 ppm ("high detergent concentration geographies"), for example about 4500 ppm to about 5000 ppm in Europe and about 6000 ppm in high suds phosphate builder geographies.

In some embodiments, the detergent compositions described herein may be utilized at a temperature of from about 10° C. to about 60° C., or from about 20° C. to about 60° C., or from about 30° C. to about 60° C., from about 40° C. to about 60° C., from about 40° C. to about 55° C., or all ranges within 10° C. to 60° C. In some embodiments, the detergent compositions described herein are used in "cold water washing" at temperatures of from about 10° C. to about 40° C., or from about 20° C. to about 30° C., from about 15° C. to about 25° C., from about 15° C. to about 35° C., or all ranges within 10° C. to 40° C.

As a further example, different geographies typically have different water hardness. Water hardness is usually described in terms of the grains per gallon mixed $Ca^{2+}/Mg^{2+}$. Hardness is a measure of the amount of calcium ($Ca^{2+}$) and magnesium ($Mg^{2+}$) in the water. Most water in the United States is hard, but the degree of hardness varies. Moderately hard (60-120 ppm) to hard (121-181 ppm) water has 60 to 181 parts per million (parts per million converted to grains per U.S. gallon is ppm #divided by 17.1 equals grains per gallon) of hardness minerals.

TABLE II

Water Hardness Levels

| Water | Grains per gallon | Parts per million |
| --- | --- | --- |
| Soft | less than 1.0 | less than 17 |
| Slightly hard | 1.0 to 3.5 | 17 to 60 |
| Moderately hard | 3.5 to 7.0 | 60 to 120 |
| Hard | 7.0 to 10.5 | 120 to 180 |
| Very hard | greater than 10.5 | greater than 180 |

European water hardness is typically greater than about 10.5 (for example about 10.5 to about 20.0) grains per gallon mixed $Ca^{2+}/Mg^{2+}$ (e.g., about 15 grains per gallon mixed $Ca^{2+}/Mg^{2+}$). North American water hardness is typically greater than Japanese water hardness, but less than European water hardness. For example, North American water hardness can be between about 3 to about 10 grains, about 3 to about 8 grains or about 6 grains. Japanese water hardness is typically lower than North American water hardness, usually less than about 4, for example about 3 grains per gallon mixed $Ca^{2+}/Mg^{2+}$.

In some embodiments, the detergent compositions described herein further comprise a protease. In some embodiments the composition comprises from about 0.00001% to about 10% protease by weight of the composition. In another embodiment, the cleaning composition comprises from about 0.0001% to about 10%, about 0.001% to about 5%, about 0.001% to about 2%, or about 0.005% to about 0.5% protease by weight of the composition.

In one embodiment, the protease is a serine protease. Suitable proteases include those of animal, vegetable or microbial origin. In some embodiments, the protease is a microbial protease. In other embodiments, the protease is a chemically or genetically modified mutant. In another embodiment, the protease is an alkaline microbial protease or a trypsin-like protease. Exemplary alkaline proteases include subtilisins derived from, for example, *Bacillus* (e.g., subtilisin, *lentus, amyloliquefaciens*, subtilisin Carlsberg, subtilisin 309, subtilisin 147 and subtilisin 168). Exemplary additional proteases include but are not limited to those described in WO9221760, WO9523221, WO2008010925, WO09149200, WO09149144, WO09149145, WO 10056640, WO10056653, WO20100566356, WO11072099, WO201113022, WO11140364, WO 12151534, WO2015038792, WO2015089447, WO2015089441, WO2015/143360, WO2016 061438, WO2016069548, WO2016069544, WO2016069557, WO2016069563, WO2016 069569, WO2016069552, WO2016145428, WO2016183509, US Publ. No. 20080090747, U.S. Pat. Nos. 5,801,039, 5,340,735, 5,500,364, 5,855,625, RE34606, U.S. Pat. Nos. 5,955,340, 5,700,676, 6,312,936, 6,482,628, 8,530,219, U.S. Provisional Appl Nos. 62/331,282, 62/332,417, 62/343,618, and 62/351,649, and International Appl No. PCT/US2016/038245, as well as metalloproteases described in WO1999014341, WO1999033960, WO1999014342, WO1999 034003, WO2007044993, WO2009058303, WO2009058661, WO2014071410, WO2014 194032, WO2014194034, WO2014194054, and WO2014 194117. Exemplary proteases also include, but are not limited to trypsin (e.g., of porcine or bovine origin) and the *Fusarium* protease described in WO8906270.

Exemplary commercial proteases include, but are not limited to MAXATASE®, MAXACAL™, MAXAPEM™, OPTICLEAN®, OPTIMASE®, PROPERASE®, PURAFECT®, PURAFECT® OXP, PURAMAX™, EXCELLASE™, PREFERENZ™ proteases (e.g. P100, P110, P280), EFFECTENZ™ proteases (e.g. P1000, P1050, P2000), EXCELLENZ™ proteases (e.g. P1000), ULTIMASE®, and PURAFAST™ (DuPont); ALCALASE®, ALCALASE® ULTRA, BLAZE®, BLAZE® EVITY®, BLAZE® EVITY® 16L, CORONASE®, SAVINASE®, SAVINASE® ULTRA, SAVINASE® EVITY®, SAVINASE® EVERIS®, PRIMASE®, DURAZYM™, POLARZYME®, OVOZYME®, KANNASE®, LIQUANASE®, LIQUANASE EVERIS®, NEUTRASE®, PROGRESS UNO®, RELASE® and ESPERASE® (Novozymes); BLAP™ and BLAP™ variants (Henkel); LAVERGY™ PRO 104 L (BASF), and KAP (*B. alkalophilus* subtilisin (Kao)).

In some embodiments, the detergent compositions described herein further comprise a suitable amylase. In one embodiment, the composition comprises from about 0.00001% to about 10%, about 0.0001% to about 10%, about 0.001% to about 5%, about 0.001% to about 2%, or about 0.005% to about 0.5% amylase by weight of the composition. Any amylase (e.g., alpha and/or beta) suitable for use in alkaline solutions may be useful to include in such composition. An exemplary amylase can be a chemically or genetically modified mutant. Exemplary amylases include, but are not limited amylases described in GB1296839, WO91 00353, WO9402597, WO94183314, WO9510603, WO9526397, WO9535382, WO9605295, WO9623873, WO9623874, WO9630481, WO9710342, WO9741213, WO9743424, WO98 13481, WO9826078, WO9902702, WO9909183, WO9919467, WO9923211, WO9929876, WO9942567, WO9943793, WO9943794, WO9946399, WO0029560, WO0060058, WO00 60059, WO0060060, WO0114532, WO0134784, WO0164852, WO0166712, WO0188107, WO0196537, WO02092797, WO0210355, WO0231124, WO2004055178, WO2004113551, WO2005001064, WO2005003311, WO2005018336, WO 2005019443, WO2005066338, WO 2006002643, WO2006012899, WO2006012902, WO2006 031554, WO2006063594, WO2006 066594, WO2006066596, WO2006136161, WO2008 000825, WO2008088493, WO2008 092919, WO2008101894, WO2008112459, WO2009 061380, WO2009061381, WO2009 100102, WO2009140504, WO2009149419, WO2010 059413, WO2010088447, WO2010 091221, WO2010104675, WO2010 115021, WO10115028, WO2010117511, WO2011076123, WO2011076897, WO2011080352, WO2011080353, WO2011080354, WO2011082425, WO 2011082429, WO2011087836, WO2011098531, WO2013063460, WO2013184577, WO2014 099523, WO2014164777, and WO2015077126. Exemplary commercial amylases include, but are not limited to AMPLIFY®, AMPLIFY PRIME®, BAN™, DURAMYL®, TERMAMYL®, TERMAMYL® ULTRA, FUNGAMYL®, STAINZYME®, STAINZYME PLUS®, STAINZYME ULTRA®, and STAINZYME EVITY® (Novozymes); EFFECTENZ™ S 1000, POWERASE T, PREFERENZ™ S 100, PREFERENZ™ S 110, EXCELLENZ™ S2000, RAPIDASE® and MAXAMYL® P (DuPont).

In some embodiments, the detergent compositions described herein further comprise a suitable pectin degrading enzyme. As used herein, "pectin degrading enzyme(s)" encompass arabinanase (EC 3.2.1.99), galactanases (EC 3.2.1.89), polygalacturonase (EC 3.2.1.15) exo-polygalacturonase (EC 3.2.1.67), exo-poly-alpha-galacturonidase (EC 3.2.1.82), pectin lyase (EC 4.2.2.10), pectin esterase (EC 3.2.1.11), pectate lyase (EC 4.2.2.2), exo-polygalacturonate lyase (EC 4.2.2.9) and hemicellulases such as endo-1,3-β-xylosidase (EC 3.2.1.32), xylan-1,4-β-xylosidase (EC 3.2.1.37) and α-L-arabinofuranosidase (EC 3.2.1.55). Pectin degrading enzymes are natural mixtures of the above mentioned enzymatic activities. Pectin enzymes therefore include the pectin methylesterases which hydrolyses the pectin methyl ester linkages, polygalacturonases which cleave the glycosidic bonds between galacturonic acid molecules, and the pectin transeliminases or lyases which act on the pectic acids to bring about non-hydrolytic cleavage of α-1,4 glycosidic linkages to form unsaturated derivatives of galacturonic acid.

Suitable pectin degrading enzymes include those of plant, fungal, or microbial origin. In some embodiments, chemically or genetically modified mutants are included. In some embodiments, the pectin degrading enzymes are alkaline pectin degrading enzymes, i.e., enzymes having an enzymatic activity of at least 10%, at least 25%, or at least 40% of their maximum activity at a pH of from about 7.0 to about 12. In certain other embodiments, the pectin degrading enzymes are enzymes having their maximum activity at a pH of from about 7.0 to about 12. Alkaline pectin degrading enzymes are produced by alkalophilic microorganisms e.g., bacterial, fungal, and yeast microorganisms such as *Bacillus* species. In some embodiments, the microorganisms are *B. firmus, B. circulans*, and *B. subtilis* as described in JP 56131376 and JP 56068393. Alkaline pectin decomposing enzymes may include but are not limited to galacturn-1,4-α-galacturonase (EC 3.2.1.67), poly-galacturonase activities (EC 3.2.1.15, pectin esterase (EC 3.1.1.11), pectate lyase (EC 4.2.2.2) and their iso enzymes. Alkaline pectin decomposing enzymes can be produced by the *Erwinia* species. In some embodiments, the alkaline pectin decomposing enzymes are produced by *E. chrysanthemi, E. carotovora, E. amylovora, E. herbicola*, and *E. dissolvens* as described in JP 59066588, JP 63042988, and in *World J. Microbiol. Microbiotechnol*. (8, 2, 115-120) 1992. In certain other embodiments, the alkaline pectin enzymes are produced by *Bacillus* species as disclosed in JP 73006557 and *Agr. Biol. Chem*. (1972), 36 (2) 285-93. In some embodiments, the detergent compositions described herein further comprise about 0.00001% to about 10%, about 0.0001% to about 10%, about 0.001% to about 5%, about 0.001% to about 2%, or about 0.005% to about 0.5% of pectin degrading enzyme by weight of the composition.

In some embodiments, the detergent compositions described herein further comprise a suitable mannanase enzyme. In one embodiment, the composition comprises from about 0.00001% to about 10%, about 0.0001% to about 10%, about 0.001% to about 5%, about 0.001% to about 2%, or about 0.005% to about 0.5% mannanase by weight composition. An exemplary mannanase can be a chemically or genetically modified mutant. Exemplary mannanases include, but are not limited to, those of bacterial or fungal origin, such as, for example, as is described in WO 2016/007929; U.S. Pat. Nos. 6,566,114; 6,602,842; and 6,440,991; and International Patent Appl Nos: PCT/US2016/060850 and PCT/US2016/060844 filed Nov. 7, 2016. Exemplary commercial mannanases include, but are not limited to MANNAWAY® (Novozymes) and EFFECTENZ™ M 1000, PREFERENZ® M 100, MANNASTAR®, and PURABRITE™ (DuPont).

In some further embodiments, the detergent compositions described herein further comprise a suitable second cellulase. Suitable second cellulases include, but are not limited to those of bacterial or fungal origin. Chemically or genetically modified mutants are included in some embodiments. Suitable second cellulases include, but are not limited to *H. insolens* cellulases (See, e.g., U.S. Pat. No. 4,435,307). Especially suitable cellulases are the cellulases having color care benefits (See, e.g., EP0495257). Commercially available second cellulases include, but are not limited to ENDOLASE®, CELLUCLEAN®, CELLUZYME®, CAREZYME®, RENOZYME®, and CAREZYME® PREMIUM (Novozymes A/S, Denmark), PURADEX®, (DuPont), and KAC-500(B)™ (Kao Corporation). In some embodiments, cellulases are incorporated as portions or fragments of mature wild-type or variant cellulases, wherein a portion of the N-terminus is deleted (See, e.g., U.S. Pat. No. 5,874,276). In some embodiments, the detergent compositions described herein further comprise from about 0.00001% to about 10%, about 0.0001% to about 10%, about 0.001% to about 5%, about 0.001% to about 2%, or about 0.005% to about 0.5% of cellulase by weight of the composition.

In still further embodiments, the detergent compositions described herein further comprise a suitable lipase. In some embodiments, the composition comprises from about 0.00001% to about 10%, about 0.0001% to about 10%, about 0.001% to about 5%, about 0.001% to about 2%, or about 0.005% to about 0.5% lipase by weight composition. An exemplary lipase can be a chemically or genetically modified mutant. Exemplary lipases include, but are not limited to, e.g., bacterial or fungal origin, such as, e.g., *H. lanuginosa* lipase (See, e.g., EP258068, and EP305216), *R. miehei* lipase (See, e.g., EP 238 023), *Candida* lipase, such as *C. antarctica* lipase (e.g., *C. antarctica* lipase A or B; see, e.g., EP214761), *Pseudomonas* lipases such as *P. alcaligenes* lipase and *P. pseudoalcaligenes* lipase (See, e.g., EP218272), *P. cepacia* lipase (See, e.g., EP331376), *P. stutzeri* lipase (See, e.g., GB 1,372,034), *P. fluorescens* lipase, *Bacillus* lipase (e.g., *B. subtilis* lipase [Dartois et al., (1993) *Biochem. Biophys. Acta* 1131:253-260]; *B. stearothermophilus* lipase [See, e.g., JP 64/744992]; and *B. pumi-*

*lus* lipase [See, e.g., WO91/16422]). Exemplary cloned lipases include, but are not limited to *P. camembertii* lipase (See, Yamaguchi et al., [1991] *Gene* 103:61-67), *G. candidum* lipase (See, Schimada et al., [1989] *J. Biochem.* 106:383-388), and various *Rhizopus* lipases such as *R. delemar* lipase (See, Hass et al., [1991] *Gene* 109:117-113), *R. niveus* lipase (Kugimiya et al., [1992] *Biosci. Biotech. Biochem.* 56:716-719), and *R. oryzae* lipase. Other types of suitable lipolytic enzymes include cutinases such as, for example, cutinase derived from *P. mendocina* (See, WO88/09367) and from *F. solani pisi* (See, WO90/09446). Exemplary commercial lipases include, but are not limited to M1 LIPASE™, LUMA FAST™, and LIPOMAX™ (DuPont); LIPEX®, LIPOCLEAN®, LIPOLASE® and LIPOLASE® ULTRA (Novozymes); and LIPASE P™ (Amano Pharmaceutical Co. Ltd).

In some embodiments, detergent compositions described herein further comprise peroxidases in combination with hydrogen peroxide or a source thereof (e.g., a percarbonate, perborate or persulfate). In some alternative embodiments, oxidases are used in combination with oxygen. Both types of enzymes are used for "solution bleaching" (i.e., to prevent transfer of a textile dye from a dyed fabric to another fabric when the fabrics are washed together in a wash liquor), preferably together with an enhancing agent (See, e.g., WO94/12621 and WO95/01426). Suitable peroxidases/oxidases include, but are not limited to those of plant, bacterial or fungal origin. Chemically or genetically modified mutants are included in some embodiments. In some embodiments, the detergent compositions further comprise from about 0.00001% to about 10%, about 0.0001% to about 10%, about 0.001% to about 5%, about 0.001% to about 2%, about 0.005% to about 0.5% of peroxidase and/or oxidase by weight of composition.

In some embodiments, detergent compositions described herein further comprise additional enzymes, including but not limited to perhydrolases (See, e.g., WO 05/056782).

In some embodiments, the detergent compositions described herein further comprise at least one chelating agent. Suitable chelating agents may include, but are not limited to copper, iron, and/or manganese chelating agents, and mixtures thereof. In embodiments in which at least one chelating agent is used, the detergent compositions comprise from about 0.1% to about 15% or even from about 3.0% to about 10% chelating agent by weight of composition.

In some still further embodiments, the detergent compositions described herein further comprise at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

In some embodiments, the detergent compositions described herein further comprise at least one anti-redeposition agent. In some embodiments, the anti-redeposition agent is a non-ionic surfactant, such as, for example, described in EP2100949.

In some embodiments, the detergent compositions described herein further comprise one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones, and polyvinylimidazoles, or mixtures thereof. In some embodiments, the detergent compositions described herein comprise from about 0.0001% to about 10%, from about 0.01% to about 5%, or even from about 0.1% to about 3% dye transfer inhibiting agent by weight of composition.

In some embodiments, the detergent compositions described herein further comprise one or more silicates. In some such embodiments, sodium silicates (e.g., sodium disilicate, sodium metasilicate, and crystalline phyllosilicates) find use. In some embodiments, the detergent compositions described herein comprise from about 1% to about 20% or from about 5% to about 15% silicate by weight of the composition.

In yet further embodiments, the detergent compositions described herein further comprise one or more dispersant. Suitable water-soluble organic materials include, but are not limited to the homo- or co-polymeric acids or their salts, in which the polycarboxylic acid comprises at least two carboxyl radicals separated from each other by not more than two carbon atoms.

In yet further embodiments, the detergent compositions described herein further comprise one or more bleach activator and/or bleach catalyst. Bleach activators are typically organic peracid precursors that enhance the bleaching action in the course of cleaning at temperatures of 60° C. and below. Bleach activators suitable for use herein include compounds which, under perhydrolysis conditions, give aliphatic peroxycarboxylic acids having preferably from about 1 to about 10 carbon atoms, in particular from about 2 to about 4 carbon atoms, and/or optionally substituted perbenzoic acid. Suitable bleach activators include, for example, those described in EP2100949. Bleach catalysts typically include, for example, manganese triazacyclononane and related complexes, and cobalt, copper, manganese, and iron complexes, as well as those described in U.S. Pat. Nos. 4,246,612; 5,227,084; 4,810,410; and WO99/06521 and EP2100949.

In some embodiments, fabric is exposed to a cellulase variant, or active fragment thereof, described herein prior to being worn such that removal of soil subsequently adhered to the fabric is improved in the first and/or subsequent two, three, or more wash cycles over soiled fabric that is not exposed to the cellulase variant, or active fragment thereof, described herein prior to being worn. In other embodiments, fabric is exposed to the cellulase variant, or active fragment thereof, described herein after being worn such that the removal of soil subsequently adhered to the fabric is improved in the first and/or subsequent two, three, or more wash cycles over soiled fabric that is not subsequently exposed to the cellulase variant, or active fragment thereof, described herein. In still further embodiments, cellulase variant, or active fragment thereof, described herein finds use in a detergent composition, a textile finishing process, or a paper and pulp process.

Yet another embodiment is directed to enhancing the feel and/or appearance and/or providing color enhancement and/or a stone washed appearance to a cellulose containing textile material (such as, for example, cotton, flax, ramie, jute, viscose, modified viscose fibers, lyocell and cupro) comprising treating the material with an effective amount of a cellulase variant, or active fragment thereof, described herein or a composition comprising an effective amount of a cellulase variant, or active fragment thereof, described herein. A still further embodiment is directed to a method for reducing color redeposition during the stone washing of colored fabrics comprising contacting the fabric with an effective amount of a cellulase variant, or active fragment thereof, described herein or a composition comprising an effective amount of a cellulase variant, or active fragment thereof, described herein under conditions sufficient to impart a stone-washed appearance to the fabric. In still another embodiment, a cellulose containing textile material treated with an effective amount of a cellulase variant, or active fragment thereof, described herein or a composition comprising an effective amount of a cellulase variant, or active fragment thereof, described herein retains substantially all of the material's tensile strength as compared to an untreated cellulose containing textile material. In yet still another embodiment, a cellulose containing textile material treated with an effective amount of a cellulase variant, or active fragment thereof, described herein or a composition comprising an effective amount of a cellulase variant, or active fragment thereof, described herein retains 50%, 60%, 70%, 80%, 90%, 91%, 92%, 93%, 94%, 95%, 96%, 97%, 98%, 99%, and 100% of the material's tensile strength as compared to an untreated cellulose containing textile material.

Other aspects and embodiments of the present compositions and methods will be apparent from the foregoing description and following examples. Various alternative embodiments beyond those described herein can be employed in practicing the invention without departing from the spirit and scope of the invention. Accordingly, the claims, and not the specific embodiments described herein, define the scope of the invention and as such methods and structures within the scope of the claims and their equivalents are covered thereby.

EXAMPLES

The following examples are provided to demonstrate and/or illustrate certain aspects of the present disclosure and should not be construed to limit the scope of the disclosure or any subsequently claimed invention.

Example 1

Assays

The following assays are standard assays used in the examples described below. Occasionally specific protocols called for deviations from these standard assays. In those cases, deviations from these standard assay protocols below are identified in the examples.

Performance Index

The performance index (PI) of an enzyme compares the performance of the variant (measured value) with a parent or reference polypeptide (theoretical or measured value) at the same protein concentration. Theoretical concentrations for the parent or reference polypeptide can be calculated using the parameters extracted from a Langmuir fit of a standard curve of the parent enzyme. A performance index (PI) that is greater than 1 (PI>1) indicates improved performance by a variant as compared to the parent or reference polypeptide, while a PI of 1 (PI=1) identifies a variant that performs the same as the parent or reference polypeptide, and a PI that is less than 1 (PI<1) identifies a variant that does not perform as well as the parent or reference polypeptide. For example, the STCE1 wild-type (STCE1-WT) mature protein set forth as SEQ ID NO:1 is the parent.

Protein Determination Assay (A280)

Absorbance at 280 nm was measured for purified enzyme samples in microtiter plates (Costar 3635, Sigma/Aldrich, USA) using a SpectraMax plate reader (Molecular Devices, USA). The responses of the STCE1-WT standards (standard protein ranges 50 ppm to 1000 ppm) were used to plot a standard curve. Absorbance values of variant samples were then interpolated from those graphs.

Protein Determination Assay (HPLC)

For high resolution concentration determinations, high performance liquid chromatography (HPLC) method was performed on protein samples. An Agilent 1290 U (HPLC) equipped with a Zorbax C-3 column was used for protein quantitation. Samples were eluted from the column using a gradient of 0.1% trifluoroacetic acid (TFA) in water and 0.07% TFA in acetonitrile. Absorbance was measured at 220 nm, and peaks were integrated using ChemStation software (Agilent Technologies, USA). The protein concentrations of the samples were calculated based on a standard curve of the purified STCE1-WT mature protein (SEQ ID NO:1).

Cellulase Activity Assay Using PAHBAH Reagent

The activity of cellulase enzymes was tested on carboxymethyl cellulose (CMC) substrate using the 4-hydroxybenzoic acid hydrazide (PAHBAH) reagent. The enzymatic activity was based on the hydrolysis of CMC substrate into reducing sugars followed by the detection of the new reducing ends by the PAHBAH reagent. The reagent PAHBAH stock solution (Sigma-Aldrich, USA) was prepared as 5% solution in 0.5 N hydrochloric acid (HCL). The PAHBAH reagent was further diluted in 0.5 M sodium hydroxide (NaOH) in 1:4 ratios to make up a final 1% solution. 1% CMC substrate was made in 50 mM HEPES buffer solution, pH 8.2. The enzyme samples (6 μL), adjusted to pH 8.2 were added to a microtiter plates (MTP) containing 40 μl of the 1% CMC solution and incubated at 40° C. in iEMS™ Microplate Incubator/Shaker HT (ThermoFisher Scientific Inc, USA) for 15 min; then 8 μl of enzyme-substrate mix was transferred to a new MTP containing 20 μl of 1% PAHBAH per well and incubated at 95° C. in a thermocycler machine (Eppendorf™ Mastercycler™ pro PCR system, Thermo Fisher Scientific, USA) for 5 min. Finally, 20 μl of each reaction solution was transferred to a fresh MTP and the absorbance was measured at 410 nm using a SpectraMax plate reader.

Cellulase Stability Assays

Cellulase enzyme samples were tested under three stability conditions as set forth on Table 1: thermostability, stability in the presence of protease, and stability in the presence of detergent and protease. The stressed and unstressed cellulase activities were measured using the cellulase activity assay described above and the ratio of stressed over unstressed was used to determine residual enzyme activity. The protease used in the assays was commercially available BPN'-Y217L subtilisin, which is forth as SEQ ID NO:2. Prior to using commercially available detergent in the stability assays, the enzymes contained in the detergent were inactivated by heating the detergent in a water bath set to 100° C. for 2 hrs.

TABLE 1

Conditions for cellulase stability assays

| Measurement | Condition | Stress temperature (° C.) and incubation time |
|---|---|---|
| Thermostability | 50 mM HEPES buffer pH 8.2 | 80° C. for 10 min |
| Stability in the presence of Protease | 1500 ppm BPN'-Y217L protease in 50 mM HEPES buffer pH 8.2 | 65° C. for 15 min |
| Stability in the presence of detergent and protease | 1% OMO Klein & Krachtig* plus 1000 ppm BPN'-Y217L protease in 50 mM HEPES buffer pH 8.2 | 37° C. for 24 hr |

* Heavy-duty liquid laundry detergent commercially sold by Unilever

For the unstressed test conditions, the test samples were not incubated prior to assaying for activity.

For the stressed test conditions, the test samples were prepared in 96 well PCR/MTP plates, sealed, and incubated at the elevated temperatures and under the conditions described in Table 1 using: an Eppendorf™, 384 MasterCycler™ Pro Thermocycler to measure thermostability, and stability in the presence of protease, or an iEMS incubator to measure stability in the presence of detergent and protease. After the various incubation periods, the samples were assayed for cellulase activity.

The residual activity of the enzyme sample tested in each assay was calculated as the mean of three replicates with blank subtracted. The relative residual activity of each enzyme sample was calculated as the ratio between residual activity and unstressed activity. The relative residual activity percentage was calculated by multiplying the relative residual activity number by 100. The PI of each STCE1-WT variant was calculated as the ratio between relative residual activity for the variant and relative residual activity for the STCE1-WT cellulase.

Example 2

Expression of Various GH45 Cellulases and Variants Thereof

The gene encoding the STCE1-WT cellulase (previously described as a family 45 glycoside hydrolase in the publication, Koga, J., Y. Baba, A. Shimonaka, T. Nishimura, S. Hanamura and T. Kono (2008), "Purification and characterization of a new family 45 endoglucanase, STCE1, from Staphylotrichum coccosporum and its overproduction in Humicola insolens." Appl. Environ. Microbiol. 74(13): 4210-4217) was selected as a template for generating the parent cellulase and variants thereof).

Figure 1:
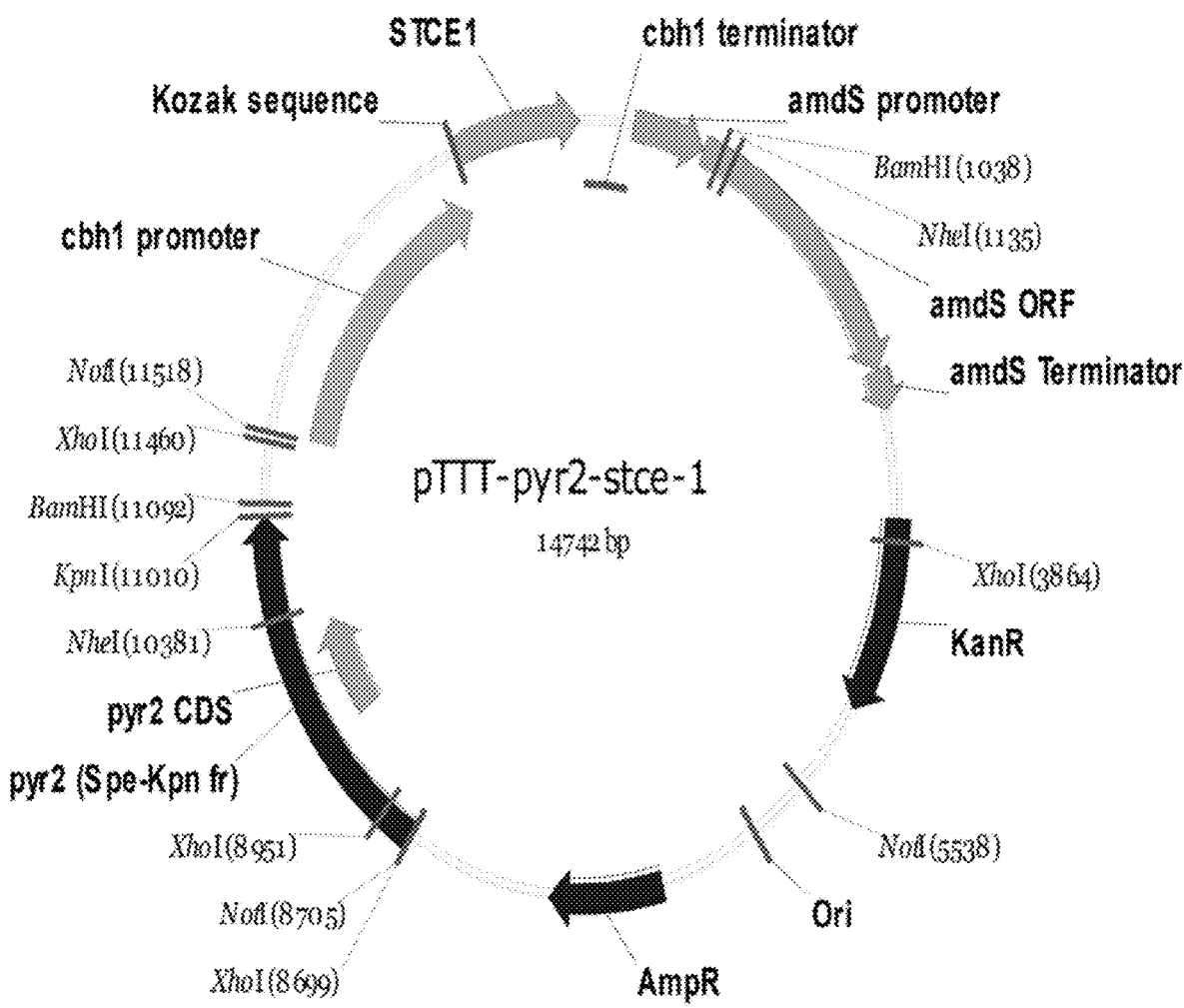
FIG. 1 provides a plasmid map of pTTT-pyr2-stce1.

The stce1 gene encoding the wildtype (WT) form of the protein (also referred to herein as the parent), contained an intron within the coding DNA. The intron was removed by using (i) a forward primer with the sequence set forth as SEQ ID NO:3, (ii) a reverse primer with the sequence set forth as SEQ ID NO:4, and (iii) the QuikChange® II XL Site-Directed Mutagenesis Kit (Stratagene, Agilent Technologies, USA). The resulting product was sub-cloned into the expression vector pTTT-pyr2 utilizing standard reagents. The pTTTpyr2 vector is similar to the pTTTpyrG vector described previously, for example, in WO2011153449A1 except that the A. nidulans pyrG gene is replaced with the H. jecorina pyr2 gene. The pTTT-pyr2 expression vector contained the T. reesei cbhI-derived promoter (cbhI) and cbhI terminator regions allowing for a strong inducible expression of the gene of interest, the A. nidulans amdS and pyr2 selective markers conferring growth of transformants on acetamide as a sole nitrogen source, and the T. reesei telomere regions allowing for non-chromosomal plasmid maintenance in a fungal cell. A map of the pTTT-pyr2 based vector containing the stce1-WT cellulase gene (set forth as SEQ ID NO:5), pTTT-pyr2-stce1 is shown in FIG. 1.

Using molecular biology techniques known in the art, multiple amino acid mutations (substitutions, insertions, and/or deletions) were introduced into the stce1 gene coding region. Additional expression vectors based on the pTTT-pyr2-stce1 platform where generated to encode these STCE-1 variants. Protoplasts of a suitable Trichoderma reesei host strains were transformed by the PEG based protocol described in U.S. Pat. No. 8,679,792 with the plasmid encoding each of the desired genes. After growth of transformants, spores from each well were pooled and re-patched using minimal medium containing acetamide as a sole nitrogen source. Upon sporulation, spores were harvested and used for inoculation in Aachen medium. Cultures were incubated for 6 days at 28° C., 80% humidity and 50 mm shaking throw in a Multitron shaker incubator (Infors, Switzerland). The culture broth was filtered to collect the clarified supernatant for the samples of interest, which were stored at −20° C. before assays were performed.

The nucleotide sequence of the stce1-WT gene in the pTTT-pyr2-STCE1 vector is set forth as SEQ ID NO:5 (951 base pairs). The amino acid sequence of the translation product of the stce1-WT gene is set forth as SEQ ID NO:6 (316 amino acids), wherein the N-terminal 21 amino acids constitute the signal peptide. The amino acid sequence of the mature form of STCE1-WT protein is set forth as SEQ ID NO:1 (295 amino acids), wherein the C-terminal 37 amino constitute the carbohydrate binding module (CBM).

The mutations (insertions, substitutions, and/or deletions) of the STCE1-WT variant cellulases tested herein are listed in Table 2 with the associated amino acid sequence of each variant set forth in SEQ TD NOs:7-69, wherein the amino acid positions of each variant are numbered by correspondence with the amino acid sequence of SEQ ID NO: 1.

TABLE 2

| Variant | Amino Acid Mutations (insertions, substitutions, deletions) of the STCE1-WT Cellulase Variants | Amino acid length | SEQ ID NO |
|---|---|---|---|
| STCE1-5217 | K4V-Q36T-S77M-T102K-Q154E-N178H-S225K and deletions: S232, T233, S234, T235, T236, S237, T238, K239, A240, T241, S242, and T243 | 283 | 7 |

TABLE 2-continued

| Variant | Amino Acid Mutations (insertions, substitutions, deletions) of the STCE1-WT Cellulase Variants | Amino acid length | SEQ ID NO |
|---|---|---|---|
| STCE1-5504 | K4V-K44V-S77K-E90A-S135T-A142P-Q154E-L192V-V208H-S221L-A247T and deletions: S232, T233, S234' T235, T236, S237, T238, K239, A240, T241, S242, and T243 | 283 | 8 |
| STCE1-5267 | K4V-N80S-G87A-Q154E-A161P-G204S-S221L and deletions: T233, S234, T235, T236, S237, T238, K239, A240, T241, S242, and T243 | 284 | 9 |
| STCE1-5349 | S32Y-T102K-A142P-G204S-V208H-A247T and deletions: T233, S234, T235, T236, S237, T238, K239, A240, T241, S242, and T243 | 284 | 10 |
| STCE1-5434 | K4V-K44V-S77K-N80S-T102K-G112T-S135T-A142P-L192V and deletions: T233, S234, T235, T236, S237, T238, K239, A240, T241, S242, and T243 | 284 | 11 |
| STCE1-5443 | S77M-Ai42P-K163V-V208H-A247T and deletions: T233, S234, T235, T236, S237, T238, K239, A240, T241, S242, and T243 | 284 | 12 |
| STCE1-5286 | S77M-G87A-A99H-G112T-A142P-S232T-T236A and deletion: T233 | 294 | 13 |
| STCE1-5324 | S23L-A142P-D202E-S232T and deletion: T233 | 294 | 14 |
| STCE1-5207 | Q36T-S77K-G87A-A142P-S153D-A161P-G204S-S221L-S237D | 295 | 15 |
| STCE-5219 | K4V-F29W-S77K-T102K-P136E-Si53D-A161P-T210V | 295 | 16 |
| STCE1-5225 | A99Y-G112T-S135T-S153D-K227R | 295 | 17 |
| STCE1-5238 | S23L-S32Y-G112T-A142P-A161P-G2045-5217G-K227R-5237D | 295 | 18 |
| STCE-5248 | F29W-Q36T-K44V-T116V-S135T-Q154E-A161P-5217G-5221L-5225K-T238D | 295 | 19 |
| STCE1-5250 | K4V-Q36T-577K-N805-A142P-L192V-G2045-T210V-5221L | 295 | 20 |
| STCE1-5258 | F29W-G87A-E90A-A99Y-A142P-S153D-K227R-S237D | 295 | 21 |
| STCE1-5276 | K4V-577M-Q154E-A161P-L192V-V208H-5217G-T233A-5237D | 295 | 22 |
| STCE1-5279 | E90A-G112T-S135T-A161P-G204S | 295 | 23 |
| STCE1-5281 | S51T-S77M-P136E-K163V-G204S-T210V-K227R | 295 | 24 |
| STCE1-5308 | K4V-F29W-S51T-T116V-S135T-S221L-S225K | 295 | 25 |
| STCE1-5316 | S77M-T102K-T116V-S135T-S153D-A161P-T238D | 295 | 26 |
| STCE1-5322 | K4V-S23L-S32Y-N80S-T102K-A142P-A161P-S237D | 295 | 27 |
| STCE1-5334 | K44V-G87A-Q154E-A161P | 295 | 28 |
| STCE1-5340 | S32Y-A142P-Q154E-K163V-S217G-K227R-T233A | 295 | 29 |
| STCE1 5354 | N34D-S51T-G87A-T102K-T116V-P136E-Q154E-A161P-L192V-T233A-T238D | 295 | 30 |
| STCE1-5379 | K4V-S77K-E90A-A142P-S157D-S217G-T233A-T238D and deletion: G214 | 295 | 31 |
| STCE1-5385 | K4V-Q36T-S51T-N80S-S135T-S157D-T233A | 295 | 32 |
| STCE1-5398 | Q36T-S77K-G87A-A142P-S153D-A161P-G204S-S221L-S237D and deletion: D177 | 295 | 33 |
| STCE1-5431 | K4V-S51T-V98G-S135T-Q154E-T233A | 295 | 34 |
| STCE1-5433 | T102K-A142P-Q154E-G204S-K227R | 295 | 35 |
| STCE1-5448 | S51T-G87A-A99Y-S135T-N205D-T238D | 295 | 36 |
| STCE1-5450 | G87A-A142P-A161P-L192V-G204S-T241A | 295 | 37 |
| STCE1-5452 | K4V-S77K-E90A-A142P-S157D-S217G-T233A-T238D | 295 | 38 |
| STCE-5458 | K4V-P136E-S153D-A161P-T210V-K227R | 295 | 39 |
| STCE1-5491 | S51T-N80S-A142P-L192V-V208H | 295 | 40 |
| STCE1-5500 | K4V-S23L-Q36T-S77M-G112T-S157D-A161P-L192V-S221L | 295 | 41 |
| STCE1-5539 | Q36T-V98Y-A142P-A161E-S225K | 295 | 42 |
| STCE1-5542 | Q36T-P136E-A142P-S225K-S249P | 295 | 43 |
| STCE1-5543 | A99Y-P136E-A142P-A161E-S221L | 295 | 44 |
| STCE1-5546 | S32D-Q36T-S221L-S225K | 295 | 45 |
| STCE1-5547 | S32D-A99Y-A142P-A161E-S249P | 295 | 46 |
| STCE1-5550 | K44V-A142P-A161P-K163V | 295 | 47 |
| STCE1-5552 | S32D-Q36T-G112S-A142P | 295 | 48 |
| STCE1-5557 | S32D-Q36T-S77M-S135T-A142P-A161P | 295 | 49 |
| STCE1-5560 | F29W-S77M-A99E-A142P | 295 | 50 |
| STCE1-5561 | G112S-P136K-A142E | 295 | 51 |
| STCE1-5562 | S135T-A142P-K163V | 295 | 52 |
| STCE1-5563 | K4V-G112S-S135T-A142P-A161P | 295 | 53 |
| STCE1-5567 | S32D-Q36T-A99E-P136K-A142P | 295 | 54 |
| STCE1-5575 | G112S-P136K-A142P-S217M-S221M-T241L-G258K | 295 | 55 |
| STCE1-5576 | K4V-S77K-G112S-A142P-A194S-S249G-G258K | 295 | 56 |
| STCE1-5609 | P97S-G112V-P136S-A142P-A161E-K163V-P212S-S222A | 295 | 57 |
| STCE1-5611 | P97S-G112V-P136S-S153D-A161E-S225K-T241R | 295 | 58 |
| STCE1-5612 | P97S-G112V-P136S-S153D-S225K-T241R | 295 | 59 |
| STCE1-5614 | S32D-A142E-V208K-S225K-T241R | 295 | 60 |
| STCE1-5616 | S32D-A142E | 295 | 61 |

TABLE 2-continued

| Variant | Amino Acid Mutations (insertions, substitutions, deletions) of the STCE1-WT Cellulase Variants | Amino acid length | SEQ ID NO |
|---|---|---|---|
| STCE1-5684 | S51T-A99Y-F119L-P136E-Q154E-D156G-S217G | 295 | 62 |
| STCE1-5343 | K44V-A142P-A161P-K163V-K227R-T236A | 295 | 63 |
| STCE1-5401 | G112T-S135T-Q154E-T233S-S237D and insertion after position 233: TTSTST | 295 | 64 |
| STCE1-5355 | Q36T-S51T-V98G-T116V-A142P-A161P-T233S and insertion after position 233: TASTKATSTT | 301 | 65 |
| STCE1-5287 | K4V-F29W-S51T-D65G-S77M-T116V-S153D-K163V-G204S-F206S-T210V-S221L and insertion after position 233: STTSTKATSTT | 305 | 66 |
| STCE1-5357 | S77M-S135T-Q154E-K163V-K227R-S237D and insertion after position 233: STTSDKATSTT | 306 | 67 |
| STCE1-5460 | K4V-S32G-Q36T-S77M-G87A-T116V-A142P-A161P and insertion after position 233: STTDTKATSTT S77M-G87A-P136E-S157D-S221L-T236A-T238D- | 306 | 68 |
| STCE1-5683 | K286E and insertion after position 233: STTSTKATSTT | 306 | 69 |

The STCE1-WT and variant cellulase proteins were purified by ammonium sulfate precipitation, adding 3M $(NH_4)_2SO_4$ to clarified culture broth in 1:1 dilution and using a Relisorb OC 400 resin (Resindon, Italy) in 20 mM $KH_2PO_4$, pH 6.0. The resin was washed with 20 mM $KH_2PO_4$ pH 6.0+0.5M $(NH_4)_2SO_4$ buffer and the proteins of interest were eluted in 20 mM $KH_2PO_4$ pH 6.0 buffer and stored at 4° C. until assayed.

Example 3

Stability of STCE1 Cellulase Variants

The STCE1-WT and the STCE1 variant cellulases listed on Table 1 were assayed for activity on CMC substrate at pH 8.2 as described in Example 1. The cellulase variants with at least 50% relative activity versus STCE1-WT cellulase were further studied to measure stability under the test conditions described in Example 1, including: thermostability, stability in the presence of a protease, and stability in the presence of protease and detergent. The relative stability performance results are shown in Table 2, reported as PI of STCE1 cellulase variants versus STCE1-WT.

TABLE 2

PI of STCE1 Cellulase Variants With Improved Stability

| Protein ID | Detergent (OMO) and Protease | Protease | Thermal |
|---|---|---|---|
| STCE1-WT | 1.0 | 1.0 | 1.0 |
| STCE1-5207 | 7.1 | 9.3 | 1.5 |
| STCE1-5217 | 2.4 | 1.5 | 1.5 |
| STCE1-5219 | 3.7 | 5.5 | 1.3 |
| STCE1-5225 | 2.3 | 0.6 | 1.3 |
| STCE1-5238 | 6.9 | 5.8 | 1.3 |
| STCE1-5248 | 5.8 | 3.1 | 1.4 |
| STCE1-5250 | 6.8 | 4.6 | 1.3 |
| STCE1-5258 | 6.5 | 5.7 | 1.3 |
| STCE1-5267 | 3.2 | 2.5 | 1.5 |
| STCE1-5276 | 3.2 | 0.8 | 1.5 |
| STCE1-5279 | 4.3 | 1.3 | 1.5 |
| STCE1-5281 | 2.2 | 0.5 | 1.4 |
| STCE1-5286 | 6.9 | 6.9 | 1.4 |
| STCE1-5287 | 2.4 | 1.4 | 1.2 |
| STCE1-5308 | 1.8 | 0.7 | 1.3 |
| STCE1-5316 | 5.2 | 4.2 | 1.4 |
| STCE1-5322 | 7.0 | 7.0 | 1.3 |
| STCE1-5324 | 6.9 | 1.5 | 1.3 |
| STCE1-5334 | 2.6 | 0.9 | 1.4 |
| STCE1-5340 | 6.3 | 1.2 | 1.2 |
| STCE1-5343 | 6.8 | 1.4 | 1.4 |
| STCE1-5349 | 6.5 | 1.1 | 1.4 |
| STCE1-5354 | 5.7 | 6.7 | 1.5 |
| STCE1-5355 | 6.8 | 0.5 | 1.3 |
| STCE1-5357 | 6.2 | 2.0 | 1.4 |
| STCE1-5379 | 4.7 | 3.1 | 1.4 |
| STCE1-5385 | 2.1 | 0.8 | 1.4 |
| STCE1-5398 | 4.6 | 7.3 | 1.4 |
| STCE1-5401 | 3.3 | 1.1 | 1.4 |
| STCE1-5431 | 3.0 | 0.6 | 1.4 |
| STCE1-5433 | 4.2 | 2.8 | 1.5 |
| STCE1-5434 | 4.6 | 6.6 | 1.4 |
| STCE1-5443 | 4.8 | 0.6 | 1.2 |
| STCE1-5448 | 1.8 | 0.6 | 1.5 |
| STCE1-5450 | 4.5 | 4.1 | 1.5 |
| STCE1-5452 | 4.7 | 4.2 | 1.4 |
| STCE1-5458 | 3.3 | 1.5 | 1.4 |
| STCE1-5460 | 4.4 | 7.4 | 1.5 |
| STCE1-5491 | 4.6 | 1.8 | 1.3 |
| STCE1-5500 | 1.8 | 0.9 | 1.6 |
| STCE1-5504 | 4.9 | 2.7 | 1.4 |
| STCE1-5539 | 4.5 | 1.3 | 1.4 |
| STCE1-5542 | 3.5 | 3.0 | 1.3 |
| STCE1-5543 | 4.2 | 0.9 | 1.2 |
| STCE1-5546 | 4.9 | 5.1 | 1.3 |
| STCE1-5547 | 4.9 | 3.4 | 1.2 |
| STCE1-5550 | 4.7 | 4.7 | 1.4 |
| STCE1-5552 | 5.0 | 6.6 | 1.3 |
| STCE1-5557 | 4.1 | 7.4 | 1.5 |
| STCE1-5560 | 4.6 | 2.6 | 1.4 |
| STCE1-5561 | 2.4 | 1.8 | 1.3 |
| STCE1-5562 | 4.6 | 3.3 | 1.3 |
| STCE1-5563 | 4.8 | 7.0 | 1.4 |
| STCE1-5567 | 4.0 | 6.8 | 1.3 |
| STCE1-5575 | 3.7 | 6.1 | 1.1 |
| STCE1-5576 | 5.3 | 5.2 | 1.3 |
| STCE1-5609 | 4.2 | 0.6 | 1.3 |
| STCE1-5611 | 3.6 | 0.8 | 1.4 |
| STCE1-5612 | 2.5 | 0.9 | 1.4 |
| STCE1-5614 | 3.9 | 1.9 | 1.3 |
| STCE1-5616 | 3.7 | 1.9 | 1.3 |
| STCE1-5683 | 6.6 | 7.2 | 1.4 |
| STCE1-5684 | 3.0 | 2.4 | 1.4 |

The following substitutions: 142P, 161P, 4V, 36T, 87A, 154E, 135T, 204S, 77K, 102K, 77M, 153D, 221L, 32D, 136E, 192V, 227R, 29W, 90A, 112T, 116V, 217G, 225K, 51T, 80S, 112S, 163V, 210V were observed with high frequency among the STCE1 cellulase variants with improved stability (Table 2). These results suggest a stability benefit was introduced by these amino acid substitutions. Furthermore, the following sets of substitutions were observed with high frequency: 142P+161P, 4V+142P, 36T+142P, 4V+77K, 77K+142P, 87A+142P, 87A+161P, 142P+204S, 4V+161P, 161P+204S, 102K+161P, 142P+192V, 142P+227R, 153D+161P, 4V+102K, 4V+210V, 29W+153D, 32D+142P, 36T+161P, 36T+221L, 36T+225K, 87A+204S, 90A+142P, 116V+161P, 135T+142P, 135T+154E, 135T+161P, 136E+161P, 204S+221L, 4V+80S, 4V+153D, 4V+221L, 32D+36T, 32Y+142P, 77M+142P, 77K+153D, 77K+161P, 77K+221L, 80S+142P, 87A+153D, 87A+192V, 87A+221L, 102K+136E, 102K+142P, 102K+154E, 112T+135T, 112S+142P, 142P+153D, 142P+217G, 142P+221L, 153D+210V, 154E+161P, 161P+192V, and 161P+221L.

Example 4

Alignment of GH45 Cellulases with STCE1-Variants

An alignment of the amino acid sequences of the following cellulases: STCE1-WT (SEQ ID NO:1), C_thermophilum (NCBI Accession NO: AGY80101.1, residues 1-293) (SEQ ID NO:70), H_insolens (NCBI Accession No: CAA01574.1, residues 22-305) (SEQ ID NO:71), H_grisea (NCBI Accession No: BAA74956.1, residues 22-305) (SEQ ID NO:72), T_terrestris (NCBI Accession No: XP_003651003.1, residues 22-299) (SEQ ID NO:73), A_thermophilum (accession No: ACE10216; SEQ ID NO:6 in U.S. Pat. No. 7,361,487, residues 22-315)(SEQ ID NO:74), N_crassa (NCBI Accession No: XP_957107, residues 22-293) (SEQ ID NO:75), and the cellulase variants listed on Table 1 (SEQ ID NOs:7-68) was generated. The sequences were aligned with default parameters using the MUSCLE program from Geneious software (Biomatters Ltd.) (Robert C. Edgar. MUSCLE: multiple sequence alignment with high accuracy and high throughput Nucl. Acids Res. (2004) 32 (5): 1792-1797). Based on previous structure function analysis of the GH45 cellulases, such as the crystal structure of H. insolens cellulase (pdb ID 3ENG), the regions comprising the catalytic core, linker and C-terminal were defined with the catalytic core region set forth in FIGS. 2A-2H, the linker region set forth in FIGS. 3A-3B, and the C-terminal region set forth in FIGS. 4A-4B.

The catalytic core contains residues that correspond to positions 1-211 of the mature STCE1-WT cellulase set forth in SEQ ID NO:1, wherein the amino acid positions are numbered by correspondence with the amino acid sequence of SEQ ID NO:1. The alignment of the residues within this catalytic core region is shown in FIGS. 2A-2H.

Figure 3A:
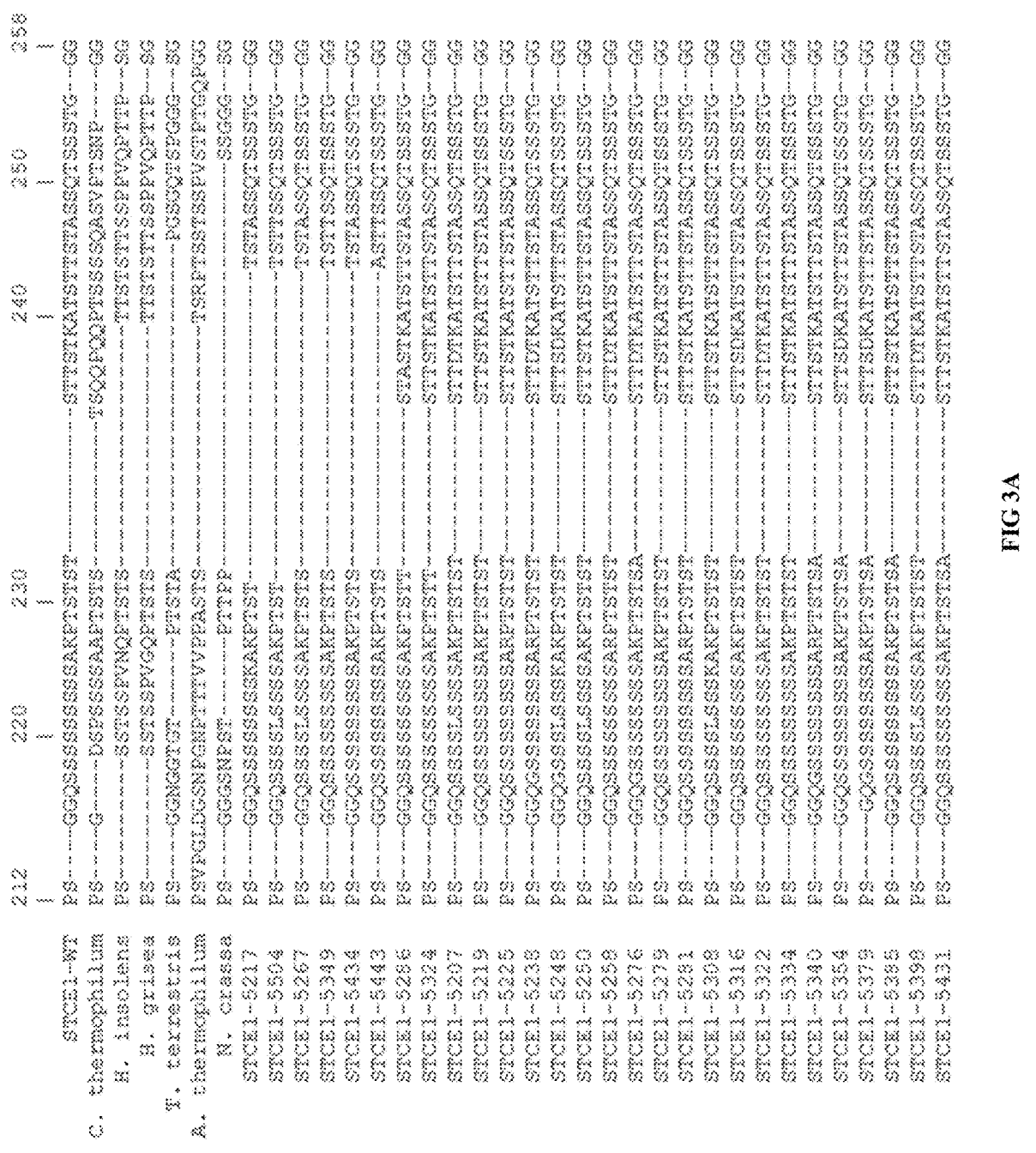

Residues P212, S213, G258 and C259 are fully conserved across all the studied cellulases, and anchor a highly variable region of varying length across all the GH45 cellulase sequences examined. Therefore, the linker region contains residues that are present between the residues corresponding to P212 and G258 of the mature STCE1-WT cellulase set forth in SEQ ID NO:1, wherein the amino acid positions are numbered by correspondence with the amino acid sequence of SEQ ID NO:1. The alignment of the residues within this linker region is shown in FIGS. 3A-3B. For the proteins evaluated in this study, the length of the linker present between the residues corresponding to positions 212 and 258 of the mature STCE1-WT cellulase set forth in SEQ ID NO:1 (wherein the amino acid positions are numbered by correspondence with the amino acid sequence of SEQ ID NO:1) ranges from 19 to 55 amino acids, where the STCE1-WT linker contains 44 residues and the mean length of the linker across the studied cellulases is 40.

Figure 4A:
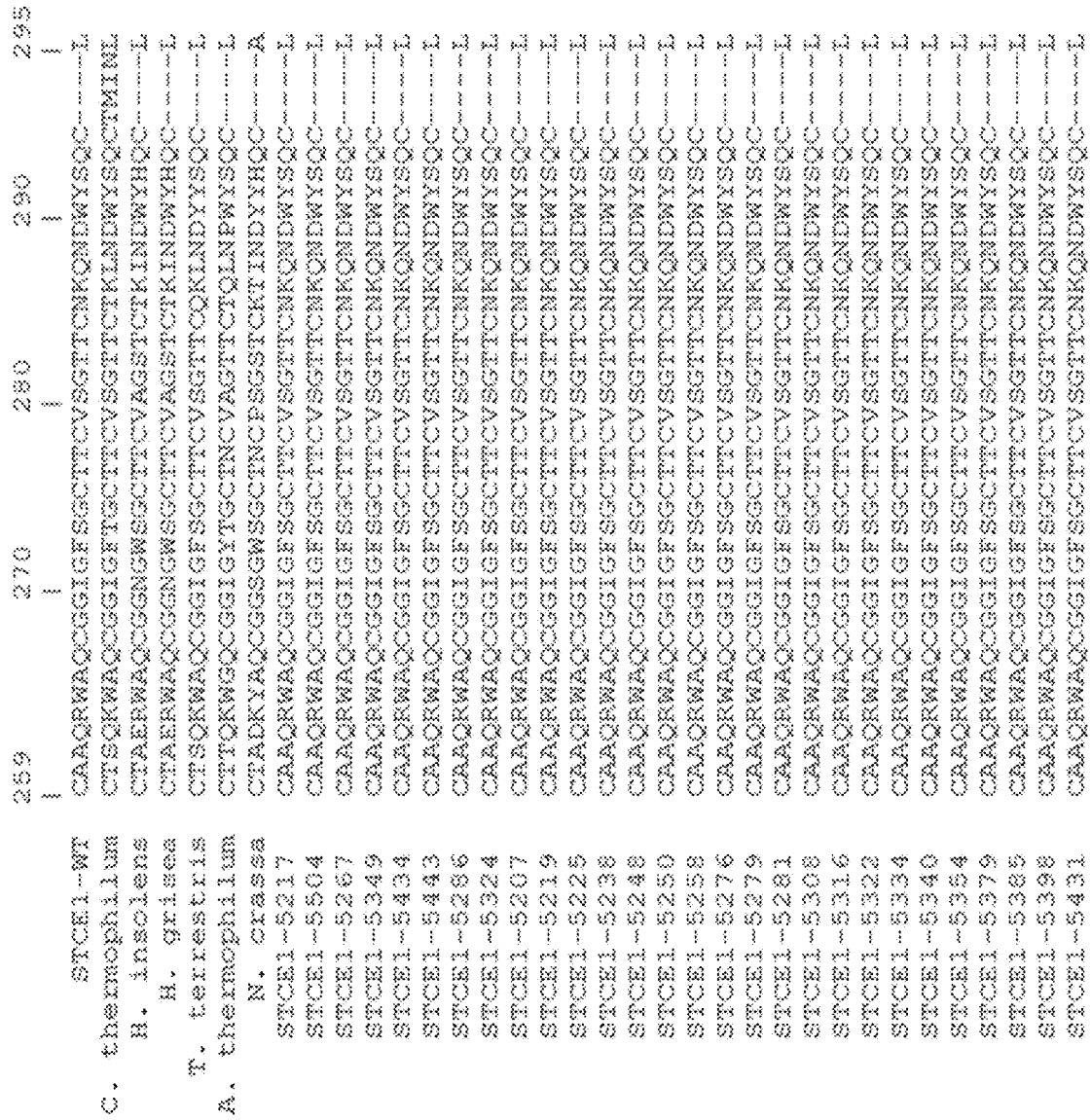

The C-terminal region contains the residues that are present between the residues corresponding to positions 259 and 295 of the mature STCE1-WT cellulase set forth in SEQ ID NO:1, wherein the amino acid positions are numbered by correspondence with the amino acid sequence of SEQ ID NO:1. The alignment of the residues within this C-terminal region is shown in FIGS. 4A-4B.

We claim:

1. A cellulase variant, comprising an amino acid sequence comprising two or more mutations at two or more positions corresponding to SEQ ID NO:1
wherein said two or more mutations comprise a threonine at position 36 and at least one additional mutation at a position selected from 4, 23, 29, 32, 34, 44, 51, 65, 77, 80, 87, 90, 97, 98, 99, 102, 112, 116, 119, 135, 136, 142, 153, 154, 156, 157, 161, 163, 178, 192, 194, 202, 204, 205, 206, 208, 210, 212, 217, 221, 222, 225, 227, 232, 233, 236, 237, 238, 241, 247, 249, and 258,
wherein said variant has endoglucanase activity, wherein said variant has an amino acid sequence having at least 90% amino acid sequence identity to the amino acid sequence of SEQ ID NO:1, and wherein the amino acid positions of the variant, are numbered by correspondence with the amino acid sequence of SEQ ID NO:1.

2. The cellulase variant of claim 1, wherein said two or more mutations at two or more positions corresponding to two or more SEQ ID NO: 1 positions are selected from:
Q36T+A142P, Q36T+A161P, Q36T+S221L, Q36T+S225K, S32D+Q36T.

3. The cellulase variant, of claim 1, wherein said variant further comprises one or more mutations selected from:
(i) a deletion of one or more amino acid residues at one or more positions corresponding to any SEQ ID NO:1 position between positions 213 and 257;
(ii) a deletion of one or more amino acid residues at one or more positions corresponding to SEQ ID NO: 1 positions selected from D177, S232, T233, S234, T235, T236, S237, T238, K239, A240, T241, S242, and T243;
(iii) a deletion of one or more amino acid residues at one or more positions corresponding to SEQ ID NO: 1 positions selected from D177, S232, T233, S234, T235, T236, S237, T238, K239, A240, T241, S242, and T243, wherein said deletions are selected from D177Z, T233Z, T233Z-S234Z-T235Z-T236Z-S237Z-T238Z-K239Z-A240Z-T241Z-S242Z-T243Z, and S232Z-T233Z-S234Z-T235Z-T236Z-S237Z-T238Z-K239Z-A240Z-T241Z-S242Z-T243Z;
(iv) an insertion of one, two, three, four, five, six, or more amino acid residues after a position corresponding to position 233 of SEQ ID NO:1;
(v) an insertion of one, two, three, four, five, six, or more amino acid residues after a position corresponding to position 233 of SEQ ID NO:1, wherein said insertion is selected from Z233.01T-Z233.02T-Z233.03S-Z233.04T-Z233.05S-Z233.06T, Z233.01T-Z233.02A-Z233.03S-Z233.04T-Z233.05K-Z233.06A-Z233.07T-Z233.08S-Z233.09T-Z233.10T, Z233.01S-Z233.02T-Z233.03T-Z233.04S-Z233.05D-Z233.06K-Z233.07A-Z233.08T-Z233.09S-Z233.10T-Z233.11T, Z233.01S-Z233.02T-Z233.03T-Z233.04D-Z233.05T-Z233.06K-Z233.07A-Z233.08T-Z233.09S-Z233.10T-Z233.11T, and Z233.01S-Z233.02T-Z233.03T-Z233.04S-Z233.05T-Z233.06K-Z233.07A-Z233.08T-Z233.09S-Z233.10T-Z233.11T; and
(vi) a combination of (i) to (v).

4. The cellulase variant of claim 1, wherein said two or more mutations at two or more positions corresponding to two or more SEQ ID NO: 1 positions are selected from: K4V-Q36T-S77M-T102K-Q154E-N178H-S225K-S232Z-T233Z-S234Z-T235Z-T236Z-S237Z-T238Z-K239Z-A240Z-T241Z-S242Z-T243Z, Q36T-S77K-G87A-A142P-S153D-A161P-G204S-S221L-S237D, F29W-Q36T-K44V-T116V-S135T-Q154E-A161P-S217G-S221L-S225K-T238D, K4V-Q36T-S77K-N80S-A142P-L192V-G204S-T210V-S221L, K4V-Q36T-S51T-N80S-S135T-S157D-T233A, K4V-S23L-Q36T-S77M-G112T-S157D-A161P-L192V-S221L, Q36T-V98Y-A142P-A161E-S225K, Q36T-P136E-A142P-S225K-S249P, S32D-Q36T-S221L-S225K, S32D-Q36T-G112S-A142P, S32D-Q36T-S77M-S135T-A142P-A161P, Q36T-S51T-V98G-T116V-A142P-A161P-T233S-Z233.01T-Z233.02A-Z233.03S-Z233.04T-Z233.05K-Z233.06A-Z233.07T-Z233.08S-Z233.09T-Z233.10T, Q36T-S77K-G87A-A142P-S153D-A161P-D177Z-G204S-S221L-S237D, and K4V-S32G-Q36T-S77M-G87A-T116V-A142P-A161P-Z233.01S-Z233.02T-Z233.03T-Z233.04D-Z233.05T-Z233.06K-Z233.07A-Z233.08T-Z233.09S-Z233.10T-Z233.11T.

5. The cellulase variant of claim 1, with the proviso that one or more of said mutations is non-naturally occurring.

6. The cellulase variant of claim 1, wherein said variant has at least one improved property selected from improved thermostability, stability in the presence of one or more protease, and stability in the presence of one or more protease and one or more other detergent component when compared to a parent or reference polypeptide.

7. The cellulase variant of claim 1, wherein said variant is derived from a parent or reference polypeptide selected from SEQ ID NOs: 1, 70, 71, 72, 73, 74, and 75.

8. The cellulase variant of claim 1, wherein the improved property is (i) improved thermostability and wherein said variant has a thermal PI that is greater than 1 or ≥1.1; (ii) improved stability in the presence of one or more protease and wherein said variant has a PI that is greater than 1 or ≥1.1, 1.2, 1.3, 1.4, 1.5, or 2.0 when the stability of said variant is tested in the presence of said protease; and/or (iii) improved stability in the presence of one or more protease and one or more other detergent component, and wherein said variant has a PI that is greater than 1 or ≥1.1, 1.5, 2.0, or 2.5 when the stability of said variant, is tested in the presence of said protease and said other detergent component.

9. The cellulase variant of claim 8, wherein the PI is measured in accordance with the Cellulase Activity Assay.

10. The cellulase variant of claim 8, wherein the other detergent component is a surfactant.

11. The cellulase variant of claim 1, wherein said variant is a family GH45 cellulase.

12. A composition comprising the cellulase variant of claim 1.

13. The composition of claim 12, wherein said composition is selected from an enzyme composition, detergent composition, and fabric care composition.

14. The composition of claim 12, further comprising (i) one or more other enzymes selected from the group consisting of acyl transferases, amylases, alpha-amylases, beta-amylases, alpha-galactosidases, arabinases, arabinosidases, aryl esterases, beta-galactosidases, beta-glucanases, carrageenases, catalases, chondroitinases, cutinases, endo-beta-mannanases, exo-beta-mannanases, esterases, exo-mannanases, galactanases, glucoamylases, hemicellulases, hyaluronidases, keratinases, laccases, lactases, ligninases, lipases, lipolytic enzymes, lipoxygenases, mannanases, metalloproteases, oxidases, oxidoreductases, pectate lyases, pectin acetyl esterases, pectinases, pentosanases, perhydrolases, peroxidases, phenoloxidases, phosphatases, phospholipases, phytases, polyesterases, polygalacturonases, proteases, pullulanases, reductases, rhamnogalacturonases, second cellulase, beta-glucanases, tannases, transglutaminases, xylan acetyl-esterases, xylanases, and xylosidases; (ii) one or more surfactants; (iii) one or more ions selected from calcium and zinc; (iv) one or more adjunct ingredients; (v) one or more stabilizers; (vi) from about 0.001% to about 5.0 weight % of said cellulase variant; (vii) one or more bleaching agents; and/or (viii) combinations thereof.

15. The composition of claim 12, wherein said composition is a laundry detergent.

16. The composition of claim 12, wherein the composition is in a form selected from a liquid, a powder, a granulated solid, a tablet, a sheet, and a unit dose.

17. The composition of claim 12, wherein said composition contains phosphate or is phosphate-free and/or contains boron or is boron-free.

18. A polynucleotide comprising a nucleic acid sequence encoding the cellulase variant of claim 1.

19. An expression vector comprising the polynucleotide of claim 18.

20. A host cell comprising the expression vector of claim 19.

21. A method for producing the cellulase variant, comprising: (a) stably transforming a host cell with the expression vector of claim 19; (b) cultivating said transformed host cell under conditions suitable for said host cell to produce said cellulase variant; and (c) recovering said cellulase variant.

* * * * *

SEQUENCE LISTING

<160> NUMBER OF SEQ ID NOS: 75

<210> SEQ ID NO 1
<211> LENGTH: 295
<212> TYPE: PRT
<213> ORGANISM: Staphylotrichum coccosporum

<400> SEQUENCE: 1

```
Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
            85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
```

```
            115                 120                 125
Gly Ile Phe Asp Gly Cys Ser Pro Gln Phe Gly Gly Leu Ala Gly Asp
    130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Ser Thr Thr Ser Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
    290                 295

<210> SEQ ID NO 2
<211> LENGTH: 338
<212> TYPE: PRT
<213> ORGANISM: artificial sequence
<220> FEATURE:
<223> OTHER INFORMATION: BPN' protein variant

<400> SEQUENCE: 2

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
```

```
                180                 185                 190
Gly Pro Glu Leu Asp Val Met Ala Pro Gly Val Ser Ile Gln Ser Thr
                195                 200                 205

Leu Pro Gly Asn Lys Tyr Gly Ala Leu Asn Gly Thr Ser Met Ala Ser
            210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln Lys Ser Phe Pro Glu Val Val Gly Lys Thr Val Asp Gln
        275                 280                 285

Ala Arg Glu Tyr Phe Thr Leu His Tyr Pro Gln Tyr Asp Val Tyr Phe
            290                 295                 300

Leu Pro Glu Gly Ser Pro Val Thr Leu Asp Leu Arg Tyr Asn Arg Val
305                 310                 315                 320

Lys Val Phe Tyr Asn Pro Gly Thr Asn Val Val Asn His Val Pro His
                325                 330                 335

Val Gly

<210> SEQ ID NO 3
<211> LENGTH: 42
<212> TYPE: DNA
<213> ORGANISM: artificial sequence
<220> FEATURE:
<223> OTHER INFORMATION: forward primer

<400> SEQUENCE: 3
gtggtgctgt ggctgctacg agctgacctt cacctcgggc cc                42

<210> SEQ ID NO 4
<211> LENGTH: 42
<212> TYPE: DNA
<213> ORGANISM: artificial sequence
<220> FEATURE:
<223> OTHER INFORMATION: reverse primer

<400> SEQUENCE: 4
gggcccgagg tgaaggtcag ctcgtagcag ccacagcacc ac                42

<210> SEQ ID NO 5
<211> LENGTH: 951
<212> TYPE: DNA
<213> ORGANISM: Staphylotrichum coccosporum

<400> SEQUENCE: 5
atgcgttcct cccccgtcct ccgcacggcc ctggccgctg ccctccccct ggccgccctc    60
gctgccgatg caagtcgac ccgctactgg gactgttgca agccgtcgtg ctcgtggccc    120
ggcaaggcct cggtgaacca gcccgtcttc gcctgcagcg ccaacttcca gcgcatcagc    180
gaccccaacg tcaagtcggg ctgcgacggg ggctccgcct acgcctgcgc cgaccagacc    240
ccgtgggccg tcaacgacaa cttctcgtac ggcttcgccg ccacgtccat ctcgggcggc    300
aacgaggcct cgtggtgctg tggctgctac gagctgacct tcacctcggg ccccgtcgct    360
ggcaagacca tggttgtcca gtccaccctcg accggcggcg acctcggcac caaccacttc    420
gacctggcca tgcccggtgg tggtgtcggc atcttcgacg gctgctcgcc ccagttcggc    480
```

```
ggcctcgccg gcgaccgcta cggcggcgtc tcgtcgcgca gccagtgcga ctcgttcccc      540
gccgccctca agcccggctg ctactggcgc ttcgactggt tcaagaacgc cgacaacccg      600
accttcacct tccgccaggt ccagtgcccg tcggagctcg tcgcccgcac cggctgccgc      660
cgcaacgacg acggcaactt ccccgtcttc acccctccct cgggcggtca gtcctcctcg      720
tcttcctcct ccagcagcgc caagcccacc tccacctcca cctcgaccac ctccaccaag      780
gctacctcca ccacctcgac cgcctccagc cagacctcgt cgtccaccgg cggcggctgc      840
gccgcccagc gctgggcgca gtgcggcggc atcgggttct cgggctgcac cacgtgcgtc      900
agcggcacca cctgcaacaa gcagaacgac tggtactcgc agtgcctttg a              951
```

<210> SEQ ID NO 6
<211> LENGTH: 316
<212> TYPE: PRT
<213> ORGANISM: Staphylotrichum coccosporum

<400> SEQUENCE: 6

```
Met Arg Ser Ser Pro Val Leu Arg Thr Ala Leu Ala Ala Ala Leu Pro
1               5                   10                  15

Leu Ala Ala Leu Ala Ala Asp Gly Lys Ser Thr Arg Tyr Trp Asp Cys
            20                  25                  30

Cys Lys Pro Ser Cys Ser Trp Pro Gly Lys Ala Ser Val Asn Gln Pro
        35                  40                  45

Val Phe Ala Cys Ser Ala Asn Phe Gln Arg Ile Ser Asp Pro Asn Val
    50                  55                  60

Lys Ser Gly Cys Asp Gly Gly Ser Ala Tyr Ala Cys Ala Asp Gln Thr
65                  70                  75                  80

Pro Trp Ala Val Asn Asp Asn Phe Ser Tyr Gly Phe Ala Ala Thr Ser
                85                  90                  95

Ile Ser Gly Gly Asn Glu Ala Ser Trp Cys Cys Gly Cys Tyr Glu Leu
            100                 105                 110

Thr Phe Thr Ser Gly Pro Val Ala Gly Lys Thr Met Val Val Gln Ser
        115                 120                 125

Thr Ser Thr Gly Gly Asp Leu Gly Thr Asn His Phe Asp Leu Ala Met
    130                 135                 140

Pro Gly Gly Gly Val Gly Ile Phe Asp Gly Cys Ser Pro Gln Phe Gly
145                 150                 155                 160

Gly Leu Ala Gly Asp Arg Tyr Gly Gly Val Ser Ser Arg Ser Gln Cys
                165                 170                 175

Asp Ser Phe Pro Ala Ala Leu Lys Pro Gly Cys Tyr Trp Arg Phe Asp
            180                 185                 190

Trp Phe Lys Asn Ala Asp Asn Pro Thr Phe Thr Phe Arg Gln Val Gln
        195                 200                 205

Cys Pro Ser Glu Leu Val Ala Arg Thr Gly Cys Arg Arg Asn Asp Asp
    210                 215                 220

Gly Asn Phe Pro Val Phe Thr Pro Pro Ser Gly Gly Gln Ser Ser Ser
225                 230                 235                 240

Ser Ser Ser Ser Ser Ala Lys Pro Thr Ser Thr Ser Thr Ser Thr
                245                 250                 255

Thr Ser Thr Lys Ala Thr Ser Thr Ser Thr Ala Ser Ser Gln Thr
            260                 265                 270

Ser Ser Ser Thr Gly Gly Gly Cys Ala Ala Gln Arg Trp Ala Gln Cys
        275                 280                 285

Gly Gly Ile Gly Phe Ser Gly Cys Thr Thr Cys Val Ser Gly Thr Thr
```

```
                290                 295                 300
Cys Asn Lys Gln Asn Asp Trp Tyr Ser Gln Cys Leu
305                 310                 315

<210> SEQ ID NO 7
<211> LENGTH: 283
<212> TYPE: PRT
<213> ORGANISM: artificial sequence
<220> FEATURE:
<223> OTHER INFORMATION: variant of STCE1

<400> SEQUENCE: 7

Ala Asp Gly Val Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Thr Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Met Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Lys Met Val Val Gln Ser Thr Ser Thr Gly Gly
            100                 105                 110

Asp Leu Gly Thr Asn His Phe Asp Leu Ala Met Pro Gly Gly Gly Val
        115                 120                 125

Gly Ile Phe Asp Gly Cys Ser Pro Gln Phe Gly Gly Leu Ala Gly Asp
    130                 135                 140

Arg Tyr Gly Gly Val Ser Ser Arg Ser Glu Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp His Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Lys Ala Lys Pro Thr Ser Thr Thr Ser Thr Ala Ser Ser Gln Thr Ser
225                 230                 235                 240

Ser Ser Thr Gly Gly Gly Cys Ala Ala Gln Arg Trp Ala Gln Cys Gly
                245                 250                 255

Gly Ile Gly Phe Ser Gly Cys Thr Thr Cys Val Ser Gly Thr Thr Cys
            260                 265                 270

Asn Lys Gln Asn Asp Trp Tyr Ser Gln Cys Leu
        275                 280

<210> SEQ ID NO 8
<211> LENGTH: 283
<212> TYPE: PRT
<213> ORGANISM: artificial sequence
<220> FEATURE:
<223> OTHER INFORMATION: variant of STCE1

<400> SEQUENCE: 8
```

Ala Asp Gly Val Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Val Ser Gly Cys Asp
                35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Lys Gly Gly Asn
65                  70                  75                  80

Glu Ala Ser Trp Cys Cys Gly Cys Tyr Ala Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
            115                 120                 125

Gly Ile Phe Asp Gly Cys Thr Pro Gln Phe Gly Gly Leu Pro Gly Asp
        130                 135                 140

Arg Tyr Gly Gly Val Ser Ser Arg Ser Glu Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Val
            180                 185                 190

Val Ala Arg Thr Gly Cys Arg Arg Asn Asp Asp Gly Asn Phe Pro His
            195                 200                 205

Phe Thr Pro Pro Ser Gly Gly Gln Ser Ser Ser Leu Ser Ser Ser
    210                 215                 220

Ser Ala Lys Pro Thr Ser Thr Thr Ser Thr Thr Ser Ser Gln Thr Ser
225                 230                 235                 240

Ser Ser Thr Gly Gly Cys Ala Ala Gln Arg Trp Ala Gln Cys Gly
                245                 250                 255

Gly Ile Gly Phe Ser Gly Cys Thr Thr Cys Val Ser Gly Thr Thr Cys
        260                 265                 270

Asn Lys Gln Asn Asp Trp Tyr Ser Gln Cys Leu
            275                 280

<210> SEQ ID NO 9
<211> LENGTH: 284
<212> TYPE: PRT
<213> ORGANISM: artificial sequence
<220> FEATURE:
<223> OTHER INFORMATION: variant of STCE1

<400> SEQUENCE: 9

Ala Asp Gly Val Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
                35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Ser
65                  70                  75                  80

```
Glu Ala Ser Trp Cys Cys Ala Cys Tyr Glu Leu Thr Phe Thr Ser Gly
             85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Ala Gly Asp
        130                 135                 140

Arg Tyr Gly Gly Val Ser Ser Arg Ser Glu Cys Asp Ser Phe Pro Ala
145                 150                 155                 160

Pro Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Ser Asn Phe Pro Val
        195                 200                 205

Phe Thr Pro Pro Ser Gly Gly Gln Ser Ser Ser Leu Ser Ser Ser
    210                 215                 220

Ser Ala Lys Pro Thr Ser Thr Ser Thr Ser Thr Ala Ser Ser Gln Thr
225                 230                 235                 240

Ser Ser Ser Thr Gly Gly Gly Cys Ala Ala Gln Arg Trp Ala Gln Cys
                245                 250                 255

Gly Gly Ile Gly Phe Ser Gly Cys Thr Thr Cys Val Ser Gly Thr Thr
            260                 265                 270

Cys Asn Lys Gln Asn Asp Trp Tyr Ser Gln Cys Leu
            275                 280
```

<210> SEQ ID NO 10
<211> LENGTH: 284
<212> TYPE: PRT
<213> ORGANISM: artificial sequence
<220> FEATURE:
<223> OTHER INFORMATION: variant of STCE1

<400> SEQUENCE: 10

```
Ala Asp Gly Lys Ser Thr Arg Tyr Trp Asp Cys Cys Lys Pro Ser Cys
1               5                  10                  15

Ser Trp Pro Gly Lys Ala Ser Val Asn Gln Pro Val Phe Ala Cys Tyr
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
             85                  90                  95

Pro Val Ala Gly Lys Lys Met Val Val Gln Ser Thr Ser Thr Gly Gly
            100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Pro Gly Asp
        130                 135                 140

Arg Tyr Gly Gly Val Ser Ser Arg Ser Gln Cys Asp Ser Phe Pro Ala
145                 150                 155                 160
```

```
Ala Leu Lys Pro Gly Cys Tyr Trp Arg Phe Asp Trp Phe Lys Asn Ala
            165                 170                 175

Asp Asn Pro Thr Phe Thr Phe Arg Gln Val Gln Cys Pro Ser Glu Leu
        180                 185                 190

Val Ala Arg Thr Gly Cys Arg Arg Asn Asp Asp Ser Asn Phe Pro His
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Ser Thr Ser Ser Gln Thr
225                 230                 235                 240

Ser Ser Ser Thr Gly Gly Gly Cys Ala Ala Gln Arg Trp Ala Gln Cys
                245                 250                 255

Gly Gly Ile Gly Phe Ser Gly Cys Thr Thr Cys Val Ser Gly Thr Thr
            260                 265                 270

Cys Asn Lys Gln Asn Asp Trp Tyr Ser Gln Cys Leu
            275                 280
```

<210> SEQ ID NO 11
<211> LENGTH: 284
<212> TYPE: PRT
<213> ORGANISM: artificial sequence
<220> FEATURE:
<223> OTHER INFORMATION: variant of STCE1

<400> SEQUENCE: 11

```
Ala Asp Gly Val Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Val Ser Gly Cys Asp
            35                  40                  45

Gly Gly Ser Ala Tyr Ala Cys Ala Asp Gln Thr Pro Trp Ala Val Asn
        50                  55                  60

Asp Asn Phe Ser Tyr Gly Phe Ala Ala Thr Ser Ile Lys Gly Gly Ser
65                  70                  75                  80

Glu Ala Ser Trp Cys Cys Gly Cys Tyr Glu Leu Thr Phe Thr Ser Gly
                85                  90                  95

Pro Val Ala Gly Lys Lys Met Val Val Gln Ser Thr Ser Thr Gly Thr
            100                 105                 110

Asp Leu Gly Thr Asn His Phe Asp Leu Ala Met Pro Gly Gly Gly Val
        115                 120                 125

Gly Ile Phe Asp Gly Cys Thr Pro Gln Phe Gly Gly Leu Pro Gly Asp
    130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
            165                 170                 175

Asp Asn Pro Thr Phe Thr Phe Arg Gln Val Gln Cys Pro Ser Glu Val
        180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Ser Thr Ala Ser Ser Gln Thr
225                 230                 235                 240
```

```
Ser Ser Ser Thr Gly Gly Gly Cys Ala Ala Gln Arg Trp Ala Gln Cys
            245                 250                 255

Gly Gly Ile Gly Phe Ser Gly Cys Thr Thr Cys Val Ser Gly Thr Thr
            260                 265                 270

Cys Asn Lys Gln Asn Asp Trp Tyr Ser Gln Cys Leu
            275                 280

<210> SEQ ID NO 12
<211> LENGTH: 284
<212> TYPE: PRT
<213> ORGANISM: artificial sequence
<220> FEATURE:
<223> OTHER INFORMATION: variant of STCE1

<400> SEQUENCE: 12

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
            35                  40                  45

Gly Gly Ser Ala Tyr Ala Cys Ala Asp Gln Thr Pro Trp Ala Val Asn
50                  55                  60

Asp Asn Phe Ser Tyr Gly Phe Ala Ala Thr Ser Ile Met Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Pro Gly Asp
            130                 135                 140

Arg Tyr Gly Gly Val Ser Ser Arg Ser Gln Cys Asp Ser Phe Pro Ala
145                 150                 155                 160

Ala Leu Val Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro His
            195                 200                 205

Phe Thr Pro Pro Ser Gly Gly Gln Ser Ser Ser Ser Ser Ser Ser Ser
210                 215                 220

Ser Ala Lys Pro Thr Ser Thr Ser Ala Ser Thr Thr Ser Ser Gln Thr
225                 230                 235                 240

Ser Ser Ser Thr Gly Gly Gly Cys Ala Ala Gln Arg Trp Ala Gln Cys
            245                 250                 255

Gly Gly Ile Gly Phe Ser Gly Cys Thr Thr Cys Val Ser Gly Thr Thr
            260                 265                 270

Cys Asn Lys Gln Asn Asp Trp Tyr Ser Gln Cys Leu
            275                 280

<210> SEQ ID NO 13
<211> LENGTH: 294
<212> TYPE: PRT
<213> ORGANISM: artificial sequence
<220> FEATURE:
```

<223> OTHER INFORMATION: variant of STCE1

<400> SEQUENCE: 13

```
Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Met Gly Gly Asn
65                  70                  75                  80

Glu Ala Ser Trp Cys Cys Ala Cys Tyr Glu Leu Thr Phe Thr Ser Gly
                85                  90                  95

Pro Val His Gly Lys Thr Met Val Val Gln Ser Thr Ser Thr Gly Thr
            100                 105                 110

Asp Leu Gly Thr Asn His Phe Asp Leu Ala Met Pro Gly Gly Gly Val
        115                 120                 125

Gly Ile Phe Asp Gly Cys Ser Pro Gln Phe Gly Gly Leu Pro Gly Asp
    130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Thr Ser Thr Ala Ser Thr Lys Ala Thr
225                 230                 235                 240

Ser Thr Thr Ser Thr Ala Ser Ser Gln Thr Ser Ser Thr Gly Gly Gly
                245                 250                 255

Gly Cys Ala Ala Gln Arg Trp Ala Gln Cys Gly Gly Ile Gly Phe Ser
            260                 265                 270

Gly Cys Thr Thr Cys Val Ser Gly Thr Thr Cys Asn Lys Gln Asn Asp
        275                 280                 285

Trp Tyr Ser Gln Cys Leu
    290
```

<210> SEQ ID NO 14
<211> LENGTH: 294
<212> TYPE: PRT
<213> ORGANISM: artificial sequence
<220> FEATURE:
<223> OTHER INFORMATION: variant of STCE1

<400> SEQUENCE: 14

```
Ala Asp Gly Lys Ser Thr Arg Tyr Trp Asp Cys Cys Lys Pro Ser Cys
1               5                   10                  15

Ser Trp Pro Gly Lys Ala Leu Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45
```

```
Gly Gly Ser Ala Tyr Ala Cys Ala Asp Gln Thr Pro Trp Ala Val Asn
        50                  55                  60

Asp Asn Phe Ser Tyr Gly Phe Ala Ala Thr Ser Ile Ser Gly Gly Asn
 65                  70                  75                  80

Glu Ala Ser Trp Cys Cys Gly Cys Tyr Glu Leu Thr Phe Thr Ser Gly
                 85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
        115                 120                 125

Gly Ile Phe Asp Gly Cys Ser Pro Gln Phe Gly Gly Leu Pro Gly Asp
    130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Glu Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Thr Ser Thr Thr Ser Thr Lys Ala Thr
225                 230                 235                 240

Ser Thr Thr Ser Thr Ala Ser Ser Gln Thr Ser Ser Thr Gly Gly
                245                 250                 255

Gly Cys Ala Ala Gln Arg Trp Ala Gln Cys Gly Gly Ile Gly Phe Ser
            260                 265                 270

Gly Cys Thr Thr Cys Val Ser Gly Thr Thr Cys Asn Lys Gln Asn Asp
        275                 280                 285

Trp Tyr Ser Gln Cys Leu
    290

<210> SEQ ID NO 15
<211> LENGTH: 295
<212> TYPE: PRT
<213> ORGANISM: artificial sequence
<220> FEATURE:
<223> OTHER INFORMATION: variant of STCE1

<400> SEQUENCE: 15

Ala Asp Gly Lys Ser Thr Arg Tyr Trp Asp Cys Cys Lys Pro Ser Cys
1               5                  10                  15

Ser Trp Pro Gly Lys Ala Ser Val Asn Gln Pro Val Phe Ala Cys Ser
            20                  25                  30

Ala Asn Phe Thr Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
        50                  55                  60

Asp Asn Phe Ser Tyr Gly Phe Ala Ala Thr Ser Ile Lys Gly Gly Asn
 65                  70                  75                  80

Glu Ala Ser Trp Cys Cys Ala Cys Tyr Glu Leu Thr Phe Thr Ser Gly
                 85                  90                  95

Pro Val Ala Gly Lys Thr Met Val Val Gln Ser Thr Ser Thr Gly Gly
            100                 105                 110
```

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Pro Gly Asp
        130                 135                 140

Arg Tyr Gly Gly Val Ser Ser Arg Asp Gln Cys Asp Ser Phe Pro Ala
145                 150                 155                 160

Pro Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Ser Asn Phe Pro Val
        195                 200                 205

Phe Thr Pro Pro Ser Gly Gly Gln Ser Ser Ser Leu Ser Ser Ser
210                 215                 220

Ser Ala Lys Pro Thr Ser Thr Ser Thr Ser Thr Asp Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
                275                 280                 285

Asp Trp Tyr Ser Gln Cys Leu
            290                 295

<210> SEQ ID NO 16
<211> LENGTH: 295
<212> TYPE: PRT
<213> ORGANISM: artificial sequence
<220> FEATURE:
<223> OTHER INFORMATION: variant of STCE1

<400> SEQUENCE: 16

Ala Asp Gly Val Ser Thr Arg Tyr Trp Asp Cys Cys Lys Pro Ser Cys
1                 5                   10                  15

Ser Trp Pro Gly Lys Ala Ser Val Asn Gln Pro Val Trp Ala Cys Ser
                20                  25                  30

Ala Asn Phe Gln Arg Ile Ser Asp Pro Asn Val Lys Ser Gly Cys Asp
            35                  40                  45

Gly Gly Ser Ala Tyr Ala Cys Ala Asp Gln Thr Pro Trp Ala Val Asn
        50                  55                  60

Asp Asn Phe Ser Tyr Gly Phe Ala Ala Thr Ser Ile Lys Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Lys Met Val Val Gln Ser Thr Ser Thr Gly Gly
                100                 105                 110

Asp Leu Gly Thr Asn His Phe Asp Leu Ala Met Pro Gly Gly Gly Val
            115                 120                 125

Gly Ile Phe Asp Gly Cys Ser Glu Gln Phe Gly Gly Leu Ala Gly Asp
        130                 135                 140

Arg Tyr Gly Gly Val Ser Ser Arg Asp Gln Cys Asp Ser Phe Pro Ala
145                 150                 155                 160

Pro Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
                180                 185                 190

Val Ala Arg Thr Gly Cys Arg Arg Asn Asp Asp Gly Asn Phe Pro Val
            195                 200                 205

Phe Val Pro Pro Ser Gly Gly Gln Ser Ser Ser Ser Ser Ser Ser Ser
        210                 215                 220

Ser Ala Lys Pro Thr Ser Thr Ser Thr Ser Thr Ser Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
        290                 295

<210> SEQ ID NO 17
<211> LENGTH: 295
<212> TYPE: PRT
<213> ORGANISM: artificial sequence
<220> FEATURE:
<223> OTHER INFORMATION: variant of STCE1

<400> SEQUENCE: 17

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65              70                  75                  80

Glu Ala Ser Trp Cys Cys Gly Cys Tyr Glu Leu Thr Phe Thr Ser Gly
                85                  90                  95

Pro Val Tyr Gly Lys Thr Met Val Val Gln Ser Thr Ser Thr Gly Thr
            100                 105                 110

Asp Leu Gly Thr Asn His Phe Asp Leu Ala Met Pro Gly Gly Gly Val
        115                 120                 125

Gly Ile Phe Asp Gly Cys Thr Pro Gln Phe Gly Gly Leu Ala Gly Asp
    130                 135                 140

Arg Tyr Gly Gly Val Ser Ser Arg Asp Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Arg Pro Thr Ser Thr Ser Thr Ser Thr Ser Thr Lys Ala
225                 230                 235                 240

```
Thr Ser Thr Thr Ser Thr Ala Ser Ser Gln Thr Ser Ser Thr Gly
            245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
            275                 280                 285

Asp Trp Tyr Ser Gln Cys Leu
            290                 295

<210> SEQ ID NO 18
<211> LENGTH: 295
<212> TYPE: PRT
<213> ORGANISM: artificial sequence
<220> FEATURE:
<223> OTHER INFORMATION: variant of STCE1

<400> SEQUENCE: 18

Ala Asp Gly Lys Ser Thr Arg Tyr Trp Asp Cys Cys Lys Pro Ser Cys
1               5                   10                  15

Ser Trp Pro Gly Lys Ala Leu Val Asn Gln Pro Val Phe Ala Cys Tyr
            20                  25                  30

Ala Asn Phe Gln Arg Ile Ser Asp Pro Asn Val Lys Ser Gly Cys Asp
            35                  40                  45

Gly Gly Ser Ala Tyr Ala Cys Ala Asp Gln Thr Pro Trp Ala Val Asn
        50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
            85                  90                  95

Pro Val Ala Gly Lys Thr Met Val Val Gln Ser Thr Ser Thr Gly Thr
            100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Pro Gly Asp
        130                 135                 140

Arg Tyr Gly Gly Val Ser Ser Arg Ser Gln Cys Asp Ser Phe Pro Ala
145                 150                 155                 160

Pro Leu Lys Pro Gly Cys Tyr Trp Arg Phe Asp Trp Phe Lys Asn Ala
            165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Ser Asn Phe Pro Val
            195                 200                 205

Phe Thr Pro Pro Ser Gly Gly Gln Gly Ser Ser Ser Ser Ser Ser Ser
            210                 215                 220

Ser Ala Arg Pro Thr Ser Thr Ser Thr Thr Thr Asp Thr Lys Ala
225                 230                 235                 240

Thr Ser Thr Thr Ser Thr Ala Ser Ser Gln Thr Ser Ser Thr Gly
            245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
            275                 280                 285

Asp Trp Tyr Ser Gln Cys Leu
            290                 295
```

<210> SEQ ID NO 19
<211> LENGTH: 295
<212> TYPE: PRT
<213> ORGANISM: artificial sequence
<220> FEATURE:
<223> OTHER INFORMATION: variant of STCE1

<400> SEQUENCE: 19

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Trp Ala Cys Ser
            20                  25                  30

Ala Asn Phe Thr Arg Ile Ser Asp Pro Asn Val Val Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Val Asn His Phe Asp Leu Ala Met Pro Gly Gly Gly Val
        115                 120                 125

Gly Ile Phe Asp Gly Cys Thr Pro Gln Phe Gly Gly Leu Ala Gly Asp
    130                 135                 140

Arg Tyr Gly Gly Val Ser Ser Arg Ser Glu Cys Asp Ser Phe Pro Ala
145                 150                 155                 160

Pro Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Gly Ser Ser Ser Leu Ser Ser Ser
    210                 215                 220

Lys Ala Lys Pro Thr Ser Thr Ser Thr Thr Ser Asp Lys Ala
225                 230                 235                 240

Thr Ser Thr Thr Ser Thr Ala Ser Ser Gln Thr Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
    290                 295

<210> SEQ ID NO 20
<211> LENGTH: 295
<212> TYPE: PRT
<213> ORGANISM: artificial sequence
<220> FEATURE:
<223> OTHER INFORMATION: variant of STCE1

<400> SEQUENCE: 20

Ala Asp Gly Val Ser Thr Arg Tyr Trp Asp Cys Cys Lys Pro Ser Cys

```
1               5                   10                  15
Ser Trp Pro Gly Lys Ala Ser Val Asn Gln Pro Val Phe Ala Cys Ser
            20                  25                  30

Ala Asn Phe Thr Arg Ile Ser Asp Pro Asn Val Lys Ser Gly Cys Asp
            35                  40                  45

Gly Gly Ser Ala Tyr Ala Cys Ala Asp Gln Thr Pro Trp Ala Val Asn
            50                  55                  60

Asp Asn Phe Ser Tyr Gly Phe Ala Ala Thr Ser Ile Lys Gly Gly Ser
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
                100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Pro Gly Asp
            130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Val
                180                 185                 190

Val Ala Arg Thr Gly Cys Arg Arg Asn Asp Asp Ser Asn Phe Pro Val
                195                 200                 205

Phe Val Pro Pro Ser Gly Gly Gln Ser Ser Ser Leu Ser Ser Ser
210                 215                 220

Ser Ala Lys Pro Thr Ser Thr Ser Thr Thr Ser Thr Thr Lys Ala
225                 230                 235                 240

Thr Ser Thr Thr Ser Thr Ala Ser Ser Gln Thr Ser Ser Thr Gly
                245                 250                 255

Gly Gly Cys Ala Ala Gln Arg Trp Ala Gln Cys Gly Gly Ile Gly Phe
                260                 265                 270

Ser Gly Cys Thr Thr Cys Val Ser Gly Thr Thr Cys Asn Lys Gln Asn
                275                 280                 285

Asp Trp Tyr Ser Gln Cys Leu
            290                 295

<210> SEQ ID NO 21
<211> LENGTH: 295
<212> TYPE: PRT
<213> ORGANISM: artificial sequence
<220> FEATURE:
<223> OTHER INFORMATION: variant of STCE1

<400> SEQUENCE: 21

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Trp Ala Cys Ser
            20                  25                  30

Ala Asn Phe Gln Arg Ile Ser Asp Pro Asn Val Lys Ser Gly Cys Asp
            35                  40                  45

Gly Gly Ser Ala Tyr Ala Cys Ala Asp Gln Thr Pro Trp Ala Val Asn
            50                  55                  60

Asp Asn Phe Ser Tyr Gly Phe Ala Ala Thr Ser Ile Ser Gly Gly Asn
```

```
                65                  70                  75                  80
Glu Ala Ser Trp Cys Cys Ala Cys Tyr Ala Leu Thr Phe Thr Ser Gly
                    85                  90                  95
Pro Val Tyr Gly Lys Thr Met Val Val Gln Ser Thr Ser Thr Gly Gly
                    100                 105                 110
Asp Leu Gly Thr Asn His Phe Asp Leu Ala Met Pro Gly Gly Gly Val
                    115                 120                 125
Gly Ile Phe Asp Gly Cys Ser Pro Gln Phe Gly Gly Leu Pro Gly Asp
                    130                 135                 140
Arg Tyr Gly Gly Val Ser Ser Arg Asp Gln Cys Asp Ser Phe Pro Ala
145                 150                 155                 160
Ala Leu Lys Pro Gly Cys Tyr Trp Arg Phe Asp Trp Phe Lys Asn Ala
                    165                 170                 175
Asp Asn Pro Thr Phe Thr Phe Arg Gln Val Gln Cys Pro Ser Glu Leu
                    180                 185                 190
Val Ala Arg Thr Gly Cys Arg Arg Asn Asp Asp Gly Asn Phe Pro Val
                    195                 200                 205
Phe Thr Pro Pro Ser Gly Gly Gln Ser Ser Ser Ser Ser Ser Ser Ser
                    210                 215                 220
Ser Ala Arg Pro Thr Ser Thr Ser Thr Ser Thr Asp Thr Lys Ala
225                 230                 235                 240
Thr Ser Thr Thr Ser Thr Ala Ser Ser Gln Thr Ser Ser Thr Gly
                    245                 250                 255
Gly Gly Cys Ala Ala Gln Arg Trp Ala Gln Cys Gly Gly Ile Gly Phe
                    260                 265                 270
Ser Gly Cys Thr Thr Cys Val Ser Gly Thr Thr Cys Asn Lys Gln Asn
                    275                 280                 285
Asp Trp Tyr Ser Gln Cys Leu
                    290                 295

<210> SEQ ID NO 22
<211> LENGTH: 295
<212> TYPE: PRT
<213> ORGANISM: artificial sequence
<220> FEATURE:
<223> OTHER INFORMATION: variant of STCE1

<400> SEQUENCE: 22

Ala Asp Gly Val Ser Thr Arg Tyr Trp Asp Cys Cys Lys Pro Ser Cys
1               5                   10                  15
Ser Trp Pro Gly Lys Ala Ser Val Asn Gln Pro Val Phe Ala Cys Ser
                    20                  25                  30
Ala Asn Phe Gln Arg Ile Ser Asp Pro Asn Val Lys Ser Gly Cys Asp
                    35                  40                  45
Gly Gly Ser Ala Tyr Ala Cys Ala Asp Gln Thr Pro Trp Ala Val Asn
                    50                  55                  60
Asp Asn Phe Ser Tyr Gly Phe Ala Ala Thr Ser Ile Met Gly Gly Asn
65                  70                  75                  80
Glu Ala Ser Trp Cys Cys Gly Cys Tyr Glu Leu Thr Phe Thr Ser Gly
                    85                  90                  95
Pro Val Ala Gly Lys Thr Met Val Val Gln Ser Thr Ser Thr Gly Gly
                    100                 105                 110
Asp Leu Gly Thr Asn His Phe Asp Leu Ala Met Pro Gly Gly Gly Val
                    115                 120                 125
Gly Ile Phe Asp Gly Cys Ser Pro Gln Phe Gly Gly Leu Ala Gly Asp
```

```
            130                 135                 140
Arg Tyr Gly Gly Val Ser Ser Arg Ser Glu Cys Asp Ser Phe Pro Ala
145                 150                 155                 160

Pro Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Val
            180                 185                 190

Val Ala Arg Thr Gly Cys Arg Arg Asn Asp Asp Gly Asn Phe Pro His
        195                 200                 205

Phe Thr Pro Pro Ser Gly Gly Gln Gly Ser Ser Ser Ser Ser Ser Ser
    210                 215                 220

Ser Ala Lys Pro Thr Ser Thr Ser Ala Ser Thr Thr Asp Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
    290                 295

<210> SEQ ID NO 23
<211> LENGTH: 295
<212> TYPE: PRT
<213> ORGANISM: artificial sequence
<220> FEATURE:
<223> OTHER INFORMATION: variant of STCE1

<400> SEQUENCE: 23

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Ala Leu Thr Phe Thr Ser Gly
                85                  90                  95

Pro Val Ala Gly Lys Thr Met Val Val Gln Ser Thr Ser Thr Gly Thr
            100                 105                 110

Asp Leu Gly Thr Asn His Phe Asp Leu Ala Met Pro Gly Gly Gly Val
        115                 120                 125

Gly Ile Phe Asp Gly Cys Thr Pro Gln Phe Gly Gly Leu Ala Gly Asp
    130                 135                 140

Arg Tyr Gly Gly Val Ser Ser Arg Ser Gln Cys Asp Ser Phe Pro Ala
145                 150                 155                 160

Pro Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Ser Asn Phe Pro Val
```

```
                195                 200                 205
Phe Thr Pro Pro Ser Gly Gly Gln Ser Ser Ser Ser Ser Ser Ser
210                 215                 220

Ser Ala Lys Pro Thr Ser Thr Ser Thr Ser Thr Ser Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
            275                 280                 285

Asp Trp Tyr Ser Gln Cys Leu
290                 295

<210> SEQ ID NO 24
<211> LENGTH: 295
<212> TYPE: PRT
<213> ORGANISM: artificial sequence
<220> FEATURE:
<223> OTHER INFORMATION: variant of STCE1

<400> SEQUENCE: 24

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
                20                  25                  30

Ala Asn Phe Gln Arg Ile Ser Asp Pro Asn Val Lys Ser Gly Cys Asp
            35                  40                  45

Gly Gly Thr Ala Tyr Ala Cys Ala Asp Gln Thr Pro Trp Ala Val Asn
50                  55                  60

Asp Asn Phe Ser Tyr Gly Phe Ala Ala Thr Ser Ile Met Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
                100                 105                 110

Asp Leu Gly Thr Asn His Phe Asp Leu Ala Met Pro Gly Gly Gly Val
            115                 120                 125

Gly Ile Phe Asp Gly Cys Ser Glu Gln Phe Gly Gly Leu Ala Gly Asp
            130                 135                 140

Arg Tyr Gly Gly Val Ser Ser Arg Ser Gln Cys Asp Ser Phe Pro Ala
145                 150                 155                 160

Ala Leu Val Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Ser Asn Phe Pro Val
            195                 200                 205

Phe Val Pro Pro Ser Gly Gly Gln Ser Ser Ser Ser Ser Ser Ser
210                 215                 220

Ser Ala Arg Pro Thr Ser Thr Ser Thr Ser Thr Ser Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
```

Ser Gly Cys Thr Thr Cys Val Ser Gly Thr Thr Cys Asn Lys Gln Asn
        275                 280                 285

Asp Trp Tyr Ser Gln Cys Leu
        290                 295

<210> SEQ ID NO 25
<211> LENGTH: 295
<212> TYPE: PRT
<213> ORGANISM: artificial sequence
<220> FEATURE:
<223> OTHER INFORMATION: variant of STCE1

<400> SEQUENCE: 25

Ala Asp Gly Val Ser Thr Arg Tyr Trp Asp Cys Cys Lys Pro Ser Cys
1               5                   10                  15

Ser Trp Pro Gly Lys Ala Ser Val Asn Gln Pro Val Trp Ala Cys Ser
            20                  25                  30

Ala Asn Phe Gln Arg Ile Ser Asp Pro Asn Val Lys Ser Gly Cys Asp
        35                  40                  45

Gly Gly Thr Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Val Asn His Phe Asp Leu Ala Met Pro Gly Gly Gly Val
        115                 120                 125

Gly Ile Phe Asp Gly Cys Thr Pro Gln Phe Gly Gly Leu Ala Gly Asp
    130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Leu Ser Ser Ser
        210                 215                 220

Lys Ala Lys Pro Thr Ser Thr Ser Thr Ser Thr Ser Thr Lys Ala
225                 230                 235                 240

Thr Ser Thr Thr Ser Thr Ala Ser Ser Gln Thr Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
        290                 295

<210> SEQ ID NO 26
<211> LENGTH: 295
<212> TYPE: PRT

<210> SEQ ID NO 26
<211> LENGTH: 295
<212> TYPE: PRT
<213> ORGANISM: artificial sequence
<220> FEATURE:
<223> OTHER INFORMATION: variant of STCE1

<400> SEQUENCE: 26

| | | | | | | | | | | | | | | |
|---|---|---|---|---|---|---|---|---|---|---|---|---|---|---|
| Ala | Asp | Gly | Lys | Ser | Thr | Arg | Tyr | Trp | Asp | Cys | Cys | Lys | Pro | Ser | Cys |
| 1 | | | | 5 | | | | | 10 | | | | | 15 | |
| Ser | Trp | Pro | Gly | Lys | Ala | Ser | Val | Asn | Gln | Pro | Val | Phe | Ala | Cys | Ser |
| | | | 20 | | | | | 25 | | | | | 30 | | |
| Ala | Asn | Phe | Gln | Arg | Ile | Ser | Asp | Pro | Asn | Val | Lys | Ser | Gly | Cys | Asp |
| | | 35 | | | | | 40 | | | | | 45 | | | |
| Gly | Gly | Ser | Ala | Tyr | Ala | Cys | Ala | Asp | Gln | Thr | Pro | Trp | Ala | Val | Asn |
| 50 | | | | | 55 | | | | | 60 | | | | | |
| Asp | Asn | Phe | Ser | Tyr | Gly | Phe | Ala | Ala | Thr | Ser | Ile | Met | Gly | Gly | Asn |
| 65 | | | | | 70 | | | | | 75 | | | | | 80 |
| Glu | Ala | Ser | Trp | Cys | Cys | Gly | Cys | Tyr | Glu | Leu | Thr | Phe | Thr | Ser | Gly |
| | | | | 85 | | | | | 90 | | | | | 95 | |
| Pro | Val | Ala | Gly | Lys | Lys | Met | Val | Val | Gln | Ser | Thr | Ser | Thr | Gly | Gly |
| | | | 100 | | | | | 105 | | | | | 110 | | |
| Asp | Leu | Gly | Val | Asn | His | Phe | Asp | Leu | Ala | Met | Pro | Gly | Gly | Gly | Val |
| | | 115 | | | | | 120 | | | | | 125 | | | |
| Gly | Ile | Phe | Asp | Gly | Cys | Thr | Pro | Gln | Phe | Gly | Gly | Leu | Ala | Gly | Asp |
| 130 | | | | | 135 | | | | | 140 | | | | | |
| Arg | Tyr | Gly | Gly | Val | Ser | Ser | Arg | Asp | Gln | Cys | Asp | Ser | Phe | Pro | Ala |
| 145 | | | | | 150 | | | | | 155 | | | | | 160 |
| Pro | Leu | Lys | Pro | Gly | Cys | Tyr | Trp | Arg | Phe | Asp | Trp | Phe | Lys | Asn | Ala |
| | | | | 165 | | | | | 170 | | | | | 175 | |
| Asp | Asn | Pro | Thr | Phe | Thr | Phe | Arg | Gln | Val | Gln | Cys | Pro | Ser | Glu | Leu |
| | | | 180 | | | | | 185 | | | | | 190 | | |
| Val | Ala | Arg | Thr | Gly | Cys | Arg | Arg | Asn | Asp | Asp | Gly | Asn | Phe | Pro | Val |
| | | 195 | | | | | 200 | | | | | 205 | | | |
| Phe | Thr | Pro | Pro | Ser | Gly | Gly | Gln | Ser | Ser | Ser | Ser | Ser | Ser | Ser | Ser |
| 210 | | | | | 215 | | | | | 220 | | | | | |
| Ser | Ala | Lys | Pro | Thr | Ser | Thr | Ser | Thr | Ser | Thr | Thr | Ser | Asp | Lys | Ala |
| 225 | | | | | 230 | | | | | 235 | | | | | 240 |
| Thr | Ser | Thr | Thr | Ser | Thr | Ala | Ser | Ser | Gln | Thr | Ser | Ser | Ser | Thr | Gly |
| | | | | 245 | | | | | 250 | | | | | 255 | |
| Gly | Gly | Cys | Ala | Ala | Gln | Arg | Trp | Ala | Gln | Cys | Gly | Gly | Ile | Gly | Phe |
| | | | 260 | | | | | 265 | | | | | 270 | | |
| Ser | Gly | Cys | Thr | Thr | Cys | Val | Ser | Gly | Thr | Thr | Cys | Asn | Lys | Gln | Asn |
| | | 275 | | | | | 280 | | | | | 285 | | | |
| Asp | Trp | Tyr | Ser | Gln | Cys | Leu | | | | | | | | | |
| | 290 | | | | | 295 | | | | | | | | | |

<210> SEQ ID NO 27
<211> LENGTH: 295
<212> TYPE: PRT
<213> ORGANISM: artificial sequence
<220> FEATURE:
<223> OTHER INFORMATION: variant of STCE1

<400> SEQUENCE: 27

| | | | | | | | | | | | | | | |
|---|---|---|---|---|---|---|---|---|---|---|---|---|---|---|
| Ala | Asp | Gly | Val | Ser | Thr | Arg | Tyr | Trp | Asp | Cys | Cys | Lys | Pro | Ser | Cys |
| 1 | | | | 5 | | | | | 10 | | | | | 15 | |
| Ser | Trp | Pro | Gly | Lys | Ala | Leu | Val | Asn | Gln | Pro | Val | Phe | Ala | Cys | Tyr |
| | | | 20 | | | | | 25 | | | | | 30 | | |

Ala Asn Phe Gln Arg Ile Ser Asp Pro Asn Val Lys Ser Gly Cys Asp
             35                  40                  45

Gly Gly Ser Ala Tyr Ala Cys Ala Asp Gln Thr Pro Trp Ala Val Asn
 50                  55                  60

Asp Asn Phe Ser Tyr Gly Phe Ala Ala Thr Ser Ile Ser Gly Gly Ser
 65                  70                  75                  80

Glu Ala Ser Trp Cys Cys Gly Cys Tyr Glu Leu Thr Phe Thr Ser Gly
                 85                  90                  95

Pro Val Ala Gly Lys Lys Met Val Gln Ser Thr Ser Thr Gly Gly
             100                 105                 110

Asp Leu Gly Thr Asn His Phe Asp Leu Ala Met Pro Gly Gly Val
         115                 120                 125

Gly Ile Phe Asp Gly Cys Ser Pro Gln Phe Gly Gly Leu Pro Gly Asp
 130                 135                 140

Arg Tyr Gly Gly Val Ser Ser Arg Ser Gln Cys Asp Ser Phe Pro Ala
145                 150                 155                 160

Pro Leu Lys Pro Gly Cys Tyr Trp Arg Phe Asp Trp Phe Lys Asn Ala
                 165                 170                 175

Asp Asn Pro Thr Phe Thr Phe Arg Gln Val Gln Cys Pro Ser Glu Leu
             180                 185                 190

Val Ala Arg Thr Gly Cys Arg Arg Asn Asp Asp Gly Asn Phe Pro Val
             195                 200                 205

Phe Thr Pro Pro Ser Gly Gly Gln Ser Ser Ser Ser Ser Ser Ser Ser
             210                 215                 220

Ser Ala Lys Pro Thr Ser Thr Ser Thr Ser Thr Thr Asp Thr Lys Ala
225                 230                 235                 240

Thr Ser Thr Thr Ser Thr Ala Ser Ser Gln Thr Ser Ser Ser Thr Gly
                 245                 250                 255

Gly Gly Cys Ala Ala Gln Arg Trp Ala Gln Cys Gly Gly Ile Gly Phe
             260                 265                 270

Ser Gly Cys Thr Thr Cys Val Ser Gly Thr Thr Cys Asn Lys Gln Asn
             275                 280                 285

Asp Trp Tyr Ser Gln Cys Leu
             290                 295

<210> SEQ ID NO 28
<211> LENGTH: 295
<212> TYPE: PRT
<213> ORGANISM: artificial sequence
<220> FEATURE:
<223> OTHER INFORMATION: variant of STCE1

<400> SEQUENCE: 28

Ala Asp Gly Lys Ser Thr Arg Tyr Trp Asp Cys Cys Lys Pro Ser Cys
 1               5                  10                  15

Ser Trp Pro Gly Lys Ala Ser Val Asn Gln Pro Val Phe Ala Cys Ser
                 20                  25                  30

Ala Asn Phe Gln Arg Ile Ser Asp Pro Asn Val Val Ser Gly Cys Asp
             35                  40                  45

Gly Gly Ser Ala Tyr Ala Cys Ala Asp Gln Thr Pro Trp Ala Val Asn
 50                  55                  60

Asp Asn Phe Ser Tyr Gly Phe Ala Ala Thr Ser Ile Ser Gly Gly Asn
 65                  70                  75                  80

Glu Ala Ser Trp Cys Cys Ala Cys Tyr Glu Leu Thr Phe Thr Ser Gly
                 85                  90                  95

```
Pro Val Ala Gly Lys Thr Met Val Val Gln Ser Thr Ser Thr Gly Gly
                100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Ala Gly Asp
        130                 135                 140

Arg Tyr Gly Gly Val Ser Ser Arg Ser Glu Cys Asp Ser Phe Pro Ala
145                 150                 155                 160

Pro Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
210                 215                 220

Ser Ala Lys Pro Thr Ser Thr Ser Thr Thr Ser Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
    290                 295

<210> SEQ ID NO 29
<211> LENGTH: 295
<212> TYPE: PRT
<213> ORGANISM: artificial sequence
<220> FEATURE:
<223> OTHER INFORMATION: variant of STCE1

<400> SEQUENCE: 29

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Tyr
                20                  25                  30

Ala Asn Phe Gln Arg Ile Ser Asp Pro Asn Val Lys Ser Gly Cys Asp
            35                  40                  45

Gly Gly Ser Ala Tyr Ala Cys Ala Asp Gln Thr Pro Trp Ala Val Asn
        50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
                100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Pro Gly Asp
        130                 135                 140

Arg Tyr Gly Gly Val Ser Ser Arg Ser Glu Cys Asp Ser Phe Pro Ala
145                 150                 155                 160
```

```
Ala Leu Val Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Gly Ser Ser Ser Ser Ser Ser Ser
    210                 215                 220

Ser Ala Arg Pro Thr Ser Thr Ser Ala Ser Thr Ser Thr Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
    290                 295

<210> SEQ ID NO 30
<211> LENGTH: 295
<212> TYPE: PRT
<213> ORGANISM: artificial sequence
<220> FEATURE:
<223> OTHER INFORMATION: variant of STCE1

<400> SEQUENCE: 30

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asp Phe Gln Arg Ile Ser Asp Pro Asn Val Lys Ser Gly Cys Asp
        35                  40                  45

Gly Gly Thr Ala Tyr Ala Cys Ala Asp Gln Thr Pro Trp Ala Val Asn
50                  55                  60

Asp Asn Phe Ser Tyr Gly Phe Ala Ala Thr Ser Ile Ser Gly Gly Asn
65                  70                  75                  80

Glu Ala Ser Trp Cys Cys Ala Cys Tyr Glu Leu Thr Phe Thr Ser Gly
                85                  90                  95

Pro Val Ala Gly Lys Lys Met Val Val Gln Ser Thr Ser Thr Gly Gly
            100                 105                 110

Asp Leu Gly Val Asn His Phe Asp Leu Ala Met Pro Gly Gly Gly Val
        115                 120                 125

Gly Ile Phe Asp Gly Cys Ser Glu Gln Phe Gly Gly Leu Ala Gly Asp
    130                 135                 140

Arg Tyr Gly Gly Val Ser Ser Arg Ser Glu Cys Asp Ser Phe Pro Ala
145                 150                 155                 160

Pro Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Val
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220
```

```
Ser Ala Lys Pro Thr Ser Thr Ser Ala Ser Thr Ser Asp Lys Ala
225                 230                 235                 240

Thr Ser Thr Thr Ser Thr Ala Ser Ser Gln Thr Ser Ser Thr Gly
            245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
            275                 280                 285

Asp Trp Tyr Ser Gln Cys Leu
    290                 295

<210> SEQ ID NO 31
<211> LENGTH: 294
<212> TYPE: PRT
<213> ORGANISM: artificial sequence
<220> FEATURE:
<223> OTHER INFORMATION: variant of STCE1

<400> SEQUENCE: 31

Ala Asp Gly Val Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
            35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Lys Gly Gly Asn
65                  70                  75                  80

Glu Ala Ser Trp Cys Cys Gly Cys Tyr Ala Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Pro Gly Asp
    130                 135                 140

Arg Tyr Gly Gly Val Ser Ser Arg Ser Gln Cys Asp Asp Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
            195                 200                 205

Phe Thr Pro Pro Ser Gly Gln Gly Ser Ser Ser Ser Ser Ser Ser Ser
210                 215                 220

Ala Lys Pro Thr Ser Thr Ser Ala Ser Thr Ser Ser Asp Lys Ala Thr
225                 230                 235                 240

Ser Thr Thr Ser Thr Ala Ser Ser Gln Thr Ser Ser Thr Gly Gly
                245                 250                 255

Gly Cys Ala Ala Gln Arg Trp Ala Gln Cys Gly Gly Ile Gly Phe Ser
            260                 265                 270

Gly Cys Thr Thr Cys Val Ser Gly Thr Thr Cys Asn Lys Gln Asn Asp
            275                 280                 285
```

Trp Tyr Ser Gln Cys Leu
    290

<210> SEQ ID NO 32
<211> LENGTH: 295
<212> TYPE: PRT
<213> ORGANISM: artificial sequence
<220> FEATURE:
<223> OTHER INFORMATION: variant of STCE1

<400> SEQUENCE: 32

Ala Asp Gly Val Ser Thr Arg Tyr Trp Asp Cys Cys Lys Pro Ser Cys
1               5                  10                  15

Ser Trp Pro Gly Lys Ala Ser Val Asn Gln Pro Val Phe Ala Cys Ser
            20                  25                  30

Ala Asn Phe Thr Arg Ile Ser Asp Pro Asn Val Lys Ser Gly Cys Asp
        35                  40                  45

Gly Gly Thr Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Ser
65              70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
        115                 120                 125

Gly Ile Phe Asp Gly Cys Thr Pro Gln Phe Gly Gly Leu Ala Gly Asp
    130                 135                 140

Arg Tyr Gly Gly Val Ser Ser Arg Ser Gln Cys Asp Asp Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Ala Ser Thr Thr Ser Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
    290                 295

<210> SEQ ID NO 33
<211> LENGTH: 294
<212> TYPE: PRT
<213> ORGANISM: artificial sequence
<220> FEATURE:
<223> OTHER INFORMATION: variant of STCE1

<400> SEQUENCE: 33

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Thr Arg Ile Ser Asp Pro Asn Val Lys Ser Gly Cys Asp
                35                  40                  45

Gly Gly Ser Ala Tyr Ala Cys Ala Asp Gln Thr Pro Trp Ala Val Asn
50                  55                  60

Asp Asn Phe Ser Tyr Gly Phe Ala Ala Thr Ser Ile Lys Gly Gly Asn
65                  70                  75                  80

Glu Ala Ser Trp Cys Cys Ala Cys Tyr Glu Leu Thr Phe Thr Ser Gly
                85                  90                  95

Pro Val Ala Gly Lys Thr Met Val Val Gln Ser Thr Ser Thr Gly Gly
                100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Pro Gly Asp
        130                 135                 140

Arg Tyr Gly Gly Val Ser Ser Arg Asp Gln Cys Asp Ser Phe Pro Ala
145                 150                 155                 160

Pro Leu Lys Pro Gly Cys Tyr Trp Arg Phe Asp Trp Phe Lys Asn Ala
                165                 170                 175

Asn Pro Thr Phe Thr Phe Arg Gln Val Gln Cys Pro Ser Glu Leu Val
                180                 185                 190

Ala Arg Thr Gly Cys Arg Arg Asn Asp Ser Asn Phe Pro Val Phe
                195                 200                 205

Thr Pro Pro Ser Gly Gly Gln Ser Ser Ser Leu Ser Ser Ser Ser
210                 215                 220

Ala Lys Pro Thr Ser Thr Ser Thr Thr Asp Thr Lys Ala Thr
225                 230                 235                 240

Ser Thr Thr Ser Thr Ala Ser Ser Gln Thr Ser Ser Thr Gly Gly
                245                 250                 255

Gly Cys Ala Ala Gln Arg Trp Ala Gln Cys Gly Gly Ile Gly Phe Ser
                260                 265                 270

Gly Cys Thr Thr Cys Val Ser Gly Thr Thr Cys Asn Lys Gln Asn Asp
            275                 280                 285

Trp Tyr Ser Gln Cys Leu
        290

<210> SEQ ID NO 34
<211> LENGTH: 294
<212> TYPE: PRT
<213> ORGANISM: artificial sequence
<220> FEATURE:
<223> OTHER INFORMATION: variant of STCE1

<400> SEQUENCE: 34

Ala Asp Gly Val Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
                35                  40                  45

Gly Gly Thr Ala Tyr Ala Cys Ala Asp Gln Thr Pro Trp Ala Val Asn
50                  55                  60

```
Asp Asn Phe Ser Tyr Gly Phe Ala Ala Thr Ser Ile Ser Gly Gly Asn
 65                  70                  75                  80

Glu Ala Ser Trp Cys Cys Gly Cys Tyr Glu Leu Thr Phe Thr Ser Gly
                 85                  90                  95

Pro Gly Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
            115                 120                 125

Gly Ile Phe Asp Gly Cys Thr Pro Gln Phe Gly Leu Ala Gly Asp
130                 135                 140

Arg Tyr Gly Gly Val Ser Ser Arg Ser Glu Cys Asp Ser Phe Pro Ala
145                 150                 155                 160

Ala Leu Lys Pro Gly Cys Tyr Trp Arg Phe Trp Phe Lys Asn Ala Asp
                165                 170                 175

Asn Pro Thr Phe Thr Phe Arg Gln Val Gln Cys Pro Ser Glu Leu Val
            180                 185                 190

Ala Arg Thr Gly Cys Arg Arg Asn Asp Asp Gly Asn Phe Pro Val Phe
            195                 200                 205

Thr Pro Pro Ser Gly Gly Gln Ser Ser Ser Ser Ser Ser Ser Ser Ser
210                 215                 220

Ala Lys Pro Thr Ser Thr Ser Ala Ser Thr Thr Ser Thr Lys Ala Thr
225                 230                 235                 240

Ser Thr Thr Ser Thr Ala Ser Ser Gln Thr Ser Ser Thr Gly Gly
                    245                 250                 255

Gly Cys Ala Ala Gln Arg Trp Ala Gln Cys Gly Gly Ile Gly Phe Ser
            260                 265                 270

Gly Cys Thr Thr Cys Val Ser Gly Thr Thr Cys Asn Lys Gln Asn Asp
            275                 280                 285

Trp Tyr Ser Gln Cys Leu
            290

<210> SEQ ID NO 35
<211> LENGTH: 295
<212> TYPE: PRT
<213> ORGANISM: artificial sequence
<220> FEATURE:
<223> OTHER INFORMATION: variant of STCE1

<400> SEQUENCE: 35

Ala Asp Gly Lys Ser Thr Arg Tyr Trp Asp Cys Cys Lys Pro Ser Cys
 1               5                  10                  15

Ser Trp Pro Gly Lys Ala Ser Val Asn Gln Pro Val Phe Ala Cys Ser
                20                  25                  30

Ala Asn Phe Gln Arg Ile Ser Asp Pro Asn Val Lys Ser Gly Cys Asp
                 35                  40                  45

Gly Gly Ser Ala Tyr Ala Cys Ala Asp Gln Thr Pro Trp Ala Val Asn
             50                  55                  60

Asp Asn Phe Ser Tyr Gly Phe Ala Ala Thr Ser Ile Ser Gly Gly Asn
 65                  70                  75                  80

Glu Ala Ser Trp Cys Cys Gly Cys Tyr Glu Leu Thr Phe Thr Ser Gly
                 85                  90                  95

Pro Val Ala Gly Lys Lys Met Val Val Gln Ser Thr Ser Thr Gly Gly
            100                 105                 110

Asp Leu Gly Thr Asn His Phe Asp Leu Ala Met Pro Gly Gly Gly Val
            115                 120                 125
```

```
Gly Ile Phe Asp Gly Cys Ser Pro Gln Phe Gly Gly Leu Pro Gly Asp
            130                 135                 140

Arg Tyr Gly Gly Val Ser Ser Arg Ser Glu Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Ser Asn Phe Pro Val
        195                 200                 205

Phe Thr Pro Pro Ser Gly Gly Gln Ser Ser Ser Ser Ser Ser Ser Ser
        210                 215                 220

Ser Ala Arg Pro Thr Ser Thr Ser Thr Ser Thr Ser Thr Ser Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
            275                 280                 285

Asp Trp Tyr Ser Gln Cys Leu
            290                 295

<210> SEQ ID NO 36
<211> LENGTH: 295
<212> TYPE: PRT
<213> ORGANISM: artificial sequence
<220> FEATURE:
<223> OTHER INFORMATION: variant of STCE1

<400> SEQUENCE: 36

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45

Gly Gly Thr Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65              70                  75                  80

Glu Ala Ser Trp Cys Cys Ala Cys Tyr Glu Leu Thr Phe Thr Ser Gly
                85                  90                  95

Pro Val Tyr Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
            115                 120                 125

Gly Ile Phe Asp Gly Cys Thr Pro Gln Phe Gly Gly Leu Ala Gly Asp
            130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190
```

Val Ala Arg Thr Gly Cys Arg Arg Asn Asp Asp Gly Asp Phe Pro Val
            195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Ser Thr Ser Thr Ser Asp Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
                260                 265                 270

Ser Gly Cys Thr Thr Cys Val Ser Gly Thr Thr Cys Asn Lys Gln Asn
            275                 280                 285

Asp Trp Tyr Ser Gln Cys Leu
            290                 295

<210> SEQ ID NO 37
<211> LENGTH: 295
<212> TYPE: PRT
<213> ORGANISM: artificial sequence
<220> FEATURE:
<223> OTHER INFORMATION: variant of STCE1

<400> SEQUENCE: 37

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
                20                  25                  30

Ala Asn Phe Gln Arg Ile Ser Asp Pro Asn Val Lys Ser Gly Cys Asp
            35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65                  70                  75                  80

Glu Ala Ser Trp Cys Cys Ala Cys Tyr Glu Leu Thr Phe Thr Ser Gly
                85                  90                  95

Pro Val Ala Gly Lys Thr Met Val Val Gln Ser Thr Ser Thr Gly Gly
                100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Pro Gly Asp
    130                 135                 140

Arg Tyr Gly Gly Val Ser Ser Arg Ser Gln Cys Asp Ser Phe Pro Ala
145                 150                 155                 160

Pro Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Val
            180                 185                 190

Val Ala Arg Thr Gly Cys Arg Arg Asn Asp Asp Ser Asn Phe Pro Val
            195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Ser Thr Ser Thr Ser Thr Lys Ala
225                 230                 235                 240

Ala Ser Thr Thr Ser Thr Ala Ser Ser Gln Thr Ser Ser Ser Thr Gly
                245                 250                 255

```
Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
            275                 280                 285

Asp Trp Tyr Ser Gln Cys Leu
            290             295

<210> SEQ ID NO 38
<211> LENGTH: 295
<212> TYPE: PRT
<213> ORGANISM: artificial sequence
<220> FEATURE:
<223> OTHER INFORMATION: variant of STCE1

<400> SEQUENCE: 38

Ala Asp Gly Val Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Lys Gly Gly Asn
65                  70                  75                  80

Glu Ala Ser Trp Cys Cys Gly Cys Tyr Ala Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Pro Gly Asp
        130                 135                 140

Arg Tyr Gly Gly Val Ser Ser Arg Ser Gln Cys Asp Asp Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Gly Ser Ser Ser Ser Ser Ser Ser
    210                 215                 220

Ser Ala Lys Pro Thr Thr Ser Ala Ser Thr Thr Ser Asp Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
            275                 280                 285

Asp Trp Tyr Ser Gln Cys Leu
            290             295

<210> SEQ ID NO 39
```

<211> LENGTH: 295
<212> TYPE: PRT
<213> ORGANISM: artificial sequence
<220> FEATURE:
<223> OTHER INFORMATION: variant of STCE1

<400> SEQUENCE: 39

```
Ala Asp Gly Val Ser Thr Arg Tyr Trp Asp Cys Cys Lys Pro Ser Cys
1               5                   10                  15
Ser Trp Pro Gly Lys Ala Ser Val Asn Gln Pro Val Phe Ala Cys Ser
            20                  25                  30
Ala Asn Phe Gln Arg Ile Ser Asp Pro Asn Val Lys Ser Gly Cys Asp
        35                  40                  45
Gly Gly Ser Ala Tyr Ala Cys Ala Asp Gln Thr Pro Trp Ala Val Asn
    50                  55                  60
Asp Asn Phe Ser Tyr Gly Phe Ala Ala Thr Ser Ile Ser Gly Gly Asn
65                  70                  75                  80
Glu Ala Ser Trp Cys Cys Gly Cys Tyr Glu Leu Thr Phe Thr Ser Gly
                85                  90                  95
Pro Val Ala Gly Lys Thr Met Val Val Gln Ser Thr Ser Thr Gly Gly
            100                 105                 110
Asp Leu Gly Thr Asn His Phe Asp Leu Ala Met Pro Gly Gly Gly Val
        115                 120                 125
Gly Ile Phe Asp Gly Cys Ser Glu Gln Phe Gly Gly Leu Ala Gly Asp
    130                 135                 140
Arg Tyr Gly Gly Val Ser Ser Arg Asp Gln Cys Asp Ser Phe Pro Ala
145                 150                 155                 160
Pro Leu Lys Pro Gly Cys Tyr Trp Arg Phe Asp Trp Phe Lys Asn Ala
                165                 170                 175
Asp Asn Pro Thr Phe Thr Phe Arg Gln Val Gln Cys Pro Ser Glu Leu
            180                 185                 190
Val Ala Arg Thr Gly Cys Arg Arg Asn Asp Asp Gly Asn Phe Pro Val
        195                 200                 205
Phe Val Pro Pro Ser Gly Gly Gln Ser Ser Ser Ser Ser Ser Ser Ser
    210                 215                 220
Ser Ala Arg Pro Thr Ser Thr Ser Thr Ser Thr Ser Thr Ser Lys Ala
225                 230                 235                 240
Thr Ser Thr Thr Ser Thr Ala Ser Ser Gln Thr Ser Ser Ser Thr Gly
                245                 250                 255
Gly Gly Cys Ala Ala Gln Arg Trp Ala Gln Cys Gly Gly Ile Gly Phe
            260                 265                 270
Ser Gly Cys Thr Thr Cys Val Ser Gly Thr Thr Cys Asn Lys Gln Asn
        275                 280                 285
Asp Trp Tyr Ser Gln Cys Leu
    290                 295
```

<210> SEQ ID NO 40
<211> LENGTH: 293
<212> TYPE: PRT
<213> ORGANISM: artificial sequence
<220> FEATURE:
<223> OTHER INFORMATION: variant of STCE1

<400> SEQUENCE: 40

```
Ala Asp Gly Lys Ser Thr Arg Tyr Trp Asp Cys Cys Lys Pro Ser Cys
1               5                   10                  15
Ser Trp Pro Gly Lys Ala Ser Val Asn Gln Pro Val Phe Ala Cys Ser
```

```
            20                  25                  30
Ala Asn Phe Gln Arg Ile Ser Asp Pro Asn Val Lys Ser Gly Cys Asp
            35                  40                  45

Gly Gly Thr Ala Tyr Ala Cys Ala Asp Gln Thr Pro Trp Ala Val Asn
        50                  55                  60

Asp Asn Phe Ser Tyr Gly Phe Ala Ala Thr Ser Ile Ser Gly Gly Ser
 65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Pro Gly Asp
            130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Trp Phe Lys Asn Ala Asn
                165                 170                 175

Pro Thr Phe Thr Phe Arg Gln Val Gln Cys Pro Ser Glu Val Val Ala
            180                 185                 190

Arg Thr Gly Cys Arg Arg Asn Asp Asp Gly Asn Phe Pro His Phe Thr
            195                 200                 205

Pro Pro Ser Gly Gly Gln Ser Ser Ser Ser Ser Ser Ser Ser Ser Ala
            210                 215                 220

Lys Pro Thr Ser Thr Ser Thr Ser Thr Ser Thr Lys Ala Thr Ser
225                 230                 235                 240

Thr Thr Ser Thr Ala Ser Ser Gln Thr Ser Ser Thr Gly Gly Gly
                245                 250                 255

Cys Ala Ala Gln Arg Trp Ala Gln Cys Gly Gly Ile Gly Phe Ser Gly
            260                 265                 270

Cys Thr Thr Cys Val Ser Gly Thr Thr Cys Asn Lys Gln Asn Asp Trp
            275                 280                 285

Tyr Ser Gln Cys Leu
            290

<210> SEQ ID NO 41
<211> LENGTH: 295
<212> TYPE: PRT
<213> ORGANISM: artificial sequence
<220> FEATURE:
<223> OTHER INFORMATION: variant of STCE1

<400> SEQUENCE: 41

Ala Asp Gly Val Ser Thr Arg Tyr Trp Asp Cys Cys Lys Pro Ser Cys
 1               5                  10                  15

Ser Trp Pro Gly Lys Ala Leu Val Asn Gln Pro Val Phe Ala Cys Ser
            20                  25                  30

Ala Asn Phe Thr Arg Ile Ser Asp Pro Asn Val Lys Ser Gly Cys Asp
            35                  40                  45

Gly Gly Ser Ala Tyr Ala Cys Ala Asp Gln Thr Pro Trp Ala Val Asn
        50                  55                  60

Asp Asn Phe Ser Tyr Gly Phe Ala Ala Thr Ser Ile Met Gly Gly Asn
 65                  70                  75                  80

Glu Ala Ser Trp Cys Cys Gly Cys Tyr Glu Leu Thr Phe Thr Ser Gly
```

```
                    85                  90                  95
Pro Val Ala Gly Lys Thr Met Val Val Gln Ser Thr Ser Thr Gly Thr
                100                 105                 110

Asp Leu Gly Thr Asn His Phe Asp Leu Ala Met Pro Gly Gly Gly Val
                115                 120                 125

Gly Ile Phe Asp Gly Cys Ser Pro Gln Phe Gly Gly Leu Ala Gly Asp
            130                 135                 140

Arg Tyr Gly Gly Val Ser Ser Arg Ser Gln Cys Asp Asp Phe Pro Ala
145                 150                 155                 160

Pro Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Val
                180                 185                 190

Val Ala Arg Thr Gly Cys Arg Arg Asn Asp Asp Gly Asn Phe Pro Val
                195                 200                 205

Phe Thr Pro Pro Ser Gly Gly Gln Ser Ser Ser Leu Ser Ser Ser
            210                 215                 220

Ser Ala Lys Pro Thr Ser Thr Ser Thr Ser Thr Ser Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
                260                 265                 270

Ser Gly Cys Thr Thr Cys Val Ser Gly Thr Thr Cys Asn Lys Gln Asn
                275                 280                 285

Asp Trp Tyr Ser Gln Cys Leu
                290                 295

<210> SEQ ID NO 42
<211> LENGTH: 295
<212> TYPE: PRT
<213> ORGANISM: artificial sequence
<220> FEATURE:
<223> OTHER INFORMATION: variant of STCE1

<400> SEQUENCE: 42

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
                20                  25                  30

Ala Asn Phe Thr Arg Ile Ser Asp Pro Asn Val Lys Ser Gly Cys Asp
            35                  40                  45

Gly Gly Ser Ala Tyr Ala Cys Ala Asp Gln Thr Pro Trp Ala Val Asn
        50                  55                  60

Asp Asn Phe Ser Tyr Gly Phe Ala Ala Thr Ser Ile Ser Gly Gly Asn
65              70                  75                  80

Glu Ala Ser Trp Cys Cys Gly Cys Tyr Glu Leu Thr Phe Thr Ser Gly
                85                  90                  95

Pro Tyr Ala Gly Lys Thr Met Val Val Gln Ser Thr Ser Thr Gly Gly
                100                 105                 110

Asp Leu Gly Thr Asn His Phe Asp Leu Ala Met Pro Gly Gly Gly Val
                115                 120                 125

Gly Ile Phe Asp Gly Cys Ser Pro Gln Phe Gly Gly Leu Pro Gly Asp
            130                 135                 140

Arg Tyr Gly Gly Val Ser Ser Arg Ser Gln Cys Asp Ser Phe Pro Ala
```

```
              145                 150                 155                 160
        Glu Leu Lys Pro Gly Cys Tyr Trp Arg Phe Asp Trp Phe Lys Asn Ala
                        165                 170                 175
        Asp Asn Pro Thr Phe Thr Phe Arg Gln Val Gln Cys Pro Ser Glu Leu
                        180                 185                 190
        Val Ala Arg Thr Gly Cys Arg Arg Asn Asp Asp Gly Asn Phe Pro Val
                        195                 200                 205
        Phe Thr Pro Pro Ser Gly Gly Gln Ser Ser Ser Ser Ser Ser Ser Ser
                        210                 215                 220
        Lys Ala Lys Pro Thr Ser Thr Ser Thr Ser Thr Ser Thr Ser Lys Ala
        225                 230                 235                 240
        Thr Ser Thr Thr Ser Thr Ala Ser Ser Gln Thr Ser Ser Ser Thr Gly
                            245                 250                 255
        Gly Gly Cys Ala Ala Gln Arg Trp Ala Gln Cys Gly Gly Ile Gly Phe
                        260                 265                 270
        Ser Gly Cys Thr Thr Cys Val Ser Gly Thr Thr Cys Asn Lys Gln Asn
                        275                 280                 285
        Asp Trp Tyr Ser Gln Cys Leu
                        290                 295

<210> SEQ ID NO 43
<211> LENGTH: 295
<212> TYPE: PRT
<213> ORGANISM: artificial sequence
<220> FEATURE:
<223> OTHER INFORMATION: variant of STCE1

<400> SEQUENCE: 43

Ala Asp Gly Lys Ser Thr Arg Tyr Trp Asp Cys Cys Lys Pro Ser Cys
        1               5                   10                  15
        Ser Trp Pro Gly Lys Ala Ser Val Asn Gln Pro Val Phe Ala Cys Ser
                        20                  25                  30
        Ala Asn Phe Thr Arg Ile Ser Asp Pro Asn Val Lys Ser Gly Cys Asp
                        35                  40                  45
        Gly Gly Ser Ala Tyr Ala Cys Ala Asp Gln Thr Pro Trp Ala Val Asn
                        50                  55                  60
        Asp Asn Phe Ser Tyr Gly Phe Ala Ala Thr Ser Ile Ser Gly Gly Asn
        65                  70                  75                  80
        Glu Ala Ser Trp Cys Cys Gly Cys Tyr Glu Leu Thr Phe Thr Ser Gly
                        85                  90                  95
        Pro Val Ala Gly Lys Thr Met Val Val Gln Ser Thr Ser Thr Gly Gly
                        100                 105                 110
        Asp Leu Gly Thr Asn His Phe Asp Leu Ala Met Pro Gly Gly Gly Val
                        115                 120                 125
        Gly Ile Phe Asp Gly Cys Ser Glu Gln Phe Gly Gly Leu Pro Gly Asp
                        130                 135                 140
        Arg Tyr Gly Gly Val Ser Ser Arg Ser Gln Cys Asp Ser Phe Pro Ala
        145                 150                 155                 160
        Ala Leu Lys Pro Gly Cys Tyr Trp Arg Phe Asp Trp Phe Lys Asn Ala
                        165                 170                 175
        Asp Asn Pro Thr Phe Thr Phe Arg Gln Val Gln Cys Pro Ser Glu Leu
                        180                 185                 190
        Val Ala Arg Thr Gly Cys Arg Arg Asn Asp Asp Gly Asn Phe Pro Val
                        195                 200                 205
        Phe Thr Pro Pro Ser Gly Gly Gln Ser Ser Ser Ser Ser Ser Ser Ser
```

```
            210                 215                 220
Lys Ala Lys Pro Thr Ser Thr Ser Thr Ser Thr Ser Thr Lys Ala
225                 230                 235                 240

Thr Ser Thr Thr Ser Thr Ala Ser Pro Gln Thr Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
            275                 280                 285

Asp Trp Tyr Ser Gln Cys Leu
            290                 295

<210> SEQ ID NO 44
<211> LENGTH: 295
<212> TYPE: PRT
<213> ORGANISM: artificial sequence
<220> FEATURE:
<223> OTHER INFORMATION: variant of STCE1

<400> SEQUENCE: 44

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
                20                  25                  30

Ala Asn Phe Gln Arg Ile Ser Asp Pro Asn Val Lys Ser Gly Cys Asp
            35                  40                  45

Gly Gly Ser Ala Tyr Ala Cys Ala Asp Gln Thr Pro Trp Ala Val Asn
50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Pro Val Tyr Gly Lys Thr Met Val Val Gln Ser Thr Ser Thr Gly Gly
                100                 105                 110

Asp Leu Gly Thr Asn His Phe Asp Leu Ala Met Pro Gly Gly Gly Val
            115                 120                 125

Gly Ile Phe Asp Gly Cys Ser Glu Gln Phe Gly Gly Leu Pro Gly Asp
130                 135                 140

Arg Tyr Gly Gly Val Ser Ser Arg Ser Gln Cys Asp Ser Phe Pro Ala
145                 150                 155                 160

Glu Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
            195                 200                 205

Phe Thr Pro Pro Ser Gly Gly Gln Ser Ser Ser Leu Ser Ser Ser
        210                 215                 220

Ser Ala Lys Pro Thr Ser Thr Ser Thr Ser Thr Ser Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
```

Asp Trp Tyr Ser Gln Cys Leu
    290             295

<210> SEQ ID NO 45
<211> LENGTH: 295
<212> TYPE: PRT
<213> ORGANISM: artificial sequence
<220> FEATURE:
<223> OTHER INFORMATION: variant of STCE1

<400> SEQUENCE: 45

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Asp
            20                  25                  30

Ala Asn Phe Thr Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
        115                 120                 125

Gly Ile Phe Asp Gly Cys Ser Pro Gln Phe Gly Gly Leu Ala Gly Asp
    130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Leu Ser Ser Ser
    210                 215                 220

Lys Ala Lys Pro Thr Ser Thr Ser Thr Thr Ser Thr Lys Ala
225                 230                 235                 240

Thr Ser Thr Thr Ser Thr Ala Ser Ser Gln Thr Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
    290             295

<210> SEQ ID NO 46
<211> LENGTH: 295
<212> TYPE: PRT
<213> ORGANISM: artificial sequence
<220> FEATURE:
<223> OTHER INFORMATION: variant of STCE1

-continued

<400> SEQUENCE: 46

```
Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Asp
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Pro Val Tyr Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
        115                 120                 125

Gly Ile Phe Asp Gly Cys Ser Pro Gln Phe Gly Gly Leu Pro Gly Asp
    130                 135                 140

Arg Tyr Gly Gly Val Ser Ser Arg Ser Gln Cys Asp Ser Phe Pro Ala
145                 150                 155                 160

Glu Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Thr Ser Thr Thr Lys Ala
225                 230                 235                 240

Thr Ser Thr Thr Ser Thr Ala Ser Pro Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
    290                 295
```

<210> SEQ ID NO 47
<211> LENGTH: 295
<212> TYPE: PRT
<213> ORGANISM: artificial sequence
<220> FEATURE:
<223> OTHER INFORMATION: variant of STCE1

<400> SEQUENCE: 47

```
Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Asp
            20                  25                  30

Ala Asn Phe Gln Arg Ile Ser Asp Pro Asn Val Lys Ser Gly Cys Asp
        35                  40                  45
```

```
Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
 65                  70                  75                  80

Glu Ala Ser Trp Cys Cys Gly Cys Tyr Glu Leu Thr Phe Thr Ser Gly
                 85                  90                  95

Pro Val Ala Gly Lys Thr Met Val Val Gln Ser Thr Ser Thr Gly Gly
                100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Pro Gly Asp
    130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
    195                 200                 205

Phe Thr Pro Pro Ser Gly Gly Gln Ser Ser Ser Ser Ser Ser Ser Ser
210                 215                 220

Ser Ala Lys Pro Thr Ser Thr Ser Thr Ser Thr Ser Thr Ser Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
                260                 265                 270

Ser Gly Cys Thr Thr Cys Val Ser Gly Thr Thr Cys Asn Lys Gln Asn
            275                 280                 285

Asp Trp Tyr Ser Gln Cys Leu
    290                 295

<210> SEQ ID NO 48
<211> LENGTH: 295
<212> TYPE: PRT
<213> ORGANISM: artificial sequence
<220> FEATURE:
<223> OTHER INFORMATION: variant of STCE1

<400> SEQUENCE: 48

Ala Asp Gly Lys Ser Thr Arg Tyr Trp Asp Cys Cys Lys Pro Ser Cys
 1               5                  10                  15

Ser Trp Pro Gly Lys Ala Ser Val Asn Gln Pro Val Phe Ala Cys Asp
                20                  25                  30

Ala Asn Phe Thr Arg Ile Ser Asp Pro Asn Val Lys Ser Gly Cys Asp
             35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
 65                  70                  75                  80

Glu Ala Ser Trp Cys Cys Gly Cys Tyr Glu Leu Thr Phe Thr Ser Gly
                 85                  90                  95

Pro Val Ala Gly Lys Thr Met Val Val Gln Ser Thr Ser Thr Gly Ser
                100                 105                 110
```

```
Asp Leu Gly Thr Asn His Phe Asp Leu Ala Met Pro Gly Gly Val
            115                 120                 125

Gly Ile Phe Asp Gly Cys Ser Pro Gln Phe Gly Leu Pro Gly Asp
        130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Ser Thr Ser Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
        260                 265                 270

Ser Gly Cys Thr Thr Cys Val Ser Gly Thr Thr Cys Asn Lys Gln Asn
        275                 280                 285

Asp Trp Tyr Ser Gln Cys Leu
        290                 295

<210> SEQ ID NO 49
<211> LENGTH: 295
<212> TYPE: PRT
<213> ORGANISM: artificial sequence
<220> FEATURE:
<223> OTHER INFORMATION: variant of STCE1

<400> SEQUENCE: 49

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Asp
            20                  25                  30

Ala Asn Phe Thr Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Met Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Val
            115                 120                 125

Gly Ile Phe Asp Gly Cys Thr Pro Gln Phe Gly Leu Pro Gly Asp
        130                 135                 140

Arg Tyr Gly Gly Val Ser Ser Arg Ser Gln Cys Asp Ser Phe Pro Ala
145                 150                 155                 160

Pro Leu Lys Pro Gly Cys Tyr Trp Arg Phe Asp Trp Phe Lys Asn Ala
                165                 170                 175
```

-continued

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Ser Thr Ser Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
        260                 265                 270

Ser Gly Cys Thr Thr Cys Val Ser Gly Thr Thr Cys Asn Lys Gln Asn
    275                 280                 285

Asp Trp Tyr Ser Gln Cys Leu
        290                 295

<210> SEQ ID NO 50
<211> LENGTH: 295
<212> TYPE: PRT
<213> ORGANISM: artificial sequence
<220> FEATURE:
<223> OTHER INFORMATION: variant of STCE1

<400> SEQUENCE: 50

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Trp Ala Cys Ser
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Met Gly Gly Asn
65                  70                  75                  80

Glu Ala Ser Trp Cys Cys Gly Cys Tyr Glu Leu Thr Phe Thr Ser Gly
                85                  90                  95

Pro Val Glu Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
        115                 120                 125

Gly Ile Phe Asp Gly Cys Ser Pro Gln Phe Gly Gly Leu Pro Gly Asp
    130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Ser Thr Ser Thr Lys Ala
225                 230                 235                 240

```
Thr Ser Thr Thr Ser Thr Ala Ser Ser Gln Thr Ser Ser Ser Thr Gly
            245                 250                 255

Gly Gly Cys Ala Ala Gln Arg Trp Ala Gln Cys Gly Gly Ile Gly Phe
        260                 265                 270

Ser Gly Cys Thr Thr Cys Val Ser Gly Thr Thr Cys Asn Lys Gln Asn
        275                 280                 285

Asp Trp Tyr Ser Gln Cys Leu
        290             295

<210> SEQ ID NO 51
<211> LENGTH: 295
<212> TYPE: PRT
<213> ORGANISM: artificial sequence
<220> FEATURE:
<223> OTHER INFORMATION: variant of STCE1

<400> SEQUENCE: 51

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Ser
            100                 105                 110

Asp Leu Gly Thr Asn His Phe Asp Leu Ala Met Pro Gly Gly Gly Val
        115                 120                 125

Gly Ile Phe Asp Gly Cys Ser Lys Gln Phe Gly Gly Leu Glu Gly Asp
    130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Ser Thr Ser Thr Lys Ala
225                 230                 235                 240

Thr Ser Thr Thr Ser Thr Ala Ser Ser Gln Thr Ser Ser Ser Thr Gly
            245                 250                 255

Gly Gly Cys Ala Ala Gln Arg Trp Ala Gln Cys Gly Gly Ile Gly Phe
        260                 265                 270

Ser Gly Cys Thr Thr Cys Val Ser Gly Thr Thr Cys Asn Lys Gln Asn
        275                 280                 285

Asp Trp Tyr Ser Gln Cys Leu
        290             295
```

<210> SEQ ID NO 52
<211> LENGTH: 295
<212> TYPE: PRT
<213> ORGANISM: artificial sequence
<220> FEATURE:
<223> OTHER INFORMATION: variant of STCE1

<400> SEQUENCE: 52

```
Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
        115                 120                 125

Gly Ile Phe Asp Gly Cys Thr Pro Gln Phe Gly Gly Leu Pro Gly Asp
    130                 135                 140

Arg Tyr Gly Gly Val Ser Ser Arg Ser Gln Cys Asp Ser Phe Pro Ala
145                 150                 155                 160

Ala Leu Val Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Ser Thr Ser Thr Ser Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
                260                 265                 270

Ser Gly Cys Thr Thr Cys Val Ser Gly Thr Thr Cys Asn Lys Gln Asn
            275                 280                 285

Asp Trp Tyr Ser Gln Cys Leu
    290                 295
```

<210> SEQ ID NO 53
<211> LENGTH: 295
<212> TYPE: PRT
<213> ORGANISM: artificial sequence
<220> FEATURE:
<223> OTHER INFORMATION: variant of STCE1

<400> SEQUENCE: 53

```
Ala Asp Gly Val Ser Thr Arg Tyr Trp Asp Cys Cys Lys Pro Ser Cys
1               5                   10                  15
```

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Gln Ser Thr Ser Thr Gly Ser
            100                 105                 110

Asp Leu Gly Thr Asn His Phe Asp Leu Ala Met Pro Gly Gly Val
        115                 120                 125

Gly Ile Phe Asp Gly Cys Thr Pro Gln Phe Gly Gly Leu Pro Gly Asp
    130                 135                 140

Arg Tyr Gly Gly Val Ser Ser Arg Ser Gln Cys Asp Ser Phe Pro Ala
145                 150                 155                 160

Pro Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Ser Thr Ser Thr Lys Ala
225                 230                 235                 240

Thr Ser Thr Thr Ser Thr Ala Ser Ser Gln Thr Ser Ser Thr Gly
            245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
            275                 280                 285

Asp Trp Tyr Ser Gln Cys Leu
    290                 295

<210> SEQ ID NO 54
<211> LENGTH: 295
<212> TYPE: PRT
<213> ORGANISM: artificial sequence
<220> FEATURE:
<223> OTHER INFORMATION: variant of STCE1

<400> SEQUENCE: 54

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Asp
            20                  25                  30

Ala Asn Phe Thr Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
50                  55                  60

Asp Asn Phe Ser Tyr Gly Phe Ala Ala Thr Ser Ile Ser Gly Gly Asn
65                  70                  75                  80

```
Glu Ala Ser Trp Cys Cys Gly Cys Tyr Glu Leu Thr Phe Thr Ser Gly
                85                  90                  95

Pro Val Glu Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
        115                 120                 125

Gly Ile Phe Asp Gly Cys Ser Lys Gln Phe Gly Gly Leu Pro Gly Asp
    130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Ser Thr Thr Ser Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
    290                 295

<210> SEQ ID NO 55
<211> LENGTH: 295
<212> TYPE: PRT
<213> ORGANISM: artificial sequence
<220> FEATURE:
<223> OTHER INFORMATION: variant of STCE1

<400> SEQUENCE: 55

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Ser
            100                 105                 110

Asp Leu Gly Thr Asn His Phe Asp Leu Ala Met Pro Gly Gly Gly Val
        115                 120                 125

Gly Ile Phe Asp Gly Cys Ser Lys Gln Phe Gly Gly Leu Pro Gly Asp
    130                 135                 140
```

```
Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
            165                 170                 175

Asp Asn Pro Thr Phe Thr Phe Arg Gln Val Gln Cys Pro Ser Glu Leu
        180                 185                 190

Val Ala Arg Thr Gly Cys Arg Arg Asn Asp Asp Gly Asn Phe Pro Val
        195                 200                 205

Phe Thr Pro Pro Ser Gly Gly Gln Met Ser Ser Ser Met Ser Ser Ser
    210                 215                 220

Ser Ala Lys Pro Thr Ser Thr Ser Thr Ser Thr Thr Ser Thr Lys Ala
225                 230                 235                 240

Leu Ser Thr Thr Ser Thr Ala Ser Ser Gln Thr Ser Ser Ser Thr Gly
                245                 250                 255

Lys Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
    290                 295

<210> SEQ ID NO 56
<211> LENGTH: 295
<212> TYPE: PRT
<213> ORGANISM: artificial sequence
<220> FEATURE:
<223> OTHER INFORMATION: variant of STCE1

<400> SEQUENCE: 56

Ala Asp Gly Val Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Lys Gly Gly Asn
65              70                  75                  80

Glu Ala Ser Trp Cys Cys Gly Cys Tyr Glu Leu Thr Phe Thr Ser Gly
            85                  90                  95

Pro Val Ala Gly Lys Thr Met Val Val Gln Ser Thr Ser Thr Gly Ser
            100                 105                 110

Asp Leu Gly Thr Asn His Phe Asp Leu Ala Met Pro Gly Gly Gly Val
        115                 120                 125

Gly Ile Phe Asp Gly Cys Ser Pro Gln Phe Gly Gly Leu Pro Gly Asp
    130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
            165                 170                 175

Asp Asn Pro Thr Phe Thr Phe Arg Gln Val Gln Cys Pro Ser Glu Leu
        180                 185                 190

Val Ser Arg Thr Gly Cys Arg Arg Asn Asp Asp Gly Asn Phe Pro Val
        195                 200                 205
```

```
Phe Thr Pro Pro Ser Gly Gly Gln Ser Ser Ser Ser Ser Ser Ser
    210                 215                 220

Ser Ala Lys Pro Thr Ser Thr Ser Thr Thr Ser Thr Lys Ala
225                 230                 235                 240

Thr Ser Thr Thr Ser Thr Ala Ser Gly Gln Thr Ser Ser Thr Gly
                245                 250                 255

Lys Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
            275                 280                 285

Asp Trp Tyr Ser Gln Cys Leu
            290             295

<210> SEQ ID NO 57
<211> LENGTH: 295
<212> TYPE: PRT
<213> ORGANISM: artificial sequence
<220> FEATURE:
<223> OTHER INFORMATION: variant of STCE1

<400> SEQUENCE: 57

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
                20                  25                  30

Ala Asn Phe Gln Arg Ile Ser Asp Pro Asn Val Lys Ser Gly Cys Asp
                35                  40                  45

Gly Gly Ser Ala Tyr Ala Cys Ala Asp Gln Thr Pro Trp Ala Val Asn
        50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Ser Val Ala Gly Lys Thr Met Val Val Gln Ser Thr Ser Thr Gly Val
                100                 105                 110

Asp Leu Gly Thr Asn His Phe Asp Leu Ala Met Pro Gly Gly Gly Val
            115                 120                 125

Gly Ile Phe Asp Gly Cys Ser Ser Gln Phe Gly Gly Leu Pro Gly Asp
            130                 135                 140

Arg Tyr Gly Gly Val Ser Ser Arg Ser Gln Cys Asp Ser Phe Pro Ala
145                 150                 155                 160

Glu Leu Val Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
            195                 200                 205

Phe Thr Pro Ser Ser Gly Gly Gln Ser Ser Ser Ser Ala Ser Ser
    210                 215                 220

Ser Ala Lys Pro Thr Ser Thr Ser Thr Thr Ser Thr Lys Ala
225                 230                 235                 240

Thr Ser Thr Thr Ser Thr Ala Ser Ser Gln Thr Ser Ser Thr Gly
                245                 250                 255

Gly Gly Cys Ala Ala Gln Arg Trp Ala Gln Cys Gly Gly Ile Gly Phe
            260                 265                 270
```

```
Ser Gly Cys Thr Thr Cys Val Ser Gly Thr Thr Cys Asn Lys Gln Asn
        275                 280                 285

Asp Trp Tyr Ser Gln Cys Leu
        290                 295

<210> SEQ ID NO 58
<211> LENGTH: 295
<212> TYPE: PRT
<213> ORGANISM: artificial sequence
<220> FEATURE:
<223> OTHER INFORMATION: variant of STCE1

<400> SEQUENCE: 58

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Ser Val Ala Gly Lys Thr Met Val Val Gln Ser Thr Ser Thr Gly Val
            100                 105                 110

Asp Leu Gly Thr Asn His Phe Asp Leu Ala Met Pro Gly Gly Gly Val
        115                 120                 125

Gly Ile Phe Asp Gly Cys Ser Ser Gln Phe Gly Gly Leu Ala Gly Asp
    130                 135                 140

Arg Tyr Gly Gly Val Ser Ser Arg Asp Gln Cys Asp Ser Phe Pro Ala
145                 150                 155                 160

Glu Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Lys Ala Lys Pro Thr Ser Thr Ser Thr Ser Thr Ser Thr Ser Lys Ala
225                 230                 235                 240

Arg Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
        290                 295

<210> SEQ ID NO 59
<211> LENGTH: 295
<212> TYPE: PRT
<213> ORGANISM: artificial sequence
```

```
<220> FEATURE:
<223> OTHER INFORMATION: variant of STCE1

<400> SEQUENCE: 59

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45

Gly Gly Ser Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Ser Val Ala Gly Lys Thr Met Val Val Gln Ser Thr Ser Thr Gly Val
            100                 105                 110

Asp Leu Gly Thr Asn His Phe Asp Leu Ala Met Pro Gly Gly Gly Val
        115                 120                 125

Gly Ile Phe Asp Gly Cys Ser Ser Gln Phe Gly Gly Leu Ala Gly Asp
    130                 135                 140

Arg Tyr Gly Gly Val Ser Ser Arg Asp Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Lys Ala Lys Pro Thr Ser Thr Ser Thr Ser Thr Ser Thr Ser Lys Ala
225                 230                 235                 240

Arg Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
    290                 295

<210> SEQ ID NO 60
<211> LENGTH: 295
<212> TYPE: PRT
<213> ORGANISM: artificial sequence
<220> FEATURE:
<223> OTHER INFORMATION: variant of STCE1

<400> SEQUENCE: 60

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Asp
            20                  25                  30

Ala Asn Phe Gln Arg Ile Ser Asp Pro Asn Val Lys Ser Gly Cys Asp
```

```
            35                  40                  45
Gly Gly Ser Ala Tyr Ala Cys Ala Asp Gln Thr Pro Trp Ala Val Asn
 50                  55                  60

Asp Asn Phe Ser Tyr Gly Phe Ala Ala Thr Ser Ile Ser Gly Gly Asn
 65                  70                  75                  80

Glu Ala Ser Trp Cys Cys Gly Cys Tyr Glu Leu Thr Phe Thr Ser Gly
                 85                  90                  95

Pro Val Ala Gly Lys Thr Met Val Val Gln Ser Thr Ser Thr Gly Gly
                100                 105                 110

Asp Leu Gly Thr Asn His Phe Asp Leu Ala Met Pro Gly Gly Gly Val
            115                 120                 125

Gly Ile Phe Asp Gly Cys Ser Pro Gln Phe Gly Leu Glu Gly Asp
        130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Lys
        195                 200                 205

Phe Thr Pro Pro Ser Gly Gly Gln Ser Ser Ser Ser Ser Ser Ser Ser
210                 215                 220

Lys Ala Lys Pro Thr Ser Thr Ser Thr Ser Thr Ser Thr Lys Ala
225                 230                 235                 240

Arg Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
    290                 295

<210> SEQ ID NO 61
<211> LENGTH: 295
<212> TYPE: PRT
<213> ORGANISM: artificial sequence
<220> FEATURE:
<223> OTHER INFORMATION: variant of STCE1

<400> SEQUENCE: 61

Ala Asp Gly Lys Ser Thr Arg Tyr Trp Asp Cys Cys Lys Pro Ser Cys
 1               5                  10                  15

Ser Trp Pro Gly Lys Ala Ser Val Asn Gln Pro Val Phe Ala Cys Asp
                20                  25                  30

Ala Asn Phe Gln Arg Ile Ser Asp Pro Asn Val Lys Ser Gly Cys Asp
            35                  40                  45

Gly Gly Ser Ala Tyr Ala Cys Ala Asp Gln Thr Pro Trp Ala Val Asn
 50                  55                  60

Asp Asn Phe Ser Tyr Gly Phe Ala Ala Thr Ser Ile Ser Gly Gly Asn
 65                  70                  75                  80

Glu Ala Ser Trp Cys Cys Gly Cys Tyr Glu Leu Thr Phe Thr Ser Gly
                 85                  90                  95

Pro Val Ala Gly Lys Thr Met Val Val Gln Ser Thr Ser Thr Gly Gly
```

```
                    100                 105                 110
Asp Leu Gly Thr Asn His Phe Asp Leu Ala Met Pro Gly Gly Gly Val
            115                 120                 125

Gly Ile Phe Asp Gly Cys Ser Pro Gln Phe Gly Gly Leu Glu Gly Asp
    130                 135                 140

Arg Tyr Gly Gly Val Ser Ser Arg Ser Gln Cys Asp Ser Phe Pro Ala
145                 150                 155                 160

Ala Leu Lys Pro Gly Cys Tyr Trp Arg Phe Asp Trp Phe Lys Asn Ala
            165                 170                 175

Asp Asn Pro Thr Phe Thr Phe Arg Gln Val Gln Cys Pro Ser Glu Leu
        180                 185                 190

Val Ala Arg Thr Gly Cys Arg Arg Asn Asp Asp Gly Asn Phe Pro Val
            195                 200                 205

Phe Thr Pro Pro Ser Gly Gly Gln Ser Ser Ser Ser Ser Ser Ser Ser
        210                 215                 220

Ser Ala Lys Pro Thr Ser Thr Ser Thr Ser Thr Thr Ser Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
            260                 265                 270

Ser Gly Cys Thr Thr Cys Val Ser Gly Thr Thr Cys Asn Lys Gln Asn
        275                 280                 285

Asp Trp Tyr Ser Gln Cys Leu
            290                 295

<210> SEQ ID NO 62
<211> LENGTH: 295
<212> TYPE: PRT
<213> ORGANISM: artificial sequence
<220> FEATURE:
<223> OTHER INFORMATION: variant of STCE1

<400> SEQUENCE: 62

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
            20                  25                  30

Ala Asn Phe Gln Arg Ile Ser Asp Pro Asn Val Lys Ser Gly Cys Asp
        35                  40                  45

Gly Gly Thr Ala Tyr Ala Cys Ala Asp Gln Thr Pro Trp Ala Val Asn
    50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
            85                  90                  95

Pro Val Tyr Gly Lys Thr Met Val Val Gln Ser Thr Ser Thr Gly Gly
            100                 105                 110

Asp Leu Gly Thr Asn His Leu Asp Leu Ala Met Pro Gly Gly Gly Val
            115                 120                 125

Gly Ile Phe Asp Gly Cys Ser Glu Gln Phe Gly Gly Leu Ala Gly Asp
    130                 135                 140

Arg Tyr Gly Gly Val Ser Ser Arg Ser Glu Cys Gly Ser Phe Pro Ala
145                 150                 155                 160

Ala Leu Lys Pro Gly Cys Tyr Trp Arg Phe Asp Trp Phe Lys Asn Ala
```

```
            165                 170                 175
Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
            195                 200                 205

Phe Thr Pro Pro Ser Gly Gly Gln Gly Ser Ser Ser Ser Ser Ser Ser
            210                 215                 220

Ser Ala Lys Pro Thr Ser Thr Ser Thr Ser Thr Ser Thr Thr Lys Ala
225                 230                 235                 240

Thr Ser Thr Thr Ser Thr Ala Ser Ser Gln Thr Ser Ser Ser Thr Gly
                245                 250                 255

Gly Gly Cys Ala Ala Gln Arg Trp Ala Gln Cys Gly Gly Ile Gly Phe
                260                 265                 270

Ser Gly Cys Thr Thr Cys Val Ser Gly Thr Thr Cys Asn Lys Gln Asn
                275                 280                 285

Asp Trp Tyr Ser Gln Cys Leu
                290                 295

<210> SEQ ID NO 63
<211> LENGTH: 295
<212> TYPE: PRT
<213> ORGANISM: artificial sequence
<220> FEATURE:
<223> OTHER INFORMATION: variant of STCE1

<400> SEQUENCE: 63

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
                20                  25                  30

Ala Asn Phe Gln Arg Ile Ser Asp Pro Asn Val Val Ser Gly Cys Asp
                35                  40                  45

Gly Gly Ser Ala Tyr Ala Cys Ala Asp Gln Thr Pro Trp Ala Val Asn
            50                  55                  60

Asp Asn Phe Ser Tyr Gly Phe Ala Ala Thr Ser Ile Ser Gly Gly Asn
65              70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Gly
                100                 105                 110

Asp Leu Gly Thr Asn His Phe Asp Leu Ala Met Pro Gly Gly Gly Val
                115                 120                 125

Gly Ile Phe Asp Gly Cys Ser Pro Gln Phe Gly Gly Leu Pro Gly Asp
            130                 135                 140

Arg Tyr Gly Gly Val Ser Ser Arg Ser Gln Cys Asp Ser Phe Pro Ala
145                 150                 155                 160

Pro Leu Val Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
                180                 185                 190

Val Ala Arg Thr Gly Cys Arg Arg Asn Asp Asp Gly Asn Phe Pro Val
                195                 200                 205

Phe Thr Pro Pro Ser Gly Gly Gln Ser Ser Ser Ser Ser Ser Ser Ser
            210                 215                 220

Ser Ala Arg Pro Thr Ser Thr Ser Thr Ser Thr Ala Ser Thr Lys Ala
```

-continued

```
            225                 230                 235                 240
        Thr Ser Thr Thr Ser Thr Ala Ser Ser Gln Thr Ser Ser Ser Thr Gly
                        245                 250                 255

Gly Gly Cys Ala Ala Gln Arg Trp Ala Gln Cys Gly Gly Ile Gly Phe
                    260                 265                 270

Ser Gly Cys Thr Thr Cys Val Ser Gly Thr Thr Cys Asn Lys Gln Asn
                        275                 280                 285

Asp Trp Tyr Ser Gln Cys Leu
                        290                 295

<210> SEQ ID NO 64
<211> LENGTH: 301
<212> TYPE: PRT
<213> ORGANISM: artificial sequence
<220> FEATURE:
<223> OTHER INFORMATION: variant of STCE1

<400> SEQUENCE: 64

Ala Asp Gly Lys Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Ser
                20                  25                  30

Ala Asn Phe Gln Arg Ile Ser Asp Pro Asn Val Lys Ser Gly Cys Asp
            35                  40                  45

Gly Gly Ser Ala Tyr Ala Cys Ala Asp Gln Thr Pro Trp Ala Val Asn
        50                  55                  60

Asp Asn Phe Ser Tyr Gly Phe Ala Ala Thr Ser Ile Ser Gly Gly Asn
65                  70                  75                  80

Glu Ala Ser Trp Cys Cys Gly Cys Tyr Glu Leu Thr Phe Thr Ser Gly
                85                  90                  95

Pro Val Ala Gly Lys Thr Met Val Val Gln Ser Thr Ser Thr Gly Thr
                100                 105                 110

Asp Leu Gly Thr Asn His Phe Asp Leu Ala Met Pro Gly Gly Gly Val
            115                 120                 125

Gly Ile Phe Asp Gly Cys Thr Pro Gln Phe Gly Gly Leu Ala Gly Asp
        130                 135                 140

Arg Tyr Gly Gly Val Ser Ser Arg Ser Glu Cys Asp Ser Phe Pro Ala
145                 150                 155                 160

Ala Leu Lys Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Lys Pro Thr Ser Thr Ser Thr Thr Ser Thr Ser Thr Thr Ser
225                 230                 235                 240

Thr Thr Asp Thr Lys Ala Thr Ser Thr Thr Ala Ser Ser Gln
                245                 250                 255

Thr Ser Ser Ser Thr Gly Gly Cys Ala Ala Gln Arg Trp Ala Gln
                260                 265                 270

Cys Gly Gly Ile Gly Phe Ser Gly Cys Thr Thr Cys Val Ser Gly Thr
                275                 280                 285

Thr Cys Asn Lys Gln Asn Asp Trp Tyr Ser Gln Cys Leu
```

<210> SEQ ID NO 65
<211> LENGTH: 305
<212> TYPE: PRT
<213> ORGANISM: artificial sequence
<220> FEATURE:
<223> OTHER INFORMATION: variant of STCE1

<400> SEQUENCE: 65

```
Ala Asp Gly Lys Ser Thr Arg Tyr Trp Asp Cys Cys Lys Pro Ser Cys
1               5                   10                  15
Ser Trp Pro Gly Lys Ala Ser Val Asn Gln Pro Val Phe Ala Cys Ser
            20                  25                  30
Ala Asn Phe Thr Arg Ile Ser Asp Pro Asn Val Lys Ser Gly Cys Asp
        35                  40                  45
Gly Gly Thr Ala Tyr Ala Cys Ala Asp Gln Thr Pro Trp Ala Val Asn
    50                  55                  60
Asp Asn Phe Ser Tyr Gly Phe Ala Ala Thr Ser Ile Ser Gly Gly Asn
65                  70                  75                  80
Glu Ala Ser Trp Cys Cys Gly Cys Tyr Glu Leu Thr Phe Thr Ser Gly
                85                  90                  95
Pro Gly Ala Gly Lys Thr Met Val Val Gln Ser Thr Ser Thr Gly Gly
            100                 105                 110
Asp Leu Gly Val Asn His Phe Asp Leu Ala Met Pro Gly Gly Gly Val
        115                 120                 125
Gly Ile Phe Asp Gly Cys Ser Pro Gln Phe Gly Leu Pro Gly Asp
    130                 135                 140
Arg Tyr Gly Gly Val Ser Ser Arg Ser Gln Cys Asp Ser Phe Pro Ala
145                 150                 155                 160
Pro Leu Lys Pro Gly Cys Tyr Trp Arg Phe Asp Trp Phe Lys Asn Ala
                165                 170                 175
Asp Asn Pro Thr Phe Thr Phe Arg Gln Val Gln Cys Pro Ser Glu Leu
            180                 185                 190
Val Ala Arg Thr Gly Cys Arg Arg Asn Asp Asp Gly Asn Phe Pro Val
        195                 200                 205
Phe Thr Pro Pro Ser Gly Gly Gln Ser Ser Ser Ser Ser Ser Ser
    210                 215                 220
Ser Ala Lys Pro Thr Thr Thr Ser Thr Ala Ser Thr Lys Ala Thr
225                 230                 235                 240
Ser Thr Thr Ser Thr Thr Ser Thr Lys Ala Thr Ser Thr Thr Ser Thr
                245                 250                 255
Ala Ser Ser Gln Thr Ser Ser Ser Thr Gly Gly Gly Cys Ala Ala Gln
            260                 265                 270
Arg Trp Ala Gln Cys Gly Gly Ile Gly Phe Ser Gly Cys Thr Thr Cys
        275                 280                 285
Val Ser Gly Thr Thr Cys Asn Lys Gln Asn Asp Trp Tyr Ser Gln Cys
    290                 295                 300
Leu
305
```

<210> SEQ ID NO 66
<211> LENGTH: 306
<212> TYPE: PRT
<213> ORGANISM: artificial sequence
<220> FEATURE:
<223> OTHER INFORMATION: variant of STCE1

<400> SEQUENCE: 66

```
Ala Asp Gly Val Ser Thr Arg Tyr Trp Asp Cys Cys Lys Pro Ser Cys
1               5                   10                  15
Ser Trp Pro Gly Lys Ala Ser Val Asn Gln Pro Val Trp Ala Cys Ser
            20                  25                  30
Ala Asn Phe Gln Arg Ile Ser Asp Pro Asn Val Lys Ser Gly Cys Asp
        35                  40                  45
Gly Gly Thr Ala Tyr Ala Cys Ala Asp Gln Thr Pro Trp Ala Val Asn
    50                  55                  60
Gly Asn Phe Ser Tyr Gly Phe Ala Ala Thr Ser Ile Met Gly Gly Asn
65              70                  75                  80
Glu Ala Ser Trp Cys Cys Gly Cys Tyr Glu Leu Thr Phe Thr Ser Gly
                85                  90                  95
Pro Val Ala Gly Lys Thr Met Val Val Gln Ser Thr Ser Thr Gly Gly
            100                 105                 110
Asp Leu Gly Val Asn His Phe Asp Leu Ala Met Pro Gly Gly Gly Val
        115                 120                 125
Gly Ile Phe Asp Gly Cys Ser Pro Gln Phe Gly Gly Leu Ala Gly Asp
    130                 135                 140
Arg Tyr Gly Gly Val Ser Ser Arg Asp Gln Cys Asp Ser Phe Pro Ala
145                 150                 155                 160
Ala Leu Val Pro Gly Cys Tyr Trp Arg Phe Asp Trp Phe Lys Asn Ala
                165                 170                 175
Asp Asn Pro Thr Phe Thr Phe Arg Gln Val Gln Cys Pro Ser Glu Leu
            180                 185                 190
Val Ala Arg Thr Gly Cys Arg Arg Asn Asp Asp Ser Asn Ser Pro Val
        195                 200                 205
Phe Val Pro Pro Ser Gly Gln Ser Ser Ser Leu Ser Ser Ser
    210                 215                 220
Ser Ala Lys Pro Thr Ser Thr Ser Thr Ser Thr Ser Thr Thr Lys Ala
225                 230                 235                 240
Thr Ser Thr Thr Ser Thr Ser Thr Lys Ala Thr Ser Thr Thr Ser
                245                 250                 255
Thr Ala Ser Ser Gln Thr Ser Ser Ser Thr Gly Gly Gly Cys Ala Ala
            260                 265                 270
Gln Arg Trp Ala Gln Cys Gly Gly Ile Gly Phe Ser Gly Cys Thr Thr
        275                 280                 285
Cys Val Ser Gly Thr Thr Cys Asn Lys Gln Asn Asp Trp Tyr Ser Gln
    290                 295                 300
Cys Leu
305
```

<210> SEQ ID NO 67
<211> LENGTH: 306
<212> TYPE: PRT
<213> ORGANISM: artificial sequence
<220> FEATURE:
<223> OTHER INFORMATION: variant of STCE1

<400> SEQUENCE: 67

```
Ala Asp Gly Lys Ser Thr Arg Tyr Trp Asp Cys Cys Lys Pro Ser Cys
1               5                   10                  15
Ser Trp Pro Gly Lys Ala Ser Val Asn Gln Pro Val Phe Ala Cys Ser
            20                  25                  30
```

Ala Asn Phe Gln Arg Ile Ser Asp Pro Asn Val Lys Ser Gly Cys Asp
             35                  40                  45

Gly Gly Ser Ala Tyr Ala Cys Ala Asp Gln Thr Pro Trp Ala Val Asn
         50                  55                  60

Asp Asn Phe Ser Tyr Gly Phe Ala Ala Thr Ser Ile Met Gly Gly Asn
 65                  70                  75                  80

Glu Ala Ser Trp Cys Cys Gly Cys Tyr Glu Leu Thr Phe Thr Ser Gly
                 85                  90                  95

Pro Val Ala Gly Lys Thr Met Val Val Gln Ser Thr Ser Thr Gly Gly
            100                 105                 110

Asp Leu Gly Thr Asn His Phe Asp Leu Ala Met Pro Gly Gly Gly Val
        115                 120                 125

Gly Ile Phe Asp Gly Cys Thr Pro Gln Phe Gly Gly Leu Ala Gly Asp
    130                 135                 140

Arg Tyr Gly Gly Val Ser Ser Arg Ser Glu Cys Asp Ser Phe Pro Ala
145                 150                 155                 160

Ala Leu Val Pro Gly Cys Tyr Trp Arg Phe Asp Trp Phe Lys Asn Ala
                165                 170                 175

Asp Asn Pro Thr Phe Thr Phe Arg Gln Val Gln Cys Pro Ser Glu Leu
            180                 185                 190

Val Ala Arg Thr Gly Cys Arg Arg Asn Asp Asp Gly Asn Phe Pro Val
        195                 200                 205

Phe Thr Pro Pro Ser Gly Gly Gln Ser Ser Ser Ser Ser Ser Ser Ser
    210                 215                 220

Ser Ala Arg Pro Thr Ser Thr Ser Thr Ser Thr Thr Ser Asp Lys Ala
225                 230                 235                 240

Thr Ser Thr Thr Ser Thr Thr Asp Thr Lys Ala Thr Ser Thr Thr Ser
                245                 250                 255

Thr Ala Ser Ser Gln Thr Ser Ser Thr Gly Gly Gly Cys Ala Ala
            260                 265                 270

Gln Arg Trp Ala Gln Cys Gly Gly Ile Gly Phe Ser Gly Cys Thr Thr
        275                 280                 285

Cys Val Ser Gly Thr Thr Cys Asn Lys Gln Asn Asp Trp Tyr Ser Gln
    290                 295                 300

Cys Leu
305

<210> SEQ ID NO 68
<211> LENGTH: 306
<212> TYPE: PRT
<213> ORGANISM: artificial sequence
<220> FEATURE:
<223> OTHER INFORMATION: variant of STCE1

<400> SEQUENCE: 68

Ala Asp Gly Val Ser Thr Arg Tyr Trp Asp Cys Cys Lys Pro Ser Cys
1               5                   10                  15

Ser Trp Pro Gly Lys Ala Ser Val Asn Gln Pro Val Phe Ala Cys Gly
            20                  25                  30

Ala Asn Phe Thr Arg Ile Ser Asp Pro Asn Val Lys Ser Gly Cys Asp
             35                  40                  45

Gly Gly Ser Ala Tyr Ala Cys Ala Asp Gln Thr Pro Trp Ala Val Asn
         50                  55                  60

Asp Asn Phe Ser Tyr Gly Phe Ala Ala Thr Ser Ile Met Gly Gly Asn
 65                  70                  75                  80

-continued

```
Glu Ala Ser Trp Cys Cys Ala Cys Tyr Glu Leu Thr Phe Thr Ser Gly
             85                  90                  95
Pro Val Ala Gly Lys Thr Met Val Val Gln Ser Thr Ser Thr Gly Gly
         100                 105                 110
Asp Leu Gly Val Asn His Phe Asp Leu Ala Met Pro Gly Gly Gly Val
         115                 120                 125
Gly Ile Phe Asp Gly Cys Ser Pro Gln Phe Gly Gly Leu Pro Gly Asp
    130                 135                 140
Arg Tyr Gly Gly Val Ser Ser Arg Ser Gln Cys Asp Ser Phe Pro Ala
145                 150                 155                 160
Pro Leu Lys Pro Gly Cys Tyr Trp Arg Phe Asp Trp Phe Lys Asn Ala
                165                 170                 175
Asp Asn Pro Thr Phe Thr Phe Arg Gln Val Gln Cys Pro Ser Glu Leu
            180                 185                 190
Val Ala Arg Thr Gly Cys Arg Arg Asn Asp Asp Gly Asn Phe Pro Val
        195                 200                 205
Phe Thr Pro Pro Ser Gly Gly Gln Ser Ser Ser Ser Ser Ser Ser Ser
    210                 215                 220
Ser Ala Lys Pro Thr Ser Thr Ser Thr Ser Thr Thr Asp Thr Lys Ala
225                 230                 235                 240
Thr Ser Thr Thr Ser Thr Thr Ser Thr Lys Ala Thr Ser Thr Thr Ser
                245                 250                 255
Thr Ala Ser Ser Gln Thr Ser Ser Ser Thr Gly Gly Cys Ala Ala
            260                 265                 270
Gln Arg Trp Ala Gln Cys Gly Gly Ile Gly Phe Ser Gly Cys Thr Thr
        275                 280                 285
Cys Val Ser Gly Thr Thr Cys Asn Lys Gln Asn Asp Trp Tyr Ser Gln
    290                 295                 300
Cys Leu
305

<210> SEQ ID NO 69
<211> LENGTH: 305
<212> TYPE: PRT
<213> ORGANISM: artificial sequence
<220> FEATURE:
<223> OTHER INFORMATION: variant of STCE1

<400> SEQUENCE: 69

Ala Asp Gly Lys Ser Thr Arg Tyr Trp Asp Cys Cys Lys Pro Ser Cys
1               5                   10                  15
Ser Trp Pro Gly Lys Ala Ser Val Asn Gln Pro Val Phe Ala Cys Ser
             20                  25                  30
Ala Asn Phe Gln Arg Ile Ser Asp Pro Asn Val Lys Ser Gly Cys Asp
         35                  40                  45
Gly Gly Ser Ala Tyr Ala Cys Ala Asp Gln Thr Pro Trp Ala Val Asn
     50                  55                  60
Asp Asn Phe Ser Tyr Gly Phe Ala Ala Thr Ser Ile Met Gly Gly Asn
65                  70                  75                  80
Glu Ala Ser Trp Cys Cys Ala Cys Tyr Glu Leu Thr Phe Thr Ser Gly
             85                  90                  95
Pro Val Ala Gly Lys Thr Met Val Val Gln Ser Thr Ser Thr Gly Gly
         100                 105                 110
Asp Leu Gly Thr Asn His Phe Asp Leu Ala Met Pro Gly Gly Gly Val
         115                 120                 125
```

```
Gly Ile Phe Asp Gly Cys Ser Glu Gln Phe Gly Gly Leu Ala Gly Asp
130                 135                 140

Arg Tyr Gly Gly Val Ser Ser Arg Ser Gln Cys Asp Asp Phe Pro Ala
145                 150                 155                 160

Ala Leu Lys Pro Gly Cys Tyr Trp Arg Phe Trp Phe Lys Asn Ala Asp
                165                 170                 175

Asn Pro Thr Phe Thr Phe Arg Gln Val Gln Cys Pro Ser Glu Leu Val
                180                 185                 190

Ala Arg Thr Gly Cys Arg Arg Asn Asp Asp Gly Asn Phe Pro Val Phe
                195                 200                 205

Thr Pro Pro Ser Gly Gly Gln Ser Ser Ser Leu Ser Ser Ser Ser
210                 215                 220

Ala Lys Pro Thr Ser Thr Ser Thr Ser Thr Thr Ser Thr Lys Ala Thr
225                 230                 235                 240

Ser Thr Thr Ser Thr Ala Ser Asp Lys Ala Thr Ser Thr Thr Ser Thr
                245                 250                 255

Ala Ser Ser Gln Thr Ser Ser Ser Thr Gly Gly Gly Cys Ala Ala Gln
                260                 265                 270

Arg Trp Ala Gln Cys Gly Gly Ile Gly Phe Ser Gly Cys Thr Thr Cys
                275                 280                 285

Val Ser Gly Thr Thr Cys Asn Glu Gln Asn Asp Trp Tyr Ser Gln Cys
290                 295                 300

Leu
305

<210> SEQ ID NO 70
<211> LENGTH: 293
<212> TYPE: PRT
<213> ORGANISM: Chaetomium thermophilum

<400> SEQUENCE: 70

Ala Asp Gly Lys Ser Thr Arg Tyr Trp Asp Cys Cys Lys Pro Ser Cys
1               5                   10                  15

Ser Trp Pro Gly Lys Ala Ala Val Ser Gln Pro Val Phe Ala Cys Asp
                20                  25                  30

Arg Asn Phe Asn Arg Ile Tyr Asp Phe Gly Ala Lys Ser Gly Cys Glu
                35                  40                  45

Gly Gly Pro Ala Tyr Ser Cys Ala Asp Gln Thr Pro Trp Ala Val Asn
50                  55                  60

Asp Gln Phe Ser Tyr Gly Phe Ala Ala Thr Asn Ile Ala Gly Gly Asn
65                  70                  75                  80

Glu Ala Ser Trp Cys Cys Ala Cys Tyr Lys Leu Thr Phe Thr Ser Gly
                85                  90                  95

Pro Val Ala Gly Lys Val Met Val Val Gln Ser Thr Ser Thr Gly Gly
                100                 105                 110

Asp Leu Gly Asn Asn His Phe Asp Leu Asn Ile Pro Gly Gly Gly Val
                115                 120                 125

Gly Ile Phe Asp Gly Cys Thr Pro Gln Phe Gly Gly Leu Pro Gly Glu
130                 135                 140

Arg Tyr Gly Gly Ile Ser Ser Arg Ser Gln Cys Asp Ser Phe Pro Asp
145                 150                 155                 160

Ala Leu Lys Pro Gly Cys Tyr Trp Arg Phe Asp Trp Phe Leu Asn Ala
                165                 170                 175

Asp Asn Pro Asn Phe Thr Phe Glu Arg Val Gln Cys Pro Ser Glu Leu
                180                 185                 190
```

```
Val Ala Arg Thr Gly Cys Lys Arg Asn Asp Asp Gly Asn Tyr Pro Val
            195                 200                 205

Phe Thr Pro Pro Ser Gly Asp Ser Pro Ser Ser Ser Ala Ala Pro
    210                 215                 220

Thr Ser Thr Ser Thr Ser Gln Gln Pro Gln Gln Pro Thr Ser Ser Ser
225                 230                 235                 240

Ser Gln Ala Ser Val Pro Thr Ser Asn Pro Gly Gly Cys Thr Ser Gln
                245                 250                 255

Lys Trp Ala Gln Cys Gly Gly Ile Gly Phe Thr Gly Cys Thr Thr Cys
                260                 265                 270

Val Ser Gly Thr Thr Cys Thr Lys Leu Asn Asp Trp Tyr Ser Gln Cys
                275                 280                 285

Thr Met Ile Asn Leu
            290

<210> SEQ ID NO 71
<211> LENGTH: 284
<212> TYPE: PRT
<213> ORGANISM: Humicola insolens

<400> SEQUENCE: 71

Ala Asp Gly Arg Ser Thr Arg Tyr Trp Asp Cys Cys Lys Pro Ser Cys
1               5                   10                  15

Gly Trp Ala Lys Lys Ala Pro Val Asn Gln Pro Val Phe Ser Cys Asn
                20                  25                  30

Ala Asn Phe Gln Arg Ile Thr Asp Phe Asp Ala Lys Ser Gly Cys Glu
            35                  40                  45

Pro Gly Gly Val Ala Tyr Ser Cys Ala Asp Gln Thr Pro Trp Ala Val
        50                  55                  60

Asn Asp Asp Phe Ala Leu Gly Phe Ala Ala Thr Ser Ile Ala Gly Ser
65                  70                  75                  80

Asn Glu Ala Gly Trp Cys Cys Ala Cys Tyr Glu Leu Thr Phe Thr Ser
                85                  90                  95

Gly Pro Val Ala Gly Lys Lys Met Val Val Gln Ser Thr Ser Thr Gly
                100                 105                 110

Gly Asp Leu Gly Ser Asn His Phe Asp Leu Asn Ile Pro Gly Gly Gly
            115                 120                 125

Val Gly Ile Phe Asp Gly Cys Thr Pro Gln Phe Gly Gly Leu Pro Gly
        130                 135                 140

Gln Arg Tyr Gly Gly Ile Ser Ser Arg Asn Glu Cys Asp Arg Phe Pro
145                 150                 155                 160

Asp Ala Leu Lys Pro Gly Cys Tyr Trp Arg Phe Asp Trp Phe Lys Asn
                165                 170                 175

Ala Asp Asn Pro Ser Phe Ser Phe Arg Gln Val Gln Cys Pro Ala Glu
                180                 185                 190

Leu Val Ala Arg Thr Gly Cys Arg Arg Asn Asp Asp Gly Asn Phe Pro
            195                 200                 205

Ala Val Gln Ile Pro Ser Ser Ser Thr Ser Ser Pro Val Asn Gln Pro
        210                 215                 220

Thr Ser Thr Ser Thr Ser Thr Ser Thr Ser Thr Ser Ser Pro Pro Val
225                 230                 235                 240

Gln Pro Thr Thr Pro Ser Gly Cys Thr Ala Glu Arg Trp Ala Gln Cys
                245                 250                 255

Gly Gly Asn Gly Trp Ser Gly Cys Thr Thr Cys Val Ala Gly Ser Thr
```

```
                260                 265                 270
Cys Thr Lys Ile Asn Asp Trp Tyr His Gln Cys Leu
        275                 280

<210> SEQ ID NO 72
<211> LENGTH: 284
<212> TYPE: PRT
<213> ORGANISM: Humicola grisea

<400> SEQUENCE: 72

Ala Asp Gly Lys Ser Thr Arg Tyr Trp Asp Cys Cys Lys Pro Ser Cys
1               5                   10                  15

Gly Trp Ala Lys Lys Ala Pro Val Asn Gln Pro Val Phe Ser Cys Asn
            20                  25                  30

Ala Asn Phe Gln Arg Leu Thr Asp Phe Asp Ala Lys Ser Gly Cys Glu
        35                  40                  45

Pro Gly Gly Val Ala Tyr Ser Cys Ala Asp Gln Thr Pro Trp Ala Val
    50                  55                  60

Asn Asp Asp Phe Ala Phe Gly Phe Ala Ala Thr Ser Ile Ala Gly Ser
65                  70                  75                  80

Asn Glu Ala Gly Trp Cys Cys Ala Cys Tyr Glu Leu Thr Phe Thr Ser
                85                  90                  95

Gly Pro Val Ala Gly Lys Lys Met Val Val Gln Ser Thr Ser Thr Gly
            100                 105                 110

Gly Asp Leu Gly Ser Asn His Phe Asp Leu Asn Ile Pro Gly Gly Gly
        115                 120                 125

Val Gly Ile Phe Asp Gly Cys Thr Pro Gln Phe Gly Gly Leu Pro Gly
    130                 135                 140

Gln Arg Tyr Gly Gly Ile Ser Ser Arg Asn Glu Cys Asp Arg Phe Pro
145                 150                 155                 160

Asp Ala Leu Lys Pro Gly Cys Tyr Trp Arg Phe Asp Trp Phe Lys Asn
                165                 170                 175

Ala Asp Asn Pro Ser Phe Ser Phe Arg Gln Val Gln Cys Pro Ala Glu
            180                 185                 190

Leu Val Ala Arg Thr Gly Cys Arg Arg Asn Asp Asp Gly Asn Phe Pro
        195                 200                 205

Ala Val Gln Ile Pro Ser Ser Ser Thr Ser Ser Pro Val Gly Gln Pro
    210                 215                 220

Thr Ser Thr Ser Thr Thr Ser Thr Ser Thr Thr Ser Ser Pro Pro Val
225                 230                 235                 240

Gln Pro Thr Thr Pro Ser Gly Cys Thr Ala Glu Arg Trp Ala Gln Cys
                245                 250                 255

Gly Gly Asn Gly Trp Ser Gly Cys Thr Thr Cys Val Ala Gly Ser Thr
            260                 265                 270

Cys Thr Lys Ile Asn Asp Trp Tyr His Gln Cys Leu
        275                 280

<210> SEQ ID NO 73
<211> LENGTH: 278
<212> TYPE: PRT
<213> ORGANISM: Thielavia terrestris

<400> SEQUENCE: 73

Ala Ser Gly Ser Gly Gln Ser Thr Arg Tyr Trp Asp Cys Cys Lys Pro
1               5                   10                  15

Ser Cys Ala Trp Pro Gly Lys Ala Ala Val Ser Gln Pro Val Tyr Ala
```

```
            20                  25                  30
Cys Asp Ala Asn Phe Gln Arg Leu Ser Asp Phe Asn Val Gln Ser Gly
         35                  40                  45

Cys Asn Gly Gly Ser Ala Tyr Ser Cys Ala Asp Gln Thr Pro Trp Ala
 50                  55                  60

Val Asn Asp Asn Leu Ala Tyr Gly Phe Ala Ala Thr Ser Ile Ala Gly
 65                  70                  75                  80

Gly Ser Glu Ser Ser Trp Cys Cys Ala Cys Tyr Ala Leu Thr Phe Thr
                 85                  90                  95

Ser Gly Pro Val Ala Gly Lys Thr Met Val Val Gln Ser Thr Ser Thr
             100                 105                 110

Gly Gly Asp Leu Gly Ser Asn Gln Phe Asp Ile Ala Met Pro Gly Gly
         115                 120                 125

Gly Val Gly Ile Phe Asn Gly Cys Ser Ser Gln Phe Gly Gly Leu Pro
     130                 135                 140

Gly Ala Gln Tyr Gly Gly Ile Ser Ser Arg Asp Gln Cys Asp Ser Phe
145                 150                 155                 160

Pro Ala Pro Leu Lys Pro Gly Cys Gln Trp Arg Phe Asp Trp Phe Gln
                 165                 170                 175

Asn Ala Asp Asn Pro Thr Phe Thr Phe Gln Gln Val Gln Cys Pro Ala
             180                 185                 190

Glu Ile Val Ala Arg Ser Gly Cys Lys Arg Asn Asp Asp Ser Ser Phe
         195                 200                 205

Pro Val Phe Thr Pro Pro Ser Gly Gly Asn Gly Gly Thr Gly Thr Pro
     210                 215                 220

Thr Ser Thr Ala Pro Gly Ser Gly Gln Thr Ser Pro Gly Gly Gly Ser
225                 230                 235                 240

Gly Cys Thr Ser Gln Lys Trp Ala Gln Cys Gly Gly Ile Gly Phe Ser
                 245                 250                 255

Gly Cys Thr Thr Cys Val Ser Gly Thr Thr Cys Gln Lys Leu Asn Asp
             260                 265                 270

Tyr Tyr Ser Gln Cys Leu
         275

<210> SEQ ID NO 74
<211> LENGTH: 294
<212> TYPE: PRT
<213> ORGANISM: Acremonium thermophilum

<400> SEQUENCE: 74

Leu Asp Gly Lys Ser Thr Arg Tyr Trp Asp Cys Cys Lys Pro Ser Cys
 1               5                  10                  15

Gly Trp Ala Gly Lys Ala Ser Val Asn Gln Pro Val Phe Ser Cys Ser
             20                  25                  30

Ala Asp Trp Gln Arg Ile Ser Asp Phe Asn Ala Lys Ser Gly Cys Asp
         35                  40                  45

Gly Gly Ser Ala Tyr Ser Cys Ala Asp Gln Thr Pro Trp Ala Val Asn
     50                  55                  60

Asp Asn Phe Ser Tyr Gly Phe Ala Ala Thr Ala Ile Ala Gly Gly Ser
 65                  70                  75                  80

Glu Ser Ser Trp Cys Cys Ala Cys Tyr Ala Leu Thr Phe Asn Ser Gly
                 85                  90                  95

Pro Val Ala Gly Lys Thr Met Val Val Gln Ser Thr Ser Thr Gly Gly
             100                 105                 110
```

```
Asp Leu Gly Ser Asn Gln Phe Asp Leu Ala Ile Pro Gly Gly Val
            115                 120                 125

Gly Ile Phe Asn Gly Cys Ala Ser Gln Phe Gly Gly Leu Pro Gly Ala
        130                 135                 140

Gln Tyr Gly Gly Ile Ser Asp Arg Ser Gln Cys Ser Ser Phe Pro Ala
145                 150                 155                 160

Pro Leu Gln Pro Gly Cys Gln Trp Arg Phe Asp Trp Phe Gln Asn Ala
                165                 170                 175

Asp Asn Pro Thr Phe Thr Phe Gln Arg Val Gln Cys Pro Ser Glu Leu
            180                 185                 190

Thr Ser Arg Thr Gly Cys Lys Arg Asp Asp Ala Ser Tyr Pro Val
        195                 200                 205

Phe Asn Pro Pro Ser Val Pro Gly Leu Asp Gly Ser Asn Pro Gly Asn
            210                 215                 220

Pro Thr Thr Thr Val Val Pro Pro Ala Ser Thr Ser Thr Ser Arg Pro
225                 230                 235                 240

Thr Ser Ser Thr Ser Ser Pro Val Ser Thr Pro Thr Gly Gln Pro Gly
                245                 250                 255

Gly Cys Thr Thr Gln Lys Trp Gly Gln Cys Gly Gly Ile Gly Tyr Thr
            260                 265                 270

Gly Cys Thr Asn Cys Val Ala Gly Thr Thr Cys Thr Gln Leu Asn Pro
        275                 280                 285

Trp Tyr Ser Gln Cys Leu
        290

<210> SEQ ID NO 75
<211> LENGTH: 272
<212> TYPE: PRT
<213> ORGANISM: Neurospora crassa

<400> SEQUENCE: 75

Ala Ser Gly Ser Gly Gln Ser Thr Arg Tyr Trp Asp Cys Cys Lys Pro
1               5                   10                  15

Ser Cys Ser Trp Ser Gly Lys Ala Pro Val Asn Arg Pro Val Leu Ala
            20                  25                  30

Cys Asp Ala Asn Asn Asn Pro Leu Ser Asp Ala Ser Val Lys Ser Gly
        35                  40                  45

Cys Asp Gly Gly Ser Ala Tyr Thr Cys Ala Asn Asn Ser Pro Trp Ala
    50                  55                  60

Val Asn Asp Gln Leu Ser Tyr Gly Phe Ala Ala Thr Lys Leu Ser Gly
65                  70                  75                  80

Gly Thr Glu Ser Ser Trp Cys Cys Ala Cys Tyr Ala Leu Thr Phe Thr
                85                  90                  95

Ser Gly Pro Val Ala Gly Lys Thr Leu Val Val Gln Ser Thr Ser Thr
            100                 105                 110

Gly Gly Asp Leu Gly Ser Asn His Phe Asp Ile Asn Met Pro Gly Gly
        115                 120                 125

Gly Val Gly Leu Phe Asp Gly Cys Lys Arg Gln Phe Gly Gly Leu Pro
    130                 135                 140

Gly Ala Gln Tyr Gly Gly Ile Ser Ser Arg Ser Gln Cys Asp Ser Phe
145                 150                 155                 160

Pro Ala Ala Leu Lys Pro Gly Cys Gln Trp Arg Phe Asp Trp Phe Gln
                165                 170                 175

Asn Ala Asp Asn Pro Asn Phe Thr Phe Lys Gln Val Gln Cys Pro Ser
            180                 185                 190
```

```
Glu Leu Thr Ser Arg Thr Gly Cys Lys Arg Asn Asp Asp Ser Gln Phe
        195                 200                 205

Pro Val Phe Thr Pro Pro Ser Gly Gly Gly Ser Asn Pro Ser Thr Pro
        210                 215                 220

Thr Thr Pro Pro Ser Ser Gly Gly Gly Ser Gly Cys Thr Ala Asp Lys
225                 230                 235                 240

Tyr Ala Gln Cys Gly Gly Ser Gly Trp Ser Gly Cys Thr Asn Cys Pro
            245                 250                 255

Ser Gly Ser Thr Cys Lys Thr Ile Asn Asp Tyr Tyr His Gln Cys Ala
            260                 265                 270
```